US010434187B2

(12) United States Patent
Coffield, III et al.

(10) Patent No.: US 10,434,187 B2
(45) Date of Patent: *Oct. 8, 2019

(54) USE OF MICRORNAS TO CONTROL VIRUS HELPER NUCLEIC ACIDS

(71) Applicant: ALPHAVAX, INC., Raleigh, NC (US)

(72) Inventors: Vernon McNeil Coffield, III, High Point, NC (US); Kurt I. Kamrud, Apex, NC (US); Jonathan F. Smith, Cary, NC (US)

(73) Assignee: APHAVAX, INC., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/459,330

(22) Filed: Mar. 15, 2017

(65) Prior Publication Data
US 2018/0050118 A1    Feb. 22, 2018

Related U.S. Application Data

(63) Continuation of application No. 14/173,702, filed on Feb. 5, 2014, now Pat. No. 9,597,414, which is a continuation of application No. 13/132,035, filed as application No. PCT/US2009/065900 on Nov. 25, 2009, now Pat. No. 8,680,258.

(60) Provisional application No. 61/118,954, filed on Dec. 1, 2008.

(51) Int. Cl.
| C07H 21/04 | (2006.01) |
| A61K 48/00 | (2006.01) |
| C12N 15/85 | (2006.01) |
| C12N 15/86 | (2006.01) |
| A61K 39/12 | (2006.01) |
| C07K 14/005 | (2006.01) |
| A61K 39/00 | (2006.01) |

(52) U.S. Cl.
CPC .......... *A61K 48/0041* (2013.01); *A61K 39/12* (2013.01); *C07K 14/005* (2013.01); *C12N 15/85* (2013.01); *C12N 15/86* (2013.01); *A61K 2039/5258* (2013.01); *C12N 2770/36143* (2013.01); *C12N 2800/40* (2013.01); *C12N 2800/50* (2013.01); *C12N 2820/60* (2013.01)

(58) Field of Classification Search
CPC .................................................. C12N 15/111
See application file for complete search history.

(56) References Cited

U.S. PATENT DOCUMENTS

| 4,650,764 A | 3/1987 | Temin et al. |
| 5,185,440 A | 2/1993 | Davis et al. |
| 5,505,947 A | 4/1996 | Johnston et al. |
| 5,643,576 A | 7/1997 | Johnston et al. |
| 5,789,245 A | 8/1998 | Dubensky et al. |
| 5,792,462 A | 8/1998 | Johnston et al. |
| 5,814,482 A | 9/1998 | Dubensky et al. |
| 5,843,723 A | 12/1998 | Dubensky et al. |
| 6,008,035 A | 12/1999 | Johnston et al. |
| 6,015,694 A | 1/2000 | Dubensky et al. |
| 6,105,686 A | 8/2000 | Dubensky et al. |
| 6,156,558 A | 12/2000 | Johnston et al. |
| 6,190,666 B1 | 2/2001 | Garoff et al. |
| 6,242,259 B1 | 6/2001 | Polo et al. |
| 6,376,236 B1 | 4/2002 | Dubensky et al. |
| 6,521,235 B2 | 2/2003 | Johnston et al. |
| 6,531,135 B1 | 3/2003 | Johnston et al. |
| 6,541,010 B1 | 4/2003 | Johnston et al. |
| 7,045,335 B2 | 5/2006 | Smith et al. |
| 7,078,218 B2 | 7/2006 | Smith et al. |
| 7,235,235 B2 | 6/2007 | Johnston et al. |
| 7,442,381 B2 | 10/2008 | Smith et al. |
| 2001/0016199 A1 | 8/2001 | Johnston et al. |
| 2002/0015945 A1 | 2/2002 | Polo et al. |
| 2003/0119182 A1 | 6/2003 | Smith et al. |
| 2005/0266550 A1 | 12/2005 | Rayner et al. |
| 2007/0166820 A1 | 7/2007 | Smith et al. |
| 2009/0075384 A1 | 3/2009 | Kamrud et al. |

FOREIGN PATENT DOCUMENTS

| WO | WO 1992/010578 | 6/1992 |
| WO | WO 2004/085660 | 10/2004 |
| WO | WO 2006/085983 | 8/2006 |

OTHER PUBLICATIONS

Ansardi et al. (1993) "Complementation of a poliovirus defective genome by a recombinant vaccinia virus which provides poliovirus P1 capsid precursor in trans," J. Viral. 67:3684-90.
Barnes et al. (2008) "Harnessing endogenous miRNAs to control virus tissue tropism as a strategy for developing attenuated virus vaccines," Cell Host and Microbe 4(3):239-48.
Baskerville et al. (2005) "Microarray profiling of microRNAs reveals frequent coexpression with neighboring miRNAs and host genes," RNA. 11(3):241-7.
Bernard et al. (2000) "Mutations in the E2 glycoprotein of Venezuelan equine encephalitis virus confer heparin sulfate interaction, low morbiditity, and rapid clearance form blood of mice," Viral. 276:93-103.

(Continued)

*Primary Examiner* — Kimberly Chong
(74) *Attorney, Agent, or Firm* — Leydig, Voit & Mayer, Ltd.

(57) ABSTRACT

Provided herein are helper nucleic acids comprising at least one microRNA target sequence of an endogenous, cellular microRNA and a nucleic acid encoding a viral protein, wherein the microRNA target sequence is located in the untranslated or translated region of the nucleic acid encoding the viral protein. Also provided are vector systems, compositions and cells comprising the provided helper nucleic acids and a vector of replicon. Methods of making virus-like replicon particles and populations of virus-like replicon particles (VRP) are also provided.

20 Claims, 26 Drawing Sheets

Specification includes a Sequence Listing.

(56) References Cited

OTHER PUBLICATIONS

Bosselman et al. (1987) "Replication-defective chimeric helper proviruses and factors affective generation of competent virus: expression of Moloney murine leukemia virus structural genes via the metallothionein promoter," Mol. Cell. Biol. 7(5):1797-806.

Danos et al. (1988) Safe and efficient generation of recombinant retroviruses with amphotropic and ecotropic host ranges, Proc. Natl. Acad. Sci. USA. 85:6460-4.

Dion et al. (1974) Isolation and characterization of RNA-directed DNA polymerase from a B-type RNA tumor virus, J. Viral. 14:40-6.

Fabiani et al. (2008) "miR-122 targeting with LNA/2'-0-methyl oligonucleotide mixmers, peptide nucleic acids (PNA), and PNA-peptide conjugates," RNA. 14:336-46.

Farh et al. (2005) "The widespread impact of mammalian microRNAs on mRNA repression and evolution," Science. 310(5755):1817-21.

Farrell et al. (1994) "Vaccine potential of a herpes simplex virus type 1 mutant with an essential glycoprotein deleted," J. Viral. 68:927-32.

Frolov et al. (1996) "Alphavirus-based expression vectors: strategies and applications," Proc. Natl. Acad. Sci. USA. 93:11371-1.

Frolov et al. (1997) "Sindbis virus replicons and Sindbis virus: assembly of chimeras and of particles deficient in virus RNA," J. Viral. 71(4):2819-29.

Geigenmuller-Gnirke et al. (1991) "Complementation between Sindbis viral RNAs produces infectious particles with a bipartite genome," Proc. Natl. Acad. Sci. USA 88(8):3253-7.

Glasgow et al. (1991) "Two mutations in the envelope glycoprotein E2 of semliki forest virus affecting the maturation and entry patterns of the virus alter pathogenicity for mice," Virol. 185:741-8.

Hahn et al. (1992) Infectious Sindbis virus transient expression vectors for studying antigen processing and presentation, Proc. Natl. Acad. Sci. USA 89:2679-83.

Heidner et al. (1994) "The amino-terminal residue of Sindbis virus glycoprotein E2 influences virus maturation, specific infectivity for BHK cells, and virulence in mice," J. Virol. 68:8064-70.

Heise et al. (2000) "A single amino acid change in nsP1 attenuates neurovirulence of the Sindbis-group alphavirus S.A. AR86," J. Virol. 74:4207-13.

Hill et al. (1997) "RNA-RNA recombination in Sindbis virus: roles of the 3' conserved motif, poly(A) tail, and nonviral sequences of template RNAs in polymerase recognition and template switching," J. Virol. 71(4):2693-704.

Inoue et al. (2004) "Recombinant Sendai virus vectors deleted in both the matrix and the fusion genes: efficient gene transfer with preferable properties," J. Gene. Med. 6:1069-81.

Johnston et al. (1988) "Selection for accelerated penetration in cell culture coselects for attenuated mutants of Venezuelan equine encephalitis virus," Virol. 162:437-43.

Kamrud et al. (2007) "Aiphavirus replicon approach to promoter-less analysis of IRES elements," Virol. 360(2):376-87.

Kapadia et al. (2008) "SARS vaccine based on a replication-defective vesicular stomatitis virus is more potent than one based on a replication-competent vector," Virol. 376:165-72.

Kelly et al. (2008) "Engineering microRNA responsiveness to decrease virus pathogenicity," Nat. Med. 14(11):1278-83.

Khromykh et al. (1988) "Encapsidation of the Flavivirus Kunjin replicon RNA by using a complementation system providing Kunjin virus structural proteins in trans," J. Virol. 72:5967-77.

Kinney et al. (1989) "The full-length nucleotide sequences of the virulent Trinidad donkey strain of Venezuelan equine encephalitis virus and its attenuated vaccine derivative, strain TC-83," Virol. 170:19-30.

Klimstra et al. (1999) "Infection of neonatal mice with Sindbis virus results in a systemic inflammatory response syndrome," J. Virol. 73:10387-98.

Kloosterman et al. (2007) "Targeted inhibition of miRNA maturation with morpholinos reveals a role for miR-375 in pancreatic islet development," PLoS Biol. 5(8):e203.

Kunkel et al. (1985) Rapid and efficient site-specific mutagenesis without phenotypic selection, Proc. Natl. Acad. Sci. USA. 82:488-92.

London et al. (1992) "Infectious enveloped RNA virus antigenic chimeras," Proc. Natl. Acad. Sci. USA. 89:207-11.

Markowitz et al. (1988) "A safe packaging line for gene transfer: separating viral genes on two different plasmids," J. Virol. 62(4):1120-4.

Miller et al. (1986) "Redesign of retrovirus packaging cell lines to avoid recombination leading to helper virus production," Mol. Cell. Biol. 6(8):2895-902.

Miller et al. (1989) "Improved retroviral vectors for gene transfer and expression," BioTechniques. 7(9):980-90.

Olmsted et al. (1984) "Sindbis virus mutants selected for rapid growth in cell culture display attenuated virulence in animals," Science. 225:424-7.

Polo et al. (1990) "Attenuating mutations in glycoproteins El and E2 of Sindbis virus produce a highly attenuated strain when combined in vitro" J. Virol. 64:4438-44.

Polo et al. (1999) "Stable alphavirus packaging cell lines for Sindbis virus- and Semliki Forest virus-derived vectors," Proc. Natl. Acad. Sci. USA. 96(8):4598-603.

Pushko et al. (1997) "Replicon-helper systems from attenuated Venezuelan equine encephalitis virus: expression of heterologous genes in vitro and immunization against heterologous pathogens in vivo," Virology. 239(2):389-401.

Raju et al. (1995) "Genesis of Sindbis virus by in vivo recombination of nonreplicative RNA precursors," J. Virol. 69(12):7391-401.

Rayner et al. (2000) "Aiphavirus vectors and vaccination," Rev. Med. Virol. 12:279-96.

Reap et al. (2007) "Development and preclinical evaluation of an alphavirus replicon particle vaccine for cytomegalovirus," Vaccine. 25(42):7441-9.

Schnell et al. (1997) "Construction of a novel virus that targets HIV-1-infected cells and controls HIV-1 infection," Cell. 90:849-57.

Scholle et al. (2004) "Trans-packaged West Nile virus-like particles: infectious properties in vitro and in infected mosquito vectors," J. Virol. 78:11605-14.

Sempere et al. (2004) "Expression profiling of mammalian microRNAs uncovers a subset of brain-expressed microRNAs with possible roles in murine and human neuronal differentiation," Genome Biol. 5(3):R13.

Simon-Mateo et al. (2006) "MicroRNA-guided processing impairs plum pox virus replication but the virus readily evolves to escape this silencing mechanism" J. Virol. 80(5):2429-36.

Smerdou et al. (1999) "Two-helper RNA sytem for production of recombinant semliki forest virus particles," J. Virol. 73(2):1092-8.

Smit et al. (2001) "PE2 cleavage mutants of Sindbis virus: correlation between viral infectivity and pH-dependent membrane fusion activation of the spike heterodimer," J. Virol. 75:11196-204.

Valoczi et al. (2004) "Sensitive and specific detection of microRNAs by northern blot analysis using LNA-modified oligonucleotide probes," Nucleic Acid Research 32(22):e175.

Weir et al. (1993) "Replication-incompetent herpesvirus vector delivery of an interferon alpha gene inhibits human immunodeficiency virus replication in human monocytes," Proc. Natl. Acad. Sci. USA 90:9140-4.

Weiss et al. (1991) "Recombination between Sindbis virus RNAs," J. Virol. 65(8):4017-25.

White et al. (2001) "Role of alpha/beta interferon in Venezuelan equine encephalitis virus pathogenesis: effect of an attenuating mutation in the 5' untranslated region," J. Virol. 75:3706-18.

Yoshii et al. (2005) "Packaging the replicon RNA of the Far-Eastern subtype of tick-borne encephalitis virus into single-round infectious particles: development of a heterologous gene delivery system," Vaccine. 23:3946-56.

International Search Report corresponding to International Patent Application No. PCT/US2009/065900, dated Mar. 5, 2010.

International Preliminary Report on Patentability corresponding to International Patent Application No. PCT/US2009/065900, dated Jun. 7, 2011.

(56) References Cited

OTHER PUBLICATIONS

Written Opinion corresponding to International Patent Application No. PCT/US2009/065900, dated Mar. 5, 2010.

USE OF MICRORNAS TO CONTROL VIRUS HELPER NUCLEIC ACIDS

CROSS-REFERENCE TO RELATED APPLICATIONS

This application is a continuation of U.S. application Ser. No. 14/173,702, filed Feb. 5, 2014, which is a continuation of U.S. application Ser. No. 13/132,035, filed Dec. 27, 2011, now U.S. Pat. No. 8,680,258, which is a 371 U.S. national stage of PCT/US2009/065900, filed Nov. 25, 2009, which claims the benefit of U.S. Provisional Application No. 61/118,954, filed on Dec. 1, 2008, each of which is incorporated by reference in its entirety.

BACKGROUND

Modern strategies for vaccination and gene therapy often involve the use of viral vectors. This is based on the fact that viruses have evolved useful techniques for invading the host and self-propagating. The goal is to harness those techniques to deliver immunizing antigens from a target disease organism or virus, while crippling the virus itself so that it cannot propagate and sicken its host. The simplest strategy has been the use of live, attenuated viruses, but this solution is obviously limited to vaccines for viral diseases. Even so, there is a concern that such attenuated viruses may mutate and become more virulent in the host. A more directed strategy is to design a vector based on a virus, but provide only the elements necessary for the virus to replicate within a cell, rather than propagate and spread throughout the host. Alphaviruses have been an attractive type of virus to use to design such a system. Flaviviruses, herpesviruses, lentiviruses and adenoviruses are other such systems.

All of these single- or restricted-cycle viruses utilize "helper" systems which separately provide some function of the parental virus from which they are derived. These helper systems are necessary to produce the single- or restricted-cycle virus particles, but ideally they are not carried along with those particles or recombined with the nucleic acids in the particles. However, whenever all portions of a viral genome are present in a cell at the same time, even if only transiently, there is the possibility that these elements will recombine to produce the parental virus.

SUMMARY OF THE DISCLOSURE

Provided herein are helper nucleic acids comprising at least one microRNA target sequence of an endogenous, cellular microRNA and a nucleic acid encoding a viral protein, wherein the microRNA target sequence is located in the untranslated or translated region of the nucleic acid encoding the viral protein. The viral protein is a structural protein or a protein essential for replication of the virus. Optionally, the viral protein is an alphavirus structural protein. Also provided are vector systems, compositions and cells comprising the provided helper nucleic acids and a vector or replicon.

Provided are methods of making virus-like replicon particles (VRP) (e.g., alphavirus-like replicon particles (ARP)) comprising transfecting a cell with a replicon, wherein the replicon comprises a packaging signal, and one or more helper nucleic acids described herein. The proteins necessary to make the VRP are encoded by one or more of the cell, the replicon or the helper nucleic acid. The cell is then cultured under conditions that allow for production of assembled virus-like replicon particles comprising the replicon.

Populations of alphavirus-like replicon particles (ARP) comprising (i) a first subset of particles comprising a replicon and (ii) a second subset of particles comprising the one or more provided helper nucleic acids, or a fragment thereof, and a replicon, are provided.

The details of one or more of the compositions and methods are set forth in the accompanying drawings and the description below. Other features, objects, and advantages will be apparent from the description and drawings, and from the claims.

DETAILED DESCRIPTION

Figure 1:
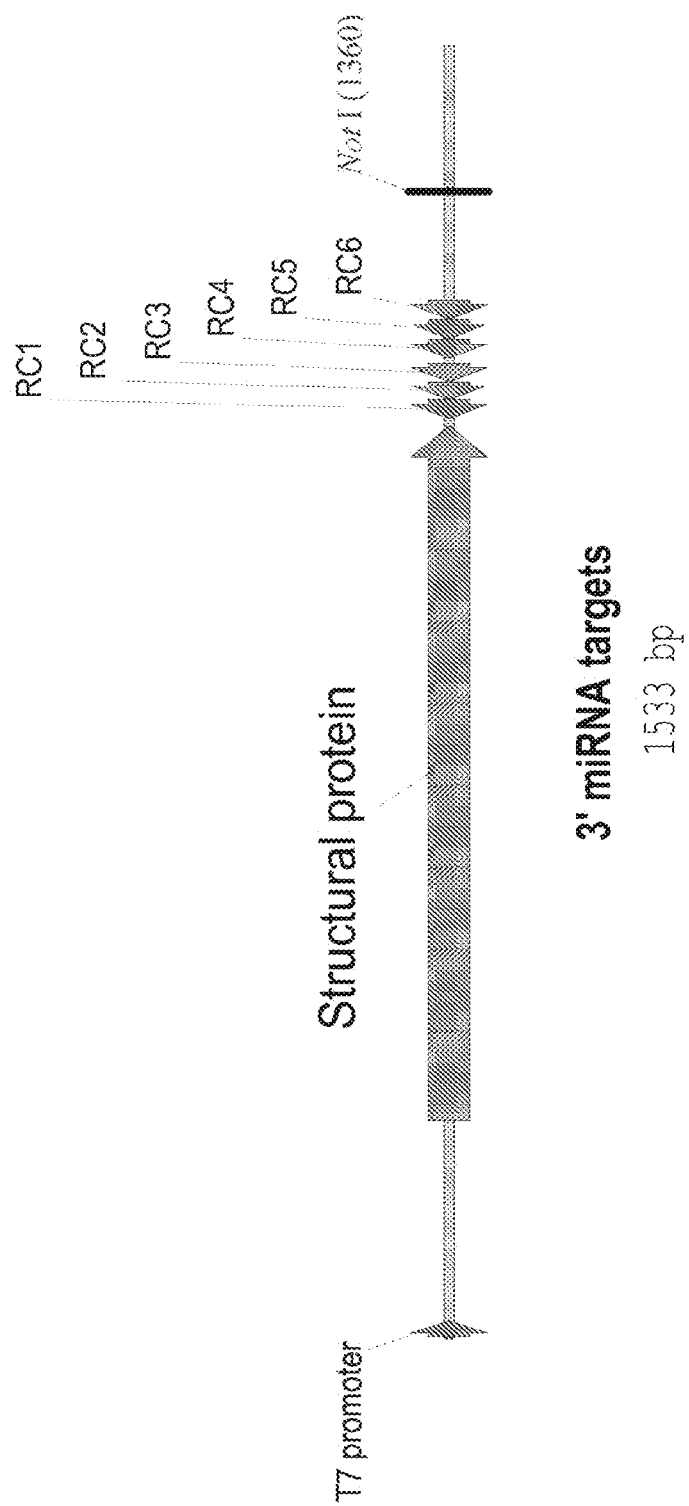
FIG. 1 is a schematic representation of the location of miRNA targets engineered into the 3' UTR of a nucleic acid encoding a structural protein. A nucleotide length of 1533 base pairs can occur when the structural protein is, for example, the capsid protein. The nucleotide length of 1533 base pairs is measured from the end of the T7 promoter to the NotI restriction site.
Figure 2:
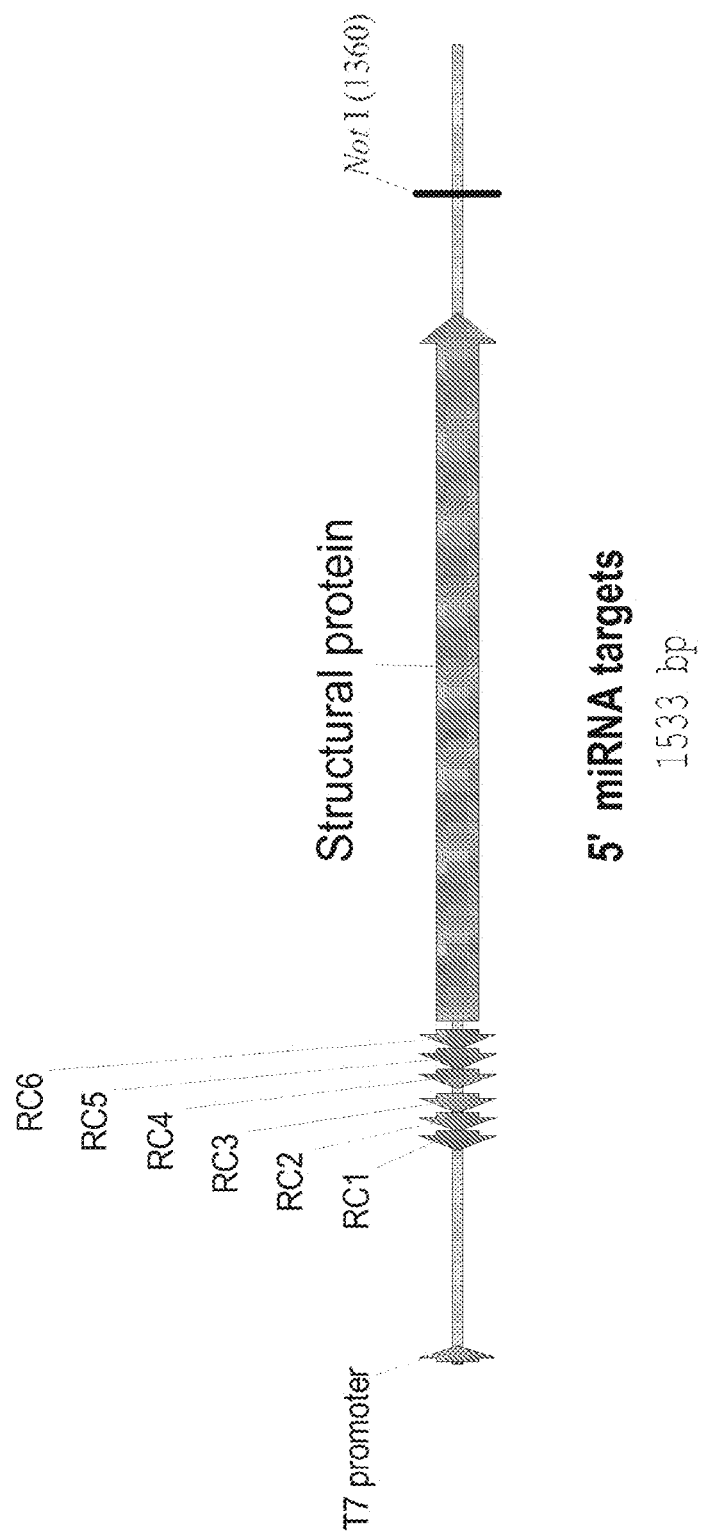
FIG. 2 is a schematic representation of the location of miRNA targets engineered into the 5' UTR of a nucleic acid encoding a structural protein. A nucleotide length of 1533 base pairs can occur when the structural protein is, for example, the capsid protein. The nucleotide length of 1533 base pairs is measured from the end of the T7 promoter to the NotI restriction site.
Figure 3:
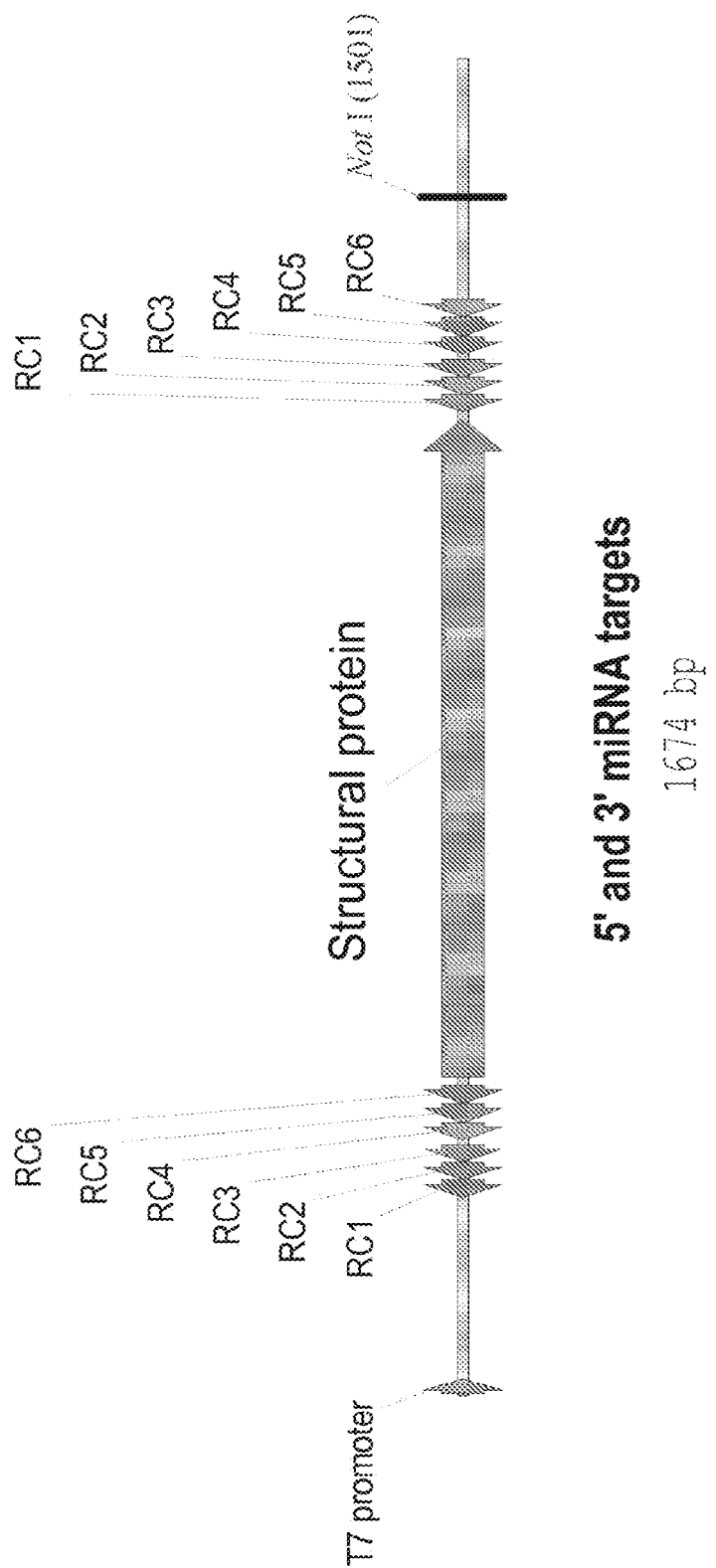
FIG. 3 is a schematic representation of the location of miRNA targets engineered into the 5' and 3' UTR of a nucleic acid encoding a structural protein. A nucleotide length of 1647 base pairs can occur when the structural protein is, for example, the capsid protein. The nucleotide length of 1647 base pairs is measured from the end of the T7 promoter to the NotI restriction site.

Provided herein are methods of exploiting microRNA, also referred to as miRNA, regulatory function to control aspects of replication of viral-based vector systems (such as alphavirus replicon-helper systems). Although the present disclosure focuses on the example of alphaviruses, it is contemplated that other viral-based vector systems including, for example, lentiviral, herpesviral and adenoviral vector systems, can be modified as described herein for alphaviruses.

The Alphavirus genus includes a variety of viruses, all of which are members of the Togaviridae family. The studies of these viruses have led to the development of techniques for vaccinating against the alphavirus diseases and against other diseases through the use of alphavirus vectors for the introduction of foreign genes and also for gene therapy applications. One strategy involving alphavirus vectors is the insertion of sequences encoding immunizing antigens of a pathogenic agents into a live, replicating strain of an alphavirus vector. Another strategy is to utilize a replicon vector to express the immunizing antigens. Such alphavirus replicon vectors can be packaged into alphavirus-like replicon particles, referred to herein as ARPs, by supplying the structural protein genes in trans. The structural proteins can be provided in a number of ways. The structural proteins can be provided by packaging cell lines engineered to express the proteins either in a constitutive or inducible manner (Polo et al., Proc. Natl. Acad. Sci. USA 96(8):4598-603 (1999)). The structural proteins can be expressed transiently from DNA plasmids under the control of a polymerase II promoter or they can be provided on helper RNAs that are replicated by the replicon vector itself (Pushko et al., Virology 239(2):389-401 (1997); Rayner et al., Rev. Med. Virol. 12:279-296 (2002)). Each of these approaches ultimately results in production of structural protein mRNAs, and translation of these mRNAs, in the cytoplasm of the cell used to package the replicon RNA. It has been demonstrated that replication competent alphaviruses can be generated by co-packaging of helper RNA or recombination of helper RNAs with replicon RNA (Geigenmuller-Gnirke et al., Proc. Natl. Acad. Sci. USA 88(8):3253-7 (1991); Weiss and Schlesinger, J. Virol. 65(8):4017-25 (1991); Raju et al., J. Virol. 69(12):7391-401 (1995); and Hill et al., J. Virol. 71(4):2693-704 (1997)). A significant advance in reducing the probability of generating replication competent alphaviruses was described when the structural protein genes were separated onto two different RNA helpers. Two separate recombination events are required to reconstitute a complete alphavirus genome when using a two helper RNA system. The probability of this event occurring is significantly lower than when using a single helper RNA system (Pushko et al., Virology 239(2):389-401 (1997); Frolov et al., J. Virol. 71(4):2819-29 (1997); and Smerdou and Liljestrom, J. Virol. 73(2):1092-8 (1999)). However, there are still theoretical predictions for replication competent alphaviruses to arise using a two helper RNA system, for example, there is the possibility that helper RNAs may be co-packaged, even in the absence of a defined packaging signal in the helper RNA.

MicroRNAs (miRNA) are small RNAs approximately 21-24 nucleotides (nt) in length that have been identified in cells and are associated with regulation of mRNA translation and stability. Numerous miRNAs have been identified that control cellular activities such as proliferation, cell death, fat metabolism, neuronal patterning in nematodes, hematopoietic differentiation and plant development. These small regulatory RNAs have been identified in a wide range of animals including mammals, fish, worms and flies. The miRNA sequences are transcribed from specific miRNA genes, as independent transcriptional units, throughout the genome or arc produced in coordination with intron processing of specific mRNAs thus combining control of protein expression with mRNA processing. The cellular production of miRNAs begins with transcription of large precursor primary miRNAs which are processed by a nuclear ribonuclease III-like enzyme, Drosha. The large precursor RNAs are termed pri-miRNAs and the smaller Drosha-processed species, termed pre-miRNAs, are exported from the nucleus by Exportin 5. The pre-miRNA, exported from the nucleus, is then processed in the cytoplasm by another ribonuclease III-like enzyme called Dicer into a mature miRNA. The mature miRNA is then transferred to the RNA-induced silencing complex (RISC) which guides the miRNA to its target RNA. The 5'-most 7 to 8 nucleotides (specifically nt 2-8) of the miRNA (sometimes referred to as the seed sequence) are involved in Watson-Crick base pairing with nucleotides in the 3' untranslated region (UTR) of the target mRNA. If the base pairing is perfect the target mRNA is cleaved by the RISC endonuclease activity. Alternatively, if the base pairing is imperfect the target mRNA becomes translationally inactive and protein expression is affected without mRNA degradation.

Provided herein are alphavirus helper systems that use miRNA elements to target the helper RNAs in environments that they are not intended to be functional in (such as in a vaccinated subject). The system design requires that the action of the endogenous, cellular miRNA on its target sequence (present on the helper RNA) must be absent or inhibited in the cells used to generate VRP, but be active (i.e., control helper replication) in cells of the subject. It is possible to inhibit cellular miRNAs by treating cells in which the helper function is desired (e.g., packaging cell lines such as Vero) with complementary RNA sequences specific for the miRNA of interest. There are at least 4 types of inhibitory RNAs that can be used to inhibit cellular miRNAs, and one or more of these can be introduced to the cell as provided in the methods described herein Inhibitory RNAs include, for example, modified oligonucleotides (2'-O-methylated or 2'-O-methoxyethyl), locked nucleic acids (LNA; see, e.g, Válóczi et al., Nucleic Acids Res. 32(22): e175 (2004)), morpholino oligonucleotides (see, e.g, Kloosterman et al., PLoS Biol 5(8):e203 (2007)), peptide nucleic acids (PNAs), PNA-peptide conjugates, LNA/2'-O-methylated oligonucleotide mixmers (see, e.g., Fabiani and Gait, RNA 14:336-46 (2008)) and mRNAs with multiple copies of the miRNA target engineered into the 3' UTR, sometimes referred to as miRNA sponges. The miRNA inhibitors function by sequestering the cellular miRNAs away from the mRNAs that normally would be targeted by them. As described herein, the miRNA inhibitors are added to the cells in which VRP will be produced from miRNA-targeted helpers and replicon RNA. The miRNA inhibitors suppress the miRNA control of targeted helper replication, thereby allowing normal viral structural protein expression from the helper(s) and packaging of the replicon RNA into VRP. The use of miRNA-targeted helper RNAs provides control of not only co-packaged helper RNAs but also of helper RNAs that have recombined with the replicon RNA. The latter would be accomplished because, as long as the miRNA target is maintained after the replicon-helper recombination event, this recombinant RNA molecule would still be targeted for control via the RNAi pathway described above.

Provided herein are methods of exploiting microRNA regulatory function to control aspects of replication of virus-based vector or replicon systems, for example, alphavirus-based vector or replicon systems. The Alphavirus genus includes a variety of viruses, all of which are members of the Togaviridae family. As used herein, the term alphavirus includes various species such as, for example Eastern Equine Encephalitis Virus (EEE), Venezuelan Equine Encephalitis Virus (VEE), Everglades Virus, Mucambo Virus, Pixuna Virus, Western Equine Encephalitis Virus (WEE), Sindbis Virus, Semliki Forest Virus, Middleburg Virus, Chikungunya Virus, O'nyong-nyong Virus, Ross River Virus, Barmah Forest Virus, Getah Virus, Sagiyama Virus, Bebaru Virus, Mayaro Virus, Una Virus, Aura Virus, Whataroa Virus, Babanki Virus, Kyzylagach Virus, Highlands J virus, Fort Morgan Virus, Ndumu Virus, and Buggy Creek Virus. The alphaviral genome is a single-stranded, messenger-sense RNA, modified at the 5'-end with a methylated cap and at the 3'-end with a variable-length poly (A) tract. Structural subunits containing a single viral protein, capsid, associate with the RNA genome in an icosahedral nucleocapsid. In the virion, the capsid is surrounded by a lipid envelope covered with a regular array of transmembrane protein spikes, each of which consists of a heterodimeric complex of two glycoproteins, E1 and E2. See, e.g., Pedersen et al., J. Virol. 14:40 (1974). Sindbis virus and Semliki Forest virus (SFV) are considered the prototypical alphaviruses and have been studied extensively. See Schlesinger, The Togaviridae and Flaviviridae, Plenum Publishing Corp., New York (1986). The VEE virus has been studied extensively, see, e.g., U.S. Pat. No. 5,185,440 and references cited therein. Alphaviruses useful in the constructs and methods provided herein include, but are not limited to, VEE, S.A. AR86, Sindbis (e.g., TR339, see U.S. Pat. No. 6,008,035), and SFV.

Alphavirus vector or replicon systems have been described. See, e.g., U.S. Pat. No. 5,185,440 to Davis et al., International Publication No. WO 92/10578; U.S. Pat. Nos. 5,505,947 and 5,643,576 to Johnston et al.; Hahn et al., Proc. Natl. Acad. Sci. USA 89:2679-83 (1992); U.S. Pat. No. 6,190,666 to Garoff et al.; U.S. Pat. Nos. 5,792,462; 6,156,558; 6,521,235; 6,531,135; 6,541,010 and 7,235,235 to Johnston et al.; U.S. Pat. Nos. 7,045,335 and 7,078,218 to Smith et al.; U.S. Pat. Nos. 5,814,482, 5,843,723, 5,789,245, 6,015,694, 6,105,686 and 6,376,236 to Dubensky et al.; U.S. Patent Publication No. 2002-0015945 by Polo et al.; U.S. Patent Publication No. 2001-0016199 by Johnston et al.; U.S. Patent Publication No. 2005-0266550 by Rayner et al.; Frolov et al., Proc. Natl. Acad. Sci. USA 93:11371-7 (1996); Pushko et al., Virology 239:389-401 (1997); Polo et al., Proc. Natl. Acad. Sci. USA 96(8):4598-603 (1999); Rayner et al., Rev. Med. Virol. 12:279-96 (2002); Geigenmuller-Gnirke et al., Proc. Natl. Acad. Sci. USA 88(8):3253-7 (1991); Weiss and Schlesinger, J. Virol. 65(8):4017-25 (1991); Raju et al., J. Virol. 69(12):7391-401 (1995); Hill et al., J. Virol. 71(4):2693-704 (1997); Frolov et al., J. Virol. 71(4):2819-29 (1997); and Smerdou and Liljestrom, J. Virol. 73(2):1092-8 (1999). Such replicon systems include one or more helper nucleic acid and one or more replicon. As an example, endogenous, cellular miRNA target sequences are incorporated into 1) capsid helper RNAs, 2) glycoprotein helper RNAs 3) or replicon vector RNAs. Naturally occurring endogenous, cellular miRNAs significantly inhibit the ability of the target-sequence containing helper nucleic acids to replicate in vitro and in vivo. The use of endogenous, cellular miRNA target sequences that are tissue-specific and/or development stage-specific in the replicon vector RNAs provides control of replicon expression only in tissues or at stages which are desired. As used herein, the phrase endogenous, cellular microRNA or miRNA refers to a microRNA encoded by a cell of an organism other than a virus. The organism can be unicellular or multi-cellular. Thus, the microRNA can be encoded by a cell of a prokaryote or eukaryote. Thus, the microRNA can be encoded by a cell of an animal, such as for example, a mammal or human.

Provided herein are helper nucleic acids comprising a 5' alphavirus recognition sequence; a nucleic acid sequence encoding an alphavirus structural protein; a 3' alphavirus replication recognition sequence; and at least one microRNA target sequence of an endogenous, cellular microRNA. Optionally, the helper nucleic acids can comprise at least one microRNA target sequence of an endogenous, cellular microRNA and a nucleic acid sequence encoding an alphavirus structural protein, wherein the microRNA target sequence is located in a region of the nucleic acid encoding the alphavirus structural protein. A region of the nucleic acid encoding the alphavirus structural protein can, for example, include the translated or untranslated region (UTR) (e.g., a 3'- or 5'-UTR) of the nucleic acid. The terms alphavirus helper(s), alphavirus helper nucleic acid(s), or alphavirus helper construct(s), refer to a nucleic acid molecule that is capable of expressing one or more alphavirus structural proteins. Smith et al. (International Patent Publication WO 2004/085660), Smith et al. (U.S. Pat. No. 7,045,335), and Kamrud et al. (U.S. Patent Publication No. 2009-0075384) describe numerous helper constructs useful for expressing alphavirus structural proteins in the production of ARPs.

The terms 5' alphavirus replication recognition sequence and 3' alphavirus replication recognition refer to the RNA sequences found in alphaviruses, sequences derived therefrom, or synthetic sequences based on conserved sequence among various alphaviruses, that are recognized by the nonstructural alphavirus replicase proteins and lead to replication of viral RNA. These sequences can, for example, be in the form of DNA to facilitate the preparation, mutation and/or manipulation of the helper nucleic acids described herein. The use of 5' and 3' replication recognition sequences results in the replication and/or transcription of the RNA sequence encoded between the two sequences.

The microRNA target sequence of the helper nucleic acid is located, for example, in the translated region, the 5' UTR, or the 3' UTR of the nucleic acid encoding the alphavirus structural protein. Optionally, multiple microRNA targets are located in different locations of the nucleic acid; e.g. at least one target sequence is located in the 3' UTR of the nucleic acid encoding the alphavirus structural protein and at least one target sequence is located in the 5' UTR of the nucleic acid encoding the alphavirus structural protein. When located in the translated region of the helper nucleic acid, the microRNA targets are optionally designed to be in-frame and to encode amino acids. However, the additional amino acids do not significantly affect the level of protein expression or its function. For example, the microRNA targets can be inserted in the leader sequence of the structural protein. In the case of alphavirus, the microRNA targets can be inserted into the sequence, referred to as "E3" (see below). It has been shown previously that additional amino acids may be inserted in E3 without detrimental effect (see, e.g., London et al., Proc. Natl. Acad. Sci. USA 89:207-11 (1992)). Optionally, the sequence of the translated region of the alphavirus structural protein can be altered to create a microRNA target sequence without changing the amino acid number or content of the protein. For example, conservative substitutions could be made in the nucleotide sequence of the alphavirus structural protein using the redundancy of the codon-assignments without altering the amino acid encoded by the codon. Optionally, the helper nucleic acid comprises two or more microRNA target sequences. Thus, the helper nucleic acid can comprise two, three, four, five, six, seven, eight, nine, ten, or more microRNA target sequences. Optionally, the helper nucleic acid comprises 1 to 10, 1 to 20, 1 to 30, 5 to 10, 5 to 20, 5 to 30, 10 to 20, 10 to 30, or 15 to 30 microRNA target sequences. Optionally, the microRNA target sequence has 100% complementarity to the endogenous, cellular microRNA. Alternatively, the microRNA target sequence has less than 100% complementarity to the endogenous, cellular microRNA. A percent complementarity indicates the percentage of residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). 100% complementary means that all the residues of a nucleic acid sequence will hydrogen bond with the same number of residues in a second nucleic acid sequence. Thus, the microRNA target sequence has 100%, 95%, 90%, 85%, 80%, 75%, 70% complementarity, or any percent complementarity between 100% and 70%, to the endogenous, cellular microRNA. Optionally, a portion of the microRNA target sequence, for example, the 5'-8 nucleotides, which is often referred to as the "seed" sequence, is identical (i.e., has 100% complementary) to the endogenous, cellular microRNA, while a second portion of the microRNA target sequence has less than 100% complementarity, e.g. 50%, to the endogenous, cellular microRNA. Optionally, the size of the microRNA target sequence is 5 to 10, 5 to 20, 5 to 30, 5 to 40, 5 to 50, 10 to 20, 10 to 30, 10 to 40, 10 to 50, 15 to 20, 15 to 30, 15 to 40, 15 to 50, 20 to 25, 20 to 30, 20 to 40, 20 to 50, 25 to 30, 25 to 40, or 25 to 50 nucleotides.

As discussed above, the helper nucleic acid comprises one or more alphavirus structural proteins. Thus, the helper nucleic acid comprises one or more than one alphavirus structural protein. As used herein, the terms alphavirus structural protein/protein(s) refers to one or a combination of the structural proteins encoded by alphaviruses. For example, the alphavirus structural protein is a Venezuelan equine encephalitis (VEE) virus structural protein. By way of another example, the alphavirus structural protein is selected from the group consisting of South African Arbovirus No. 86, Sindbis virus, Semliki Forest Virus, and Ross River Virus structural proteins. Alphavirus structural proteins are produced by the alphavirus as a polyprotein and are represented generally in the literature as C-E3-E2-6k-E1. E3 and 6k serve as membrane translocation/transport signals for the two glycoproteins, E2 and E1. Thus, use of the term E1 herein can refer to E1, E3-E1, 6k-E1, or E3-6k-E1, and use of the term E2 herein can refer to E2, E3-E2, 6k-E2, or E3-6k-E2. Typically, alphavirus structural proteins include the capsid protein, E1 glycoprotein, and E2 glycoprotein in the mature alphavirus (certain alphaviruses, such as Semliki Forest Virus, contain an additional protein, E3, in the mature coat). Thus, as an example, the helper nucleic acid comprises an alphavirus capsid protein. Optionally, the alphavirus capsid protein is a VEE capsid protein. As another example, the helper nucleic acid comprises an alphavirus glycoprotein. Optionally, the alphavirus glycoprotein is a VEE glycoprotein. A glycoprotein, as referred to herein, can be encoded by a nucleic acid sequence comprising a single open reading frame (orf) encoding E3-E2-6k-E1, an orf encoding E3-E2, an orf encoding 6k-E1, an orf encoding E3-E1, an orf encoding E3-6k-E1, an orf encoding 6k-E2, or an orf encoding E3-6k-E2.

The structural proteins of the alphavirus are distributed among one or more helper nucleic acid molecules (e.g., a first helper RNA (or DNA) and a second helper RNA (or DNA)). The same structural protein can be encoded by more than one helper nucleic acid. The helper nucleic acids encode at least one but not all alphavirus structural proteins, and a second helper nucleic acid encodes at least one alphavirus structural protein not encoded by a first helper nucleic acid. In addition, one or more structural proteins may be located on the same molecule as the replicon nucleic acid, provided that at least one alphavirus structural protein is not located on the replicon RNA such that the replicon and resulting alphavirus particle are propagation defective. As used herein, the term not located on means either total lack of the specified segment or the lack of a sufficient portion of the specified segment to render the segment inoperative or nonfunctional, in accordance with standard usage. See, e.g., U.S. Pat. No. 4,650,764 to Temin et al. The term replication defective as used herein is synonymous with propagation defective, and means that the particles contacted with a given host cell cannot produce progeny particles in the host cell, due to the absence of the helper function, i.e. the alphavirus structural proteins required for packaging the replicon nucleic acid. However, the replicon nucleic acid is capable of replicating itself and being expressed within the host cell into which it has been introduced.

In all of the helper nucleic acids described herein, it is understood that these molecules further comprise sequences necessary for expression (encompassing translation and where appropriate, transcription or replication signals) of the encoded structural protein sequences in the helper cells. Such sequences may include, for example, promoters, (either viral, prokaryotic or eukaryotic, inducible or constitutive), IRES elements, and 5' and 3' viral replicase recognition sequences. Optionally, one or more helper nucleic acids may include only the 5' and 3' viral replication recognition sequences (see Kamrud et al., U.S. Patent Publication No. 2009-0075384), thus functioning directly as replicable mRNAs when introduced into a eukaryotic cell. In the case of the helper nucleic acids expressing one or more glycoproteins, it is understood that these sequences are advantageously expressed with a leader or signal sequence at the N-terminus of the structural protein coding region in the nucleic acid constructs. The leader or signal sequence is derived from the alphavirus, for example E3 or 6k, or it is a heterologous sequence such as a tissue plasminogen activator signal peptide or a synthetic sequence. Thus, as an example, a first helper nucleic acid may be an RNA molecule encoding capsid-E3-E1, and the second helper nucleic acid may be an RNA molecule encoding capsid-E3-E2. Alternatively, the first helper RNA can encode capsid alone, and the second helper RNA can encode E3-E2-6k-E1. Additionally, packaging signal(s) or encapsidation sequence(s) that may be present in the viral genome are optionally not present in all of the helper nucleic acids. Thus, packaging signal(s) are, optionally, not located on all of the helper nucleic acids.

The helper nucleic acids described herein can be introduced into packaging cells, i.e. those cells in which a replicon is packaged by the structural proteins expressed from the helpers, in a number of ways. They can be expressed from one or more expression cassettes that have been stably transformed into the cells, thereby establishing packaging cell lines (see, e.g., U.S. Pat. No. 6,242,259). Alternatively, the helper nucleic acid is incorporated into the packaging cell genome prior to the introduction/expression of the RNA replicon vector. Optionally, the helper nucleic acid contains an inducible promoter such that expression of the structural proteins is induced with the appropriate stimulus just prior to, concomitant with, or after the introduction of the RNA replicon vector.

Alternatively, the RNAs can be introduced as RNA or DNA molecules that can be expressed in the helper cell without integrating into the cell genome. Methods of introduction include electroporation, viral vectors (e.g., SV40, adenovirus, nodavirus, astrovirus), and lipid-mediated transfection.

An alternative to multiple helper RNAs is the use of a single DNA molecule, which encodes all the polypeptides necessary for packaging the viral replicon RNA into infective alphavirus replicon particles (see, e.g., U.S. Pat. No. 7,045,335). Thus, as one example, the helper nucleic acid is an RNA. As another example, the helper nucleic acid is a DNA. The single DNA helper is introduced into the packaging cell by any means known including, but not limited to, electroporation, lipid-mediated transfection (lipofection), viral vector (e.g., adenovirus or SV-40), or calcium phosphate-mediated transfection. The DNA is typically electroporated into cells with a decreased voltage and increase in capacitance, as compared to that required for uptake of RNA. Thus, the conditions for electroporation of DNA into cells may vary from those required for the uptake of RNA, but can be determined by routine experimentation. In all electroporations, the value for the voltage and capacitance must be set so as to avoid destroying the ability of the packaging (host) cells to produce infective virus particles.

As provided herein and discussed in more detail below, the helper nucleic acids are used in combination with a replicon to produce alphavirus or alphavirus-like replicon particles. The terms alphavirus-like replicon particles (ARPs), or recombinant alphavirus particles, used interchangeably herein, mean a virion-like structural complex incorporating an alphavirus replicon RNA. The replicon optionally expresses one or more heterologous RNA sequences. Optionally, the virion-like structural complex includes one or more alphavirus structural proteins embedded in a lipid envelope enclosing a nucleocapsid that in turn encloses the RNA. The lipid envelope is typically derived from the plasma membrane of the cell in which the particles are produced. Optionally, the alphavirus replicon RNA is surrounded by a nucleocapsid structure comprised of the alphavirus capsid protein, and the alphavirus glycoproteins are embedded in the cell-derived lipid envelope. The structural proteins and replicon RNA may be derived from the same or different alphaviruses. For example, the replicon RNA and structural proteins are from VEE, see, e.g., U.S. Patent Publication 2005-0266550 by Smith et al. Optionally, the replicon RNA is derived from VEE and the structural proteins are derived from Sindbis Virus (see, e.g., U.S. Pat. No. 6,376,236 to Dubensky et al.). The alphavirus replicon particles are infectious but propagation defective, i.e., the replicon RNA cannot propagate beyond the host cell into which the particles initially infect, in the absence of the helper nucleic acid(s) encoding the alphavirus structural proteins.

Thus, provided is a population of alphavirus-like replicon particles (ARP) comprising (i) a first subset of particles comprising a replicon and (ii) a second subset of particles comprising one or more helper nucleic acids as described herein which comprise one or more miRNA target sequences, or a fragment thereof, and a replicon. Optionally, the ARPs are derived from Venezuelan equine encephalitis (VEE) virus, South African Arbovirus No. 86, Sindbis virus, Semliki Forest Virus, or Ross River Virus. Optionally, as discussed below, the replicon encodes a polypeptide, an immunostimulatory polypeptide, an immunogenic polypeptide, or a therapeutic product. A population of alphavirus replicon particles provided herein contains no detectable replication-competent virus particles, as determined by passage on permissive cells in culture. Optionally, the population of alphavirus replicon particles contains one or more attenuating mutations in either an alphavirus structural protein or an alphavirus nonstructural protein or both an alphavirus structural protein and an alphavirus nonstructural protein.

The terms alphavirus RNA replicon, replicon, replicon RNA, alphavirus replicon RNA, alphavirus RNA vector replicon, are used interchangeably to refer to an RNA molecule expressing nonstructural polypeptides such that it can direct its own replication (amplification) and comprises, at a minimum, 5' and 3' viral replication recognition sequences (e.g., 5' and 3' alphavirus replication recognition sequences), coding sequences for viral nonstructural proteins (e.g., alphavirus nonstructural proteins), and a polyadenylation tract. As used herein, the terms 5' alphavirus replication recognition sequence and 3' alphavirus replication recognition sequence refer to the sequences found in alphaviruses, or sequences derived therefrom, that are recognized by the nonstructural alphavirus replicase proteins and lead to replication of viral RNA. These are sometimes referred to as the 5' and 3' ends, or alphavirus 5' and 3' sequences. These sequences can be modified by standard molecular biological techniques, see for example U.S. Patent Publication No. 2007-0166820 and U.S. Patent Publication No. 2009-0075384) to further minimize the potential for recombination or to introduce cloning sites, with the proviso that they must be recognized by the alphavirus replication machinery. In addition, the replicon optionally contains one or more elements to direct the expression, meaning transcription and translation, of a heterologous RNA sequence. It is optionally engineered to express alphavirus structural proteins. For example, Smith et al. (International Publication WO 2004/085660) and Smith et al. (U.S. Pat. No. 7,045,335) describe numerous constructs for such alphavirus RNA replicons, which are herein incorporated by reference in their entireties.

The alphavirus RNA replicon provided herein is designed to express one or more heterologous coding sequence(s) or functional RNA(s) of interest, also referred to herein as a heterologous RNA or heterologous sequence, which can be chosen from a wide variety of sequences derived from viruses, prokaryotes or eukaryotes, including native, modified or synthetic antigenic proteins, peptides, epitopes or immunogenic fragments. Thus, the replicon can encode a polypeptide. Suitable polypeptides include, for example, immunostimulatory molecules. Immunostimulatory polypeptides include, for example, IL-12. Optionally, the replicon encodes an immunogenic polypeptide. Immunogenic polypeptides include, for example, immunogenic polypeptides derived from cancer cells, tumor cells, toxins or an infectious agent. Infectious agents include, for example, viruses, bacteria, fungi and parasites. As used herein, an immunogenic polypeptide, immunogenic peptide, or immunogen includes any peptide, protein or polypeptide that elicits an immune response in a subject. Optionally, the immunogenic polypeptide is suitable for providing some degree of protection to a subject against a disease. These terms can be used interchangeably with the term antigen. Optionally, the immunogenic polypeptide can comprise, consist essentially of or consist of one or more epitopes. As used herein, an epitope is a set of amino acid residues which is involved in recognition by a particular immunoglobulin or immunoglobulin fragment.

Optionally, the replicon encodes a therapeutic product, such as, for example, a therapeutic protein or an inhibitory nucleic acid. Inhibitory nucleic acid includes an antisense molecule, a triplex forming oligonucleotide, an external guide sequence, an aptamer, an siRNA, an miRNA, an shRNA and a ribozyme.

Optionally, the replicon does not express a polypeptide or a therapeutic product. Such an "empty" replicon can be packaged into a VRP and used as an adjuvant to enhance the immunogenicity of other products, including other VRPs.

As used herein, expression directed by a particular sequence is the transcription of an associated downstream sequence. If appropriate and desired for the associated sequence, then the term expression also encompasses translation (protein synthesis) of the transcribed or introduced RNA. Optionally, transcription and translation of the replicon, heterologous RNAs, and helper RNAs are controlled separately by different regulatory elements. Optionally, control of nucleic acid expression at the level of translation is accomplished by introducing an internal ribosome entry site (IRES) downstream of the promoter, e.g., the alphavirus 26S subgenomic promoter, and upstream of the coding sequence, e.g., for the heterologous sequence or an alphavirus structural protein, to be translated. This can be referred to as a subgenomic promoter-IRES-heterologous nucleic acid of interest (NOI) cassette. Optionally, a spacer sequence is incorporated in between the alphavirus 26S subgenomic promoter and the IRES element. The spacer sequence provides optimal spacing between these two elements to enhance the translation from the IRES. The IRES element is positioned so that it directs translation of the mRNA, thereby minimizing, limiting or preventing initiation of translation of the mRNA from the methyl-7-guanosine (5')pppN structure present at the 5' end of the subgenomic mRNA (the "cap"). Such IRES-directed translation is sometimes referred to as "cap-independent" translation. These constructs result in the IRES controlling translation of a heterologous sequence independently of promoter-driven transcription (See, e.g., U.S. Pat. No. 7,442,381 to Smith et al.). IRES elements from many different sources can be employed, including viral IRES elements from picornaviruses, e.g., poliovirus (PV) or the human enterovirus 71, e.g. strains 7423/MS/87 and BrCr thereof; from encephalomyocarditis virus (EMCV); from foot-and-mouth disease virus (FMDV); from flaviviruses, e.g., hepatitis C virus (HCV); from pestiviruses, e.g., classical swine fever virus (CSFV); from retroviruses, e.g., murine leukemia virus (MLU); from lentiviruses, e.g., simian immunodeficiency virus (SIV); from cellular mRNA IRES elements such as those from translation initiation factors, e.g., eIF4G or DAP5; from transcription factors, e.g., c-Myc or NF-κB-repressing factor (NRF); from growth factors, e.g., vascular endothelial growth factor (VEGF), fibroblast growth factor (FGF-2) and platelet-derived growth factor B (PDGF B); from homeotic genes, e.g., Antennapedia; from survival proteins, e.g., X-linked inhibitor of apoptosis (XIAP) or Apaf-1; from chaperones, e.g., immunoglobulin heavy-chain binding protein BiP, plant viruses, as well as any other IRES elements. The term transcription as used herein includes the production of RNA from a recombinant replicon or helper nucleic acid, which can itself be an RNA molecule.

Optionally, promoterless helpers can be employed. Such helper molecules do not contain a promoter; rather, they are introduced as replicable RNAs comprising 5' and 3' replication recognition sequences. Translation of promoterless helper nucleic acids occurs via the 5' cap on the RNA molecule. Optionally, in the absence of any promoter element on the helper nucleic acid, an IRES element may be included to direct translation.

Optionally, one or more of the nucleic acids encoding the alphavirus structural proteins, i.e., the capsid, E1 glycoprotein and E2 glycoprotein, or the replicon construct, contain one or more attenuating mutations. An attenuating mutation refers to a nucleotide deletion, addition, or substitution of one or more nucleotide(s), or a mutation that comprises rearrangement or chimeric construction which results in a loss of virulence in a live virus containing the mutation as compared to the appropriate wild-type virus. The phrases attenuating mutation and attenuating amino acid, as used herein, also mean a nucleotide mutation that may or may not be in a region of the viral genome encoding polypeptides or an amino acid coded for by a nucleotide mutation. In the context of a live virus, attenuating mutations result in a decreased probability of the alphavirus causing disease in its host (i.e., a loss of virulence), in accordance with standard terminology, whether the mutation be a substitution mutation, or an in-frame deletion or addition mutation. See, e.g., Davis et al., Microbiology, 4$^{th}$ Ed., 156-158 (1990). The phrase attenuating mutation excludes mutations which would be lethal to the virus, unless such a mutation is used in combination with a restoring mutation which renders the virus viable, albeit attenuated. Methods for identifying suitable attenuating mutations in the alphavirus genome are known. Olmsted et al., describes a method of identifying attenuating mutations in Sindbis virus by selecting for rapid growth in cell culture (Olmsted et al., Science 225:424 (1984)). Johnston and Smith, describe the identification of attenuating mutations in VEE by applying direct selective pressure for accelerated penetration of BHK cells (Johnston and Smith, Virology 162:437 (1988)). Attenuating mutations in alphaviruses have been described in the art, e.g. White et al., J. Virology 75:3706 (2001); Kinney et al., Virology 70:19 (1989); Heise et al., J. Virology 74:4207 (2000); Bernard et al., Virology 276:93 (2000); Smith et al., J. Virology 75:11196 (2001); Heidner and Johnston, J. Virology 68:8064 (1994); Klimstra et al., J. Virology 73:10387 (1999); Glasgow et al., Virology 185:741 (1991); Polo and Johnston, J. Virology 64:4438 (1990); and Smerdou and Liljestrom, J. Virology 73:1092 (1999).

Appropriate attenuating mutations depend upon the alphavirus used. For example, when the alphavirus is VEE, suitable attenuating mutations include those selected from the group consisting of codons at E2 amino acid position 76 which specify an attenuating amino acid, preferably lysine, arginine, or histidine as E2 amino acid 76; codons at E2 amino acid position 120 which specify an attenuating amino acid, preferably lysine as E2 amino acid 120; codons at E2 amino acid position 209 which specify an attenuating amino acid, preferably lysine, arginine, or histidine as E2 amino acid 209; codons at E1 amino acid 272 which specify an attenuating mutation, preferably threonine or serine as E1 amino acid 272; codons at E1 amino acid 81 which specify an attenuating mutation, preferably isoleucine or leucine as E1 amino acid 81; and codons at E1 amino acid 253 which specify an attenuating mutation, preferably serine or threonine as E1 amino acid 253. Additional attenuating mutations include deletions or substitution mutations in the cleavage domain between E3 and E2 such that the E3/E2 polyprotein is not cleaved; this mutation in combination with the mutation at E1-253 is a preferred attenuated strain for use in this invention. Similarly, mutations present in existing live vaccine strains, e.g. strain TC83 (see, e.g., Kinney et al., Virology 170:19-30 (1989), particularly the mutation at nucleotide 3), are also optionally employed in the particles made by the provided methods.

Where the alphavirus is the South African Arbovirus No. 86 (S.A. AR86), suitable attenuating mutations include those selected from the group consisting of codons at nsP1 amino acid position 538 which specify an attenuating amino acid, preferably isoleucine as nsP1 amino acid 538; codons at E2 amino acid position 304 which specify an attenuating amino acid, preferably threonine as E2 amino acid position 304; codons at E2 amino acid position 314 which specify an attenuating amino acid, preferably lysine as E2 amino acid 314; codons at E2 amino acid position 376 which specify an attenuating amino acid, preferably alanine as E2 amino acid 376; codons at E2 amino acid position 372 which specify an attenuating amino acid, preferably leucine as E2 amino acid 372; codons at nsP2 amino acid position 96 which specify an attenuating amino acid, preferably glycine as nsP2 amino acid 96; and codons at nsP2 amino acid position 372 which specify an attenuating amino acid, preferably valine as nsP2 amino acid 372. Suitable attenuating mutations wherein other alphaviruses are employed are known to those skilled in the art.

Attenuating mutations are introduced into the RNA by performing site-directed mutagenesis on the cDNA which encodes the RNA, in accordance with known procedures. See, e.g., Kunkel, Proc. Natl. Acad. Sci. USA 82:488 (1985), the disclosure of which is incorporated herein by reference in its entirety. Alternatively, mutations are introduced into the RNA by replacement of homologous restriction fragments in the cDNA which codes for the RNA, in accordance with known procedures, or in cDNA copies using mutagenic polymerase chain reaction methods.

Optionally, the helper nucleic acids contain mutations that would be lethal to the virus if incorporated into its native configuration. For example, the alphavirus capsid and glycoprotein genes of the VEE genome are normally encoded in a single open-reading frame (ORF). During translation of this ORF, the capsid cleaves itself from the growing polypeptide by virtue of an autoprotease activity. The protease activity is based on an active serine motif similar to that of chymotrypsin, which requires interaction of three distinct amino acid residues (serine, aspartate and histidine). In the VEE capsid gene, the serine, aspartate and histidine residues are located at amino acids 226, 174 and 152, respectively. Mutagenesis of one or all of these residues will compromise the protease activity of the capsid and result in non-viable viruses. Any number of mutations are possible at each residue, and so are referred to collectively as "m226, m174, or m152", wherein the "m" designates "mutant." The actual residue numbers are different for each alphavirus but are determined from primary amino acid sequence of the structural protein ORF. In the context of a two helper system, in which the capsid gene is provided on a helper nucleic acid separately from the glycoprotein gene, there is no requirement for autoprotease activity. However, if the autoprotease activity of the capsid protein is disabled, any recombination event that brought the glycoprotein gene into the same ORF as the capsid gene would result in a non-functional virus. This is because the capsid protein would be unable to cleave itself from the growing polypeptide (e.g., from the glycoprotein). Therefore, incorporation of such a mutation in the capsid gene ablates the autoprotease function but leaves the RNA packaging function of the capsid protein unaltered, thereby reducing further the probability of producing a replication competent virus.

Also provided are compositions comprising a first helper nucleic acid as described herein and a replicon. Optionally, the composition comprises a second helper nucleic acid comprising at least one microRNA target sequence of an endogenous, cellular microRNA and a nucleic acid encoding an alphavirus structural protein, wherein the microRNA target sequence is located in the translated or untranslated region (UTR) of the nucleic acid encoding the alphavirus structural protein, and wherein the first and second helper nucleic acids encode different alphavirus structural proteins. For example, the first helper nucleic acid encodes at least one but not all alphavirus structural proteins, and the second helper nucleic acid encodes at least one alphavirus structural protein not encoded by the first helper nucleic acid. The first and second helper nucleic acids comprise the same or different microRNA target sequences. Optionally, an alphavirus structural protein on the first helper nucleic acid is the alphavirus capsid protein and an alphavirus structural protein on the second helper nucleic acid is an alphavirus glycoprotein or vice versa. Optionally, the composition further comprises a packaging cell. Suitable packaging cells are discussed in more detail below. As discussed above, optionally the replicon encodes a polypeptide, an immunogenic polypeptide, an immunostimulatory polypeptide or a therapeutic product.

Also provided herein are methods for the preparation of infective, propagation-defective, virus-like replicon particles in cell culture. Thus, provided is a method of making virus-like replicon particles (VRP) comprising (a) transfecting a cell with (i) a replicon, and (ii) one or more helper nucleic acids as described herein, wherein the structural proteins necessary to make the virus-like replicon particle are encoded by one or more of the cell, the replicon or the helper nucleic acid; and culturing the cell under conditions that allow for production of assembled virus-like replicon particles comprising the replicon. Optionally, the replicon comprises a packaging signal. Optionally, the virus-like replicon particles further comprise the helper nucleic acid(s) or a fragment thereof. As utilized herein, a fragment thereof is defined as a portion of the helper nucleic acid that contains the microRNA target sequence or sequences. By way of an example, the structural proteins necessary to make a virus-like replicon particle are encoded by the helper nucleic acid(s). Optionally, the cell is transfected with a first helper nucleic acid and a second helper nucleic acid, wherein the first helper nucleic acid encodes at least one but not all the structural proteins necessary to make a virus-like replicon particle and the second helper nucleic acid encodes at least one or more alphavirus structural proteins not encoded by the first helper nucleic acid. Multiple different nucleic acid molecules, e.g. the first and second helper nucleic acids and the replicon nucleic acid, can be co-introduced into the packaging cell. Optionally, all three molecules can be RNA or DNA, or one or more molecules may be RNA and the other molecules can be DNA. Optionally, an inhibitor is introduced into the cell culture, e.g., by electroporation or by lipid-based transfection, to inhibit the activity of the endogenous, cellular microRNA(s) during packaging of the replicon RNA. Optionally, the packaging cell is selected from those cells or cell lines which do not contain the microRNAs that recognize the microRNA target sequences present on the helper nucleic acids. Optionally, the replicon encodes the targets to the endogenous, cellular microRNA (e.g., tissue-specific or development-stage specific microRNAs). Optionally, the method further comprises the step of isolating the VRPs. The virus-like replicon particles are propagation defective and infective. In alphavirus replicon particles (ARPs), an alphavirus vector or replicon, is optionally engineered to contain and express one or more genes of interest. Alternatively, ARPs that do not express a gene of interest or an inhibitory molecule, sometimes referred to as an empty ARP, (see, e.g., WO2006/085983 to Johnston et al.) are used as adjuvants to enhance the response to an immunogen, including another ARP. Thus, the replicon can encode a polypeptide, an immunostimulatory molecule, an immunogenic polypeptide, a therapeutic molecule, or nothing, as discussed above. The alphavirus replicon vector can be derived from any alphavirus, such as Venezuelan Equine Encephalitis (VEE) virus, Sindbis virus, e.g. strain TR339, South African Arbovirus No. 86, and Semliki Forest virus, among others. The replicon is then introduced into cells in culture that are permissive for the replication of alphaviruses and in which the structural proteins of the alphavirus are also expressed, so that the replicon is packaged by the structural proteins into ARPs. Methods for the economical and efficient production of high yields of alphavirus replicon particles are described in U.S. Pat. No. 7,078,218 to Smith et al., as are specific attenuated strains and viruses useful for the production of an ARP.

Provided herein are cells comprising one or more helper nucleic acids as described herein and one or more replicons. The cell, also referred to as a helper cell or packaging cell, are used to produce infectious, propagation defective alphavirus particles. The cell must express or be capable of expressing alphavirus structural proteins sufficient to package the replicon nucleic acid. The structural proteins arc produced from one or more RNAs that are introduced into the helper cell concomitantly with or prior to introduction of the replicon vector. Such RNAs are optionally stably transformed into the packaging cell line. Thus, provided is a cell comprising a first helper nucleic acid as described herein comprising at least one microRNA target sequence of an endogenous, cellular microRNA and a replicon. The cell optionally further comprises an inhibitor of the endogenous, cellular microRNA. Such inhibitors, which are small RNA molecules, can be introduced directly into the packaging cell, concomitantly with the helper nucleic acid(s). As discussed above, optionally the replicon encodes a polypeptide, an immunogenic polypeptide or a therapeutic product. Optionally, the cell comprises a second helper nucleic acid comprising at least one microRNA target sequence of an endogenous, cellular microRNA and a nucleic acid encoding an alphavirus structural protein, wherein the microRNA target sequence is located in the translated or untranslated region (UTR) of the nucleic acid encoding the alphavirus structural protein, and wherein the first and second helper nucleic acids encode different alphavirus structural proteins. The first and second helper nucleic acids comprise the same or different microRNA target sequences. Optionally, the alphavirus structural protein on the first helper nucleic acid is an alphavirus capsid protein and the alphavirus structural protein on the second helper nucleic acid is an alphavirus glycoprotein or vice versa. By way of example, the first helper RNA includes RNA encoding at least one alphavirus structural protein but does not encode all alphavirus structural proteins. Optionally, the first helper RNA comprises RNA encoding the alphavirus E1 glycoprotein, but not encoding the alphavirus capsid protein and the alphavirus E2 glycoprotein. Alternatively, the first helper RNA comprises RNA encoding the alphavirus E2 glycoprotein, but not encoding the alphavirus capsid protein and the alphavirus E1 glycoprotein. Optionally, the first helper RNA comprises RNA encoding the alphavirus E1 glycoprotein and the alphavirus E2 glycoprotein, but not the alphavirus capsid protein. The first helper RNA optionally comprises RNA encoding the alphavirus capsid, but none of the alphavirus glycoproteins. As another example, the first helper RNA may comprise RNA encoding the capsid and one of the glycoproteins, i.e., either E1 or E2, but not both. In combination with any one of these first helper RNAs, the second helper RNA encodes at least one alphavirus structural protein not encoded by the first helper RNA. For example, where the first helper RNA encodes only the alphavirus E1 glycoprotein, the second helper RNA encodes one or both of the alphavirus capsid protein and the alphavirus E2 glycoprotein. Where the first helper RNA encodes only the alphavirus capsid protein, the second helper RNA includes RNA encoding one or both of the alphavirus glycoproteins. Where the first helper RNA encodes only the alphavirus E2 glycoprotein, the second helper RNA encodes one or both of the alphavirus capsid protein and the alphavirus E1 glycoprotein. Where the first helper RNA encodes both the capsid and alphavirus E1 glycoprotein, the second helper RNA includes RNA encoding one or both of the alphavirus capsid protein and the alphavirus E2 glycoprotein.

The terms helper cell and packaging cell are used interchangeably herein and refer to the cell in which alphavirus replicon particles are produced. The helper cell comprises a set of helpers that encode one or more alphavirus structural proteins. As disclosed herein, the helpers may be RNA or DNA. The cell can be any cell that is alphavirus-permissive, i.e., cells that are capable of producing alphavirus particles upon introduction of a viral RNA transcript. Alphaviruses have a broad host range. Examples of suitable packaging cells include, but are not limited to, Vero cells, baby hamster kidney (BHK) cells, chicken embryo fibroblast cells, DF-1, 293, 293T, Chinese Hamster Ovary (CHO) cells, and insect cells. The helper or packaging cell may optionally include a heterologous RNA-dependent RNA polymerase and/or a sequence-specific protease. The nucleic acids encoding alphavirus structural proteins can be present in the helper cell transiently or by stable integration into the genome of the helper cell. The nucleic acid encoding the alphavirus structural proteins that are used to produce alphavirus particles can be under the control of constitutive and/or inducible promoters. For example, the alpha virus structural protein coding sequences are provided on a single DNA helper (see, e.g., U.S. Pat. No. 7,045,335 to Smith et al.) or as two helper constructs comprising an IRES element in which the translation of these coding sequences can be controlled by the activity of an IRES element. Optionally, the IRES element are active in the specific helper cell type and not active, or minimally active in other cells types. Optionally, the helper(s) may comprise a subgenomic promoter-IRES-structural protein nucleic acid cassette, in which the subgenomic promoter directs transcription of RNA and the IRES directs most or all expression of the structural protein. The helper cells comprise nucleic acid sequences encoding the alphavirus structural proteins in a combination and/or amount sufficient to produce an alphavirus particle when a recombinant replicon nucleic acid is introduced into the cell under conditions whereby the alphavirus structural proteins are produced and the recombinant replicon nucleic acid is packaged into alphavirus particle.

A promoter for directing transcription of RNA from DNA, i.e., a DNA dependent RNA polymerase, can be employed to produce the provided nucleic acids. A promoter is a sequence of nucleotides recognized by a polymerase and sufficient to cause transcription of an associated (downstream) sequence. In the RNA helper systems and to produce the replicon RNA, a promoter is utilized to synthesize RNA in an in vitro transcription reaction, and specific promoters suitable for this use include the SP6, T7, and T3 RNA polymerase promoters. In the DNA helper systems, the promoter functions within the packaging cell to direct transcription of messenger RNA encoding structural proteins necessary for packaging. Potential promoters for in vivo transcription of the construct include eukaryotic promoters such as RNA polymerase II promoters, RNA polymerase III promoters, or viral promoters such as MMTV and MoSV LTR, SV40 early region, RSV or CMV. Many other suitable mammalian and viral promoters are available. Alternatively, DNA dependent RNA polymerase promoters from bacteria or bacteriophage, e.g., SP6, T7, and T3, may be employed for use in vivo, with the matching RNA polymerase being provided to the cell, either via a separate plasmid, RNA vector, or viral vector. Optionally, the matching RNA polymerase can be stably transformed into a helper cell line under the control of an inducible promoter.

DNA constructs that function within a cell can function as autonomous plasmids transfected into the cell or they can be stably transformed into the genome. The promoter is optionally a constitutive promoter, i.e., a promoter which, when introduced into a cell and operably linked to a downstream sequence, directs transcription of the downstream sequence upon introduction into the cell, without the need for the addition of inducer molecules or a change to inducing conditions. Alternatively, the promoter may be regulated, i.e., not constitutively acting to cause transcription of the associate sequence. A regulated promoter can, for example be inducible. An inducible promoter acts so that the cell only produces the functional messenger RNA encoded by the construct when the cell is exposed to the appropriate stimulus (inducer). An inducible promoter transcribes the associated sequence only when (i) an inducer molecule is present in the medium in or on which the cells are cultivated, or (ii) conditions to which the cells are exposed are changed to be inducing conditions. When using an inducible promoter, the helper constructs are introduced into the packaging cell concomitantly with, prior to (either transiently or through stably transformation of the packaging cell line), or after exposure to the inducer, and expression of the alphavirus structural proteins occurs when both the constructs and the inducer are present. Alternatively, constructs designed to function within a cell can be introduced into the cell via a viral vector, e.g., adenovirus, poxvirus, adeno-associated virus, SV40, retrovirus, nodavirus, picornavirus, vesicular stomatitis virus, and baculoviruses with mammalian pol II promoters.

Optionally, the RNA vector replicon is transcribed in vitro from a DNA plasmid and then introduced into the helper cell by electroporation. Alternatively, the RNA vector replicon is transcribed in vivo from a DNA vector plasmid that is transfected into the helper cell (see., e.g., U.S. Pat. No. 5,814,482 to Dubensky et al.), or it is delivered to the helper cell via a virus or virus-like particle. Once an RNA transcript (mRNA) encoding the helper or RNA replicon vectors is present in the helper cell (either via in vitro or in vivo approaches), it is eventually translated to produce the encoded polypeptides or proteins.

Methods of inducing an immune response in a subject comprising administering to the subject a population of virus-like particles as described herein or as made by the methods described herein are also provided. Pharmaceutical compositions comprising an immunogenic amount of the infectious, propagation defective virus-like replicon particles in combination with a pharmaceutically acceptable carrier are administered to the subject. Exemplary pharmaceutically acceptable carriers include, but are not limited to, sterile pyrogen-free water, sterile pyrogen-free physiological saline solution, sterile water, saline, dextrose, glycerol, ethanol, or the like and combinations thereof, as well as stabilizers, e.g. HSA or other suitable proteins and reducing sugars. Subjects which may be administered immunogenic amounts of the infectious, replication defective alphavirus particles of the present invention include human and animal (e.g., dog, cat, cattle, horse, pigs, donkey, mouse, hamster, monkeys, guinea pigs, birds, eggs) subjects. Administration may be by any suitable means, such as intraperitoneal, intramuscular, intradermal, intranasal, intravaginal, intrarectal, subcutaneous or intravenous administration.

Immunogenic compositions comprising the VRPs (which direct the expression of the sequence(s) of interest when the compositions are administered to a human or animal) or adjuvant preparations comprising VRPs (which do not express any nucleic acids encoding antigens or inhibitors) produced using the methods described herein are formulated by any of the means known. Such compositions, are typically prepared as injectables, either as liquid solutions or suspensions. Solid forms suitable for solution in, or suspension in, liquid prior to injection may also be prepared. Lyophilized preparations are also suitable.

The immunogenic (or otherwise biologically active) VRP-containing compositions are administered in a manner compatible with the dosage formulation, and in such amount as is prophylactically and/or therapeutically effective. As used herein, an immunogenic amount is an amount of the infectious virus-like particles which is sufficient to evoke an immune response in the subject to which the pharmaceutical formulation is administered. The quantity to be administered, which is generally in the range of about $10^2$ to about $10^{12}$ infectious units per mL in a dose, depends on the subject to be treated, the route by which the VRPs are administered, the immunogenicity of the expression product, the types of effector immune responses desired, and the degree of protection desired. Optionally, about $10^6$ to $10^{12}$ infectious units, or VRPs per dose, are administered to the subject. Optionally, about $10^{10}$ to $10^{12}$ infectious units, or VRPs per dose, is administered to the subject. Optionally, about $10^6$, $10^7$, or $10^8$ infectious units, or VRPs per dose, is administered to the subject. Precise amounts of the active ingredient required to be administered may depend on the judgment of the physician, veterinarian or other health practitioner and may be peculiar to each individual, but such a determination is within the skill of such a practitioner.

The pharmaceutical composition is given in a single dose or multiple dose schedule. A multiple dose schedule is one in which a primary course may include 1 to 10 or more separate doses, followed by other doses administered at subsequent time intervals as required to maintain and or reinforce the immune response, e.g., weekly or at 1 to 4 months for a second dose, and if needed, a subsequent dose(s) after several months/years.

As discussed above, it is contemplated that other viral-based vector systems including, for example, retroviral (e.g. murine stem cell virus), lentiviral, herpesviral and adenoviral vector systems, can be modified as described herein for alphaviruses. In these systems, a critical function of the parental virus has been removed to set up a replication/propagation deficient vector system. The critical function is provided in trans during production of the virus-like particles, and the use of miRNA targets as described herein allows significant reduction in the probability of regeneration of functional, replication-competent virus in the recipient. As used herein, the phrase vector system refers to the components necessary to create virus-like particles. For example, a vector system comprises a vector, which is packaged into the virus-like particles and one or more additional nucleic acids that encode the genes necessary for production of the virus-like particle. Optionally, the vector also comprises one or more genes necessary for production of the virus-like particle. As used herein, the critical function can be a gene necessary for production of a virus-like particle such as a structural gene (i.e., a gene encoding an envelope protein such as a VSVG protein) or a gene necessary for replication of the virus (i.e., a gene encoding a polymerase protein such as Adenovirus E1a protein).

Thus, provided is a vector system comprising a helper nucleic acid comprising (i) at least one microRNA target sequence of an endogenous, cellular microRNA and (ii) a nucleic acid encoding a viral structural protein, wherein the target sequence is located in the 3' UTR, 5' UTR or translated region of the viral structural protein, and a vector. Also provided are vector systems comprising a helper nucleic acid comprising (i) at least one microRNA target sequence of an endogenous, cellular microRNA, and (ii) a nucleic acid encoding a viral protein essential for replication of the virus, and a vector. The helper nucleic acid and/or vector is DNA or RNA. Optionally, the helper nucleic acid is located in a packaging cell. Optionally, the helper nucleic acid is located on a plasmid in the packaging cell. As discussed above for replicons, optionally the vector encodes a polypeptide, an immunostimulatory molecule, an immunogenic polypeptide or a therapeutic product.

Optionally, the vector system is a single-cycle vector system or a limited-cycle vector system. As used herein, the term single-cycle vector system refers to a vector system that produces viral particles that are infectious but propagation-defective, i.e., the virus cannot propagate beyond the host cell into which the particles are initially infected. As used herein, the term limited-cycle vector system refers to a vector system that produces viral particles that are infectious and have limited propagation capacity. For example, viral particles produced from limited-cycle vector systems can propagate beyond the host cell into which the particles are initially infected, but are not virulent (i.e., the viral particles themselves are not pathogenic).

As discussed above, the microRNA target sequence of the helper nucleic acid is located, for example, in the translated region, the 5' UTR, or the 3' UTR of the nucleic acid encoding the structural protein. Optionally, at least one target sequence is located in the 3' UTR of the nucleic acid encoding a structural protein and at least one target sequence is located in the 5' UTR of the nucleic acid encoding a structural protein or viral protein essential for replication of the virus. Preferably, the microRNA target sequence is located in the 3'UTR of the nucleic acid encoding the structural protein or viral protein essential for replication and/or propagation of the virus.

Optionally, the provided vector systems further comprise a second helper nucleic acid comprising at least one microRNA target sequence of an endogenous, cellular microRNA and a nucleic acid encoding viral structural protein(s) or encoding viral protein(s) essential for replication and/or propagation of the virus. The first and second helper nucleic acids comprise the same or different microRNA target sequences.

Viral structural proteins include, but are not limited to lentivirus, herpesvirus, rhabdovirus, picornavirus, murine or feline leukemia virus, adenovirus and flavivirus structural proteins. Examples of lentivirus structural proteins include human immunodeficiency virus (HIV) structural proteins. Examples of herpesvirus (HSV) structural proteins include HSV-1 structural proteins. Examples of rhabdovirus structural proteins include vesicular stomatitis virus (VSV) structural proteins.

Viral proteins essential for replication and/or propagation (e.g., nonstructural proteins) are selected from the group consisting of a lentivirus, herpesvirus, rhabdovirus, picornavirus, murine or feline leukemia virus, adenovirus and a flavivirus protein essential for replication. Examples of lentivirus proteins essential for replication proteins include human immunodeficiency virus (HIV) proteins essential for replication. Examples of herpesvirus (HSV) proteins essential for replication include HSV-1 proteins essential for replication. Examples of rhabdovirus proteins essential for replication include vesicular stomatitis virus (VSV) proteins essential for replication.

As an example, lentiviral vector packaging systems provide separate packaging constructs for gag/pol and env, and typically employ a heterologous or functionally modified envelope protein for safety reasons. See, e.g., Miller and Buttimore, Mol. Cell. Biol. 6(8):2895-902 (1986). As used herein, the term packaging construct refers to a construct comprising a gene encoding a protein that is necessary for packaging of the virus. This differs from the packaging signal, which is located on the nucleic acid that is to be packaged into the virus. These modifications minimize the homology between the packaging genome and the viral vector so that the ability of the vector to form recombinants is reduced (see, e.g., Miller and Rosman, BioTechniques 7(9):980-90 (1989)). For other lentiviral vector systems, the accessory genes, vif, vpr, vpu and nef, are deleted or inactivated and the packaging functions are divided into two genomes: one genome expresses the gag and pol gene products, and the other genome expresses the env gene product (see, e.g., Bosselman et al., Mol. Cell. Biol. 7(5): 1797-806 (1987); Markowitz et al., J. Virol. 62(4):1120-4 (1988); Danos and Mulligan, Proc. Natl. Acad. Sci. USA 85:6460-6464 (1988)). Thus, microRNA targets can be positioned in the translated or untranslated region of the nucleic acids encoding these genes to prevent formation of replication competent virus.

Flavivirus-based replicon systems have been described (Khromykh et al., J. Virol. 72:5967-77 (1998); Scholle et al., J. Virol. 78:11605-14 (2004); and Yoshii et al., Vaccine 23:3946-56 (2005)). Flavivirus-based replicon systems have the structural protein gene coding region deleted rendering the replicon vector incapable of producing new progeny in cells that do not supply them in trans. As described for alphavirus vectors, introduction of miRNA target sequences into the 5' and/or 3' UTR of the transcripts that provide the flavivirus structural proteins targets those RNAs for destruction by cellular miRNAs when miRNA inhibitors are not present. If, during production of flavivirus replicon particles in packaging cells, a recombination event restored the structural protein coding region into the replicon vector, the subsequent particle would still be propagation defective. This is because, when introduced into other cells, the structural protein RNA would be targeted for degradation by the cellular miRNA degradation machinery.

Propagation-deficient replicon systems based on Rhabdoviruses (e.g., VSV), Paramyxoviruses (e.g., Sendai virus) and Picornaviruses (e.g., Polio) require that structural proteins be provided in trans to package virus-like particles that can subsequently be used to infect target cells (Matthias et al., Cell 90:849-57 (1997); Kapadia et al., Virology 376: 165-72 (2008); Ansardi et. al., J. Virol. 67:3684-90 (1993); and Inoue et al., J. Gene. Med. 6:1069-81 (2004)). The helper function (e.g., the structural proteins) can be provided by plasmid DNAs, other recombinant vectors (e.g., vaccinia virus) or cells modified to express helper functions (e.g., structural proteins) either transiently or constitutively. The helper structural protein mRNA transcripts can potentially recombine into the replicon vector systems, thus reconstituting a propagation/replication competent viral genome. Engineering miRNA targets into the helper genes for these vector systems would prevent formation of a propagation/replication competent viral genome. This is because the structural protein mRNA is targeted for degradation by the cellular miRNA degradation machinery.

Adenoviral vectors have been developed that are replication-defective. This has been accomplished by removal of the genes from the vector that are essential for the virus to replicate. Replication-defective adenovirus vectors arc produced in packaging cell lines that provide the elements required for replication and packaging of the defective adenovirus genome into virus-like particles. However, adenovirus vectors may become replication competent if DNA-DNA recombination events in the packaging cell line occur. By engineering miRNA target sequences into the genes essential for replication of the adenovirus, recombinant adenoviruses would not be replication competent since the mRNAs of the genes essential for replication are targeted for degradation by the miRNA degradation machinery. In other words, if DNA recombination events occur generating a full complement of adenovirus genes, the essential replication and packaging proteins would not be expressed due to miRNA targeted degradation of those mRNA transcripts in subsequently infected cells.

The same strategy described above will work for replication-incompetent or disabled infectious single cycle (DISC) herpes simplex virus type 1 (HSV-1)-based vaccine vectors (Farrell et al., J. Virol. 68:927-32 (1994); and Weir and Elkins, Proc. Natl. Acad. Sci. USA 90:9140-4 (1993)). These HSV-1 vectors have deletions in their viral genomes of essential genes (e.g., 1CP4 gene and gH gene) that render them replication or propagation-incompetent. HSV-1 virus-like particles can be produced if the proteins encoded by the deleted portions of the genome are provided in trans by cell lines that express them in either a continuous or inducible manner. Placing miRNA targets into the essential genes expressed within the packaging cells would target those mRNAs for degradation in subsequently infected cells. In other words, if DNA-DNA recombination occurs with the essential genes expressed by the packaging cell and the HSV-1 vectors, the essential genes would not be expressed in subsequently infected cells due to miRNA targeted degradation of the essential gene mRNA transcripts.

Further provided are kits comprising one or more of any of the helper nucleic acids described herein. As an example, the kit comprises a helper nucleic acid comprising at least one microRNA target sequence of an endogenous, cellular microRNA; and a nucleic acid encoding an alphavirus structural protein, wherein the microRNA target sequence is located in a region of the nucleic acid encoding the alphavirus structural protein. For example, the microRNA target sequence can be in the translated or untranslated region of the alphavirus structural protein. Optionally, the kits further comprise any of the replicons described herein. Optionally, the kits further comprise any of the cells described herein. Optionally, the kit comprises a population of alphavirus-like replicon particles (ARPs). The ARPs can, for example, comprise a first subset of particles comprising a replicon and a second subset of particles comprising any of the helper nucleic acids or fragments thereof described herein and a replicon. Optionally, the kits further comprise directions for making virus-like replicon particles. The directions can, for example, include any of the methods of making virus-like replicon particles described herein.

Disclosed are materials, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutations of these compounds may not be explicitly disclosed, each is specifically contemplated and described herein. For example, if a method is disclosed and discussed and a number of modifications that can be made to a number of molecules including the method are discussed, each and every combination and permutation of the method, and the modifications that are possible are specifically contemplated unless specifically indicated to the contrary. Likewise, any subset or combination of these is also specifically contemplated and disclosed. This concept applies to all aspects of this disclosure including, but not limited to, steps in methods using the disclosed compositions. Thus, if there are a variety of additional steps that can be performed, it is understood that each of these additional steps can be performed with any specific method steps or combination of method steps of the disclosed methods, and that each such combination or subset of combinations is specifically contemplated and should be considered disclosed.

Publications cited herein and the material for which they are cited are hereby specifically incorporated by reference in their entireties.

EXAMPLES

Materials and Methods

Construction of helpers containing 3' plus-strand microRNA (miRNA) target sequences. This set of helpers was designed to have the target for cellular miRNA action be present in the 3' UTR region of the positive-strand RNA message produced during helper replication. The helper design is schematically depicted in FIG. 1. A DNA fragment was synthesized that coded for the reverse complement (RC) sequence of six different microRNAs (miRNA) aligned in tandem (5'-gcatgcaactatacaacctactacctcaacacagtcgaaggtctcagggacttcagttatcacagtactgtagatatccccct atcacgattagcattaaactacctgcactgtaagcactttgtcagttttgcatagatttgcacagtttaaac-3' (SEQ ID NO:17). The miRNA target sequences were specific for let-7 (RC1; 5'-aactatacaacctactacctca-3' (SEQ ID NO:11)), lin-4 (RC2; 5'-acacagtcgaaggtctcaggga-3' (SEQ ID NO:12)), miR-101(RC3; 5'-cttcagttatcacagtactgta-3' (SEQ ID NO:13)), miR155 (RC4; 5'-cccctatcacgattagcattaa-3' (SEQ ID NO:14)), miR-17 (RC5; 5'-actacctgcactgtaagcactttg-3' (SEQ ID NO:15)), and miR-19 (RC6; 5'-tcagttttgcatagatttgcaca-3' (SEQ ID NO:16)). A unique SphI restriction site was engineered before the 5' most miRNA target sequence (let-7), a unique EcoRV restriction site was engineered between the third (miR-101) and fourth (miR-155) miRNA target sequences and a unique PmeI restriction site was engineered after the last miRNA (miR-19) target sequence. In addition, immediately downstream of the miRNA target sequences 63 base pairs (bp) corresponding to the Venezuelan equine encephalitis (VEE) virus 3' noncoding region (NCR), 55 bp corresponding to a poly (A) stretch and 8 bp corresponding to a unique NotI restriction site were also synthesized. The 281 bp fragment was digested with SphI and NotI restriction enzymes and then ligated into capsid (dHcap6-mut1 (W-stop)) and GP (dHgp6-mut1) helper plasmids linearized with the same two enzymes. The resulting helper plasmids were designated dHcap6-mut1(W-stop)RC1-6 and dHgp6-mut1-RC1-6. The miRNA targets were represented by the identifiers 1 through 6 and are numbered in the order listed above (let-7=1, lin-4=2, miR-101=3, miR155=4, miR-17, =5, and miR-19=6).

Helper plasmids coding for the first three (let-7, lin-4 and miR-101; 5'-gcatgcaactatacaacctactacctcaacacagtc-gaaggtctcagggacttcagttatcacagtactgta-3' (SEQ ID NO:18)) or the last three (miR-155, miR-17 and miR-19; 5'-cccctat-cacgattagcattaaactacctgcactgtaagcactttgtcagttttgcatagatttg-cacagtttaaac-3' (SEQ ID NO:19)) miRNA target sequences were constructed. Helpers with the first three miRNA targets (1-3) were constructed by digesting dHcap6-mut1(W-stop) RC1-6 and dHgp6-mut1-RC1-6 helpers with EcoRV and NotI restriction enzymes to remove the miRNA targets 4-6 and the VEE 3' NCR. The VEE 3' NCR was replaced by digesting dHcap6-mut1 (W-stop) with SphI, treating the DNA with T4 DNA polymerase to produce a blunt end and then digesting the DNA further with NotI to release a 122 bp fragment. The 122 bp fragment was then ligated into the EcoRV/NotI digested capsid and gp helpers above, generating helpers designated dHcap6-mut1(W-stop)RC1-3 and dHgp6-mut1-RC1-3.

Helpers coding for the last three miRNA targets (4-6) were constructed by digesting dHcap6-mut1(W-stop)RC1-6 and dHgp6-mut1-RC1-6 helpers with EcoRV and RsrII restriction enzymes to remove the capsid or gp genes and the miRNA targets 1-3. The capsid and gp genes were replaced by digesting dHcap6-mut1 (W-stop) or dHgp6-mut1 DNA with SphI, treating the DNAs with T4 DNA polymerase to produce a blunt end and then digesting the DNA further with RsrII to release the VEE structural protein genes. The RsrII/SphI(T4) capsid and gp gene fragments were gel purified and then ligated into the RsrII/EcoRV digested miRNA 4-6 plasmid backbones described above, generating helpers designated dHcap6-mut1(W-stop)RC4-6 and dHgp6-mut1-RC4-6.

Helpers coding for either individual miRNA targets or combinations of two miRNA targets were also constructed. A similar approach was used to generate the miRNA target containing helpers as was used to produce the 1-3 and 4-6 miRNA target helpers described above. PCR primers were designed that would amplify the individual miRNA targets as well as the two miRNA target combinations. The primers and DNA templates used to amplify the miRNA targets are summarized in Table 1. The miRNA targets were cloned into the dHcap6-mut1 (W-stop) or dHgp6-mut1 helpers as described above either as RsrII/PmeI fragments (miRNA targets 1, 1-2, 3, 4, 4-5, and 5) or SphI/NotI fragments (miRNA targets 6 and 5-6). All miRNA helper constructs were sequenced to ensure that no errors were introduced during PCR amplification.

TABLE 1

Primers and DNA templates.

| miRNA target | Forward primer | Reverse primer | miRNA PCR template |
|---|---|---|---|
| 1 | T7 (5'-TTAATACGACTC ACTATAG-3' (SEQ ID NO: 1)) | let-7 RC (PmeI) R (5'-GGGGTTTAAA CTGAGGTAGTAGGTTGTATAGTT-3' (SEQ ID NO: 6)) | capsid or gp miRNA 1-3 helper |
| 1-2 | T7 (SEQ ID NO: 1) | lin-4 RC (PmeI) R (5'-GGGGTTTAAA CTCCCTGAGACCTTCGACTGTGT-3' (SEQ ID NO: 7)) | capsid or gp miRNA 1-3 helper |
| 3 | miR-101 RC (SphI) F (5'-TTTGCATGCCTTCAGTT ATCACAGTACTGTA-3' (SEQ ID NO: 2)) | 3-1.1pr1 (5'-TAAGAGCCGCGAGCG ATCCT-3' (SEQ ID NO: 8)) | capsid or gp miRNA 1-3 helper |
| 2-3 | lin-4 RC (SphI) F (5'-TTTGCATGCACACAGTCGA AGGTCTCAGGGA-3' (SEQ ID NO: 3)) | 3-1.1pr1 (SEQ ID NO: 8) | capsid or gp miRNA 1-3 helper |
| 2 | T7 (SEQ ID NO: 1) | lin-4 RC (PmeI) R (SEQ ID NO: 7) | capsid or gp miRNA 2-3 helper |
| 4 | T7 (SEQ ID NO: 1) | miR-155 RC (PmeI) R (5'-GGGTTTAA ACTTAATGCTAATCGTGATAGGG G-3' (SEQ ID NO: 9)) | capsid or gp miRNA 4-6 helper |
| 4-5 | T7 (SEQ ID NO: 1) | miR-17 RC (PmeI) R (5'-GGGTTTAA ACCAAAGTGCTTACAGTGCAGGT AGT-3' (SEQ ID NO: 10)) | capsid or gp miRNA 4-6 helper |

TABLE 1-continued

Primers and DNA templates.

| miRNA target | Forward primer | Reverse primer | miRNA PCR template |
|---|---|---|---|
| 5 | T7 (SEQ ID NO: 1) | miR-17 RC (PmeI) R (SEQ ID NO: 10) | capsid or gp miRNA 5-6 helper |
| 5-6 | miR-17 RC (SphI) F (5'-CATGCATGCACTACCTGCA CTGTAAGCACTTTG-3' (SEQ ID NO: 4)) | 3-1.1pr1 (SEQ ID NO: 8) | capsid or gp miRNA 4-6 helper |
| 6 | miR-19 RC (SphI) F (5'-CATGCATGCTCAGTTTTGC ATAGATTTGCACA-3' (SEQ ID NO: 5)) | 3-1.1pr1 (SEQ ID NO: 8) | capsid or gp miRNA 4-6 helper |

Helpers coding for individual miRNA targets repeated six times, on the positive-strand RNA message produced during helper replication, were also constructed. Six copies of each individual miRNA target were chosen because that is the total number of miRNA targets tested in the RC1-6 constructs and the length of the inserted sequence in the 3' NCR would also be maintained in the new constructs relative to the RC1-6 constructs. DNA fragments were de-novo synthesized (BlueHeron Biotechnology, Inc.; Bothell, Wash.) that coded for the RC sequence of six copies of each individual miRNA aligned in tandem. The identifiers for the respective 6mer miRNA fragments were: RC1x6, RC2x6, RC3x6, RC4x6, RC5x6 and RC6x6. A unique SphI restriction site was engineered before the first miRNA target sequence, a unique EcoRV restriction site was engineered between the third and fourth copy of the miRNA target sequence and a unique PmeI restriction site was engineered after the last copy of the miRNA target sequence. The respective miRNAx6 sequence fragments were digested with SphI and PmeI restriction enzymes and then ligated individually in place of the miRNA1-6 sequence fragment found in dHcap6-mut1(W-stop)RC1-6 or dHgp6-mut1-RC1-6, by digesting the helpers with SphI and PmeI restriction enzymes. The resulting capsid helpers were designated dHcap6-mut1(W-stop)RC1x6, dHcap6-mut1(W-stop) RC2x6, dHcap6-mut 1(W-stop)RC3x6, dHcap6-mut1(W-stop)RC4x6, dHcap6-mut1(W-stop)RC5x6 and dHcap6-mut1(W-stop)RC6x6. The resulting GP helper were designated dHgp6-mut1-RC1x6, dHgp6-mut1-RC2x6, dHgp6-mut1-RC3x6, dHgp6-mut1-RC4x6, dHgp6-mut1-RC5x6 and dHgp6-mut1-RC6x6.

Helpers coding for three copies of a miRNA target sequence (e.g., RC1x3) were also constructed. This was accomplished in two ways. For miRNA targets RC1-RC6, helpers containing three copies were produced by digesting the capsid and gp helpers that contained six copies of an individual miRNA target (e.g., RC1x6) with restriction enzymes EcoRV and PmeI. This digestion releases a 75 bp fragment removing 3 of the 6 miRNA target copies from each helper. The EcoRV/PmeI digested DNAs were then relegated on themselves generating capsid and gp helpers with 3 miRNA targets in their 3' UTRs. Six additional miRNA target sequences were identified (RC7-RC12) that were known to have more cell-type or tissue-specific activity than the more broadly active targets represented by RC1-RC6. The miRNA targets for RC7-RC12 are as follows: RC7=miR-143 (5'-gagctacagtgcttcatctca-3' (SEQ ID NO:20)); RC8=miR-30b (5'-agctgagtgtaggatgtttaca-3' (SEQ ID NO:21)); RC9=miR-181 (5'-actcaccgacagcgttgaatgtt-3' (SEQ ID NO:22)); RC10=miR-124 (5'-ggcattcaccgcgtgcctta-3' (SEQ ID NO:23)); RC11=miR-1 (5'-atacatacttctttacattcca-3' (SEQ ID NO:24)); and RC12=miR-133a (5'-cagctggttgaaggggaccaaa-3' (SEQ ID NO:25)). Capsid helpers that contained target sequences consisting of three copies of each specific miRNA target sequence were produced in the following manner. Reverse PCR primers that coded for each miRNA target sequence in triplicate (e.g., RC7x3 R (5'-GCGTTTAAACTGAGATGAAGCACTGTAGCTCTGAGATGAAGCACTGTAGC TCTGAGATGAAGCACTGTAGCTCGCATGCTTACCATTGCTCGCAGTTCTCC GGAGTATACTTCACGGTAACTCCC-3' (SEQ ID NO:26)); RC8x3 R (5'-GCGTTTAAACTGTAAACATCCTACACTCAGCTTGTAAACATCCTACACTCA GCTTGTAAACATCCTACACTCAGCTGCATGCTTACCATTGCTCGCAGTTCT CCGGAGTATACTTCACGGTAACTCCC-3' (SEQ ID NO:27)); RC9x3 R (5'-GCGTTTAAACAACATTCAACGCTGTCGGTGAGTAACATTCAACGCTGTCG GTGAGTAACATTCAACGCTGTCGGTGAGTGCATGCTTACCATTGCTCGCAG TTCTCCGGAGTATACTTCACGGTAACTCCC-3' (SEQ ID NO:28)); RC10x3 R (5'-GCGTTTAAACTAAGGCACGCGGTGAATGCCTAAGGCACGCGGTGAATGCC TAAGGCACGCGGTGAATGCCGCATGCTTACCATTGCTCGCAGTTCTCCGG AGTATACTTCACGGTAACTCCC-3' (SEQ ID NO:29)); RC11x3 R (5'-GCGTTTAAACTGGAATGTAAAGAAGTATGTATTGGAATGTAAAGAAGTAT GTATTGGAATGTAAAGAAGTATGTATGCATGCTTACCATTGCTCGCAGTTC TCCGGAGTATACTTCACGGTAACTCCC-3' (SEQ ID NO:30)); and RC12x3 R (5'-GCGTTTAAACTTTGGTCCCCTTCAACCAGCTGTTTGGTCCCCTTCAACCAG CTGTTTGGTCCCCTTCAACCAGCTGGCATGCTTACCATTGCTCGCAGTTCT CCGGAGTATACTTCACGGTAACTCCC-3' (SEQ ID NO:31))) and a region of homologous capsid helper sequence were engineered. These reverse primers were then combined with a capsid gene specific forward primer (capsid (RsrII) F; 5'-CCTCGGACCGACCATGTTCCCGTTCCAGCCAATG-3' (SEQ ID NO:32)) to amplify a PCR product that coded for the entire capsid gene, three copies of each miRNA target sequence (e.g., RC7x3) and the VEE 3' UTR sequence. These capsid-RCx3 PCR products were then digested with RsrII and PmeI restriction enzymes and used to replace the RsrII/PmeI region of dHcap6-mut1(W-stop)

RC1-6 DNA, generating dHcap6-mut1(W-stop)RC7x3, dHcap6-mut1(W-stop)RC8x3, dHcap6-mut1(W-stop)RC9x3, dHcap6-mut1(W-stop)RC10x3, dHcap6-mut1(W-stop)RC11x3 and dHcap6-mut1(W-stop)RC12x3. The entire capsid and miRNA target sequence regions were sequenced to ensure no errors were introduced during PCR amplification. The RC7-RC12 target sequences were engineered with a unique 5' SphI restriction site and a unique 3' NotI restriction site. Each of the miRNA targeted capsid helper DNAs (RC7x3-RC12x3) were digested with SphI and NotI restriction enzymes to release the ~190 bp trimer miRNA target sequences. Each ~190 bp trimer miRNA target (SphI/NotI) fragment was then ligated into dHgp6-mut1 DNA linearized with SphI and NotI restriction enzymes to produce RC7x3-RC12x3 miRNA targeted GP helper constructs: dHgp6-mut1-RC7x3; dHgp6-mut1-RC8x3; dHgp6-mut1-RC9x3; dHgp6-mut1-RC10x3; dHgp6-mut1-RC11x3; and dHgp6-mut1-RC12x3.

Construction of helpers containing 3' minus-strand miRNA target sequences. Additional helpers were constructed that provided the target sequences for cellular miRNA action on the minus-strand replicative intermediate RNA. A forward primer specific to the miR-19 (miR-19 (SphI) F (SEQ ID NO:5)) sequence was engineered to code for a unique SphI restriction site. A reverse primer specific for let-7 (let-7 RC (PmeI) R (SEQ ID NO:6)) was engineered with a unique PmeI restriction site. PCR amplification with these primers resulted in a 155 bp product. The PCR product was digested with SphI and PmeI restriction enzymes and ligated into SphI and PmeI linearized dHcap6-mut1(W-stop)RC1-6 and dHgp6-mut1-RC1-6 DNA. The resultant helpers (dHcap6-mut1(W-stop)RC1-6-NS and dHgp6-mut1-RC1-6-NS) generated the miRNA target sequences on the minus-strand replicative intermediate RNA.

Construction of helpers containing 5' plus and minus-strand miRNA target sequences. Helpers were constructed that contain the miRNA target sequences (1-6) in the 5' non-coding region (NCR) of these RNAs such that the targets would be present on either the plus or minus-strand RNA (FIG. 2). A unique RsrII restriction site was present immediately 5' to the structural gene in the dHcap6-mut1 (W-stop) helper plasmid and it was used to generate these constructs. Forward (let-7 RC (RsrII) F (5'-TTTCGGTCCGAACTATACAACCTAC-3' (SEQ ID NO:34))) and reverse (miR-19 RC (RsrII) R (5'-TTTCGGACCGTGTGCAAATCTATGC-3') (SEQ ID NO:33)) primers engineered to code for RsrII restriction sites were designed to amplify the miRNA 1-6 cassette. The 155 bp PCR product was digested with RsrII restriction enzyme and ligated into dHcap6-mut1(W-stop) DNA linearized with RsrII enzyme. The orientation of the miRNA 1-6 PCR product was determined by sequence analysis and clones with the miRNA 1-6 fragment in only the reverse orientation (minus-strand RNA) were obtained. These clones were designated, dHcap6-mut1 (W-stop)-5'RC1-6-NS. To generate helpers with the miRNA 1-6 targets 5' of the structural genes on the plus-stranded RNA additional steps were required. First, the 5' RsrII restriction site introduced when the minus-strand construct was produced was mutated to a unique BglII restriction site (primer: RsrII→Bgl II mut; (5'-GACATTGGAAGATCTTGTGCAAATCTATG-3' (SEQ ID NO:35))) using site directed mutagenesis (Stratagene; Lo Jolla, Calif.), resulting in a helper designated, dHcap6-mut1(W-stop)-5'BglII-RC1-6-NS. Next, primers were engineered to amplify the plus-strand miRNA 1-6 target sequence with a 5' BglII restriction site and a 3' RsrII restriction site (let-7 RC (Bgl II) F (5'-GGAGATCTCGAACTATACAACCTAC-3' (SEQ ID NO:36)); and miR-19 RC (RsrII) R (SEQ ID NO:33)). The 147 bp product of amplification was digested with BglII and RsrII restriction enzymes and gel purified. The dHcap6-mut1 (W-stop)-5'BglII-RC1-6-NS DNA was then digested with BglII and RsrII to remove the minus-stand oriented miRNA targets and the plus-strand miRNA target fragment cloned in its place. The helper that expressed the miRNA targets on the plus-strand RNA was designated dHcap6-mut1(W-stop)-5'RC1-6.

Construction of helpers containing 5' and 3' plus-strand miRNA target sequences. A capsid helper was constructed that coded for miRNA1-6 targets in both the 5' and 3' UTR positions on the plus-strand RNA template (FIG. 3). To accomplish this the dHcap6-mut1(W-stop)-5'RC1-6 helper DNA was digested with SphI and NotI restriction enzymes to release the wild type 3' UTR sequence. The dHcap6-mut1 (W-stop)RC1-6 helper DNA was digested with SphI and NotI restriction enzymes and the 3' UTR fragment (ca 270 bp) containing the miRNA1-6 targets was gel purified. The linearized dHcap6-mut1(W-stop)-5'RC1-6 DNA was ligated with the 3' UTR miRNA1-6 fragment and the resulting helper was designated, dHcap6-mut1(W-stop)-5' & 3'RC1-6 DNA.

Construction of miRNA targeted, cleavage deficient, capsid helpers. Site directed mutagenesis was used to introduce a glycine (G) residue in place of the histidine (H) residue at amino acid 152 (m152) of the capsid protein in miRNA targeted capsid helper constructs (primers: Cap152 G F (5'-GTTATTCAGGCCGATGGGTGTGGAAGGCAAGATCG-3' (SEQ ID NO:37)); and Cap152 G R (5'-CGATCTTGCCTTCCACACCCATCGGCCTGAATAAC-3' (SEQ ID NO:38))). The m152 capsid gene was sequenced to ensure that no other mutations were introduced during mutagenesis. In order to demonstrate that the m152 H→G change ablates the autoprotease function of the capsid protein, the m152 mutation was introduced into the capsid coding sequence of pHCMV-Vsp (see U.S. Pat. No. 7,045,335 to Smith et al.). The pHCMV-Vsp DNA codes for a Cytomegalovirus (CMV) immediate early promoter that controls the DNA-dependent RNA transcription of the complete VEE structural protein coding region (capsid-E3-E2-6K-E1). Site directed mutagenesis was used to introduce the m152 mutation into the capsid protein of the pHCMV-Vsp construct, generating pHCMV-Vsp(m152). The entire VEE structural gene coding region was sequenced in pHCMV-Vsp(m152) to ensure that no other mutations were introduced during mutagenesis.

Construction of helpers containing 9 miRNA target sequences. Helpers were constructed that contain one copy of 9 different miRNA target sequences in the 3' non-coding region (NCR) such that the targets would be present on the plus strand RNA. The following miRNA targets were combined on the capsid and glycoprotein helpers: RC1 (Let-7), RC4 (miR-101), RC5 (miR-17), RC9 (miR-181), RC2 (miR-125), RC3 (miR-101), RC10 (miR-124), RC7 (miR-143) and RC12 (miR-133a). DNA coding for the 9 miRNA targets was de-novo synthesized with unique SphI and PmeI restriction sites engineered at the 5' and 3' ends, respectively. Unique SphI and PmeI restriction sites present immediately 3' to the structural gene in both helper plasmids were used to generate these constructs. The helper plasmids were linearized with SphI and PmeI and the approximately 200 bp de novo synthesized 9 miRNA target fragment was cloned in at these sites. These 9 miRNA target-containing helper plasmids were identified as (dHcap6-mut1(W-stop)mi and dHgp6-mut1 mi, respectively): In addition, the ~200 bp 9 miRNA target fragment was cloned into the capsid helper modified to code for the 152 capsid cleavage mutation resulting in generation of the helper dHcap6-mut1(W-stop) mi152.

Construction of miRNA-targeted replicon vectors. Replicon vectors expressing the CAT reporter gene were constructed that contained miRNA targets located in the 3' UTR. The miRNA targets were cloned into a CAT replicon vector as tandem single copies (RC1-6), as six tandem copies of the same miRNA target (RC1x6, RC2x6, RC3x6, RC4x6, RC5x6 and RC6x6) or as three tandem copies of the same miRNA target (RC7x3, RC8x3, RC9x3, RC10x3, RC11x3 and RC12x3). The replicon vector, pERK/342/EMCV/CAT, used for all constructions has been described previously (Karnrud et al., Virology 360(2):376-87 (2007)). The miRNA target sequences for RC1x6-RC6x6 and RC7x3-RC12x3 were digested from their respective dHcap6-mut1 (W-stop)RC helpers (described above) using restriction enzymes SphI and NotI. The miRNA target fragments released after digestion were then isolated and ligated into the pERK/342/EMCV/CAT replicon vector linearized with the same restriction enzymes. The resulting replicon vectors were designated pERK/342/EMCV/CAT-RC1-6, pERK/342/EMCV/CAT-RC1x6, pERK/342/EMCV/CAT-RC2x6, pERK/342/EMCV/CAT-RC3x6, pERK/342/EMCV/CAT-RC4x6, pERK/342/EMCV/CAT-RC5x6, pERK/342/EMCV/CAT-RC6x6, pERK/342/EMCV/CAT-RC7x3, pERK/342/EMCV/CAT-RC8x3, pERK/342/EMCV/CAT-RC9x3, pERK/342/EMCV/CAT-RC10x3, pERK/342/EMCV/CAT-RC11x3 and pERK/342/EMCV/CAT-RC12x3.

A replicon vector expressing the influenza A/Wisconsin HA gene, pERK/342/EV71/A(Wis)/HA, was produced as described previously (Kamrud et al., Virology 360(2):376-87 (2007)). The RC1-6 miRNA sequence was cloned into the 3' UTR of the pERK/342/EV71/A(Wis)/HA replicon as described above for the miRNA targeted CAT replicons, generating a replicon designated pERK/342/EV71/A(Wis)/HA-RC1-6.

RNA transcription, electroporation and Venezuelan equine encephalitis virus replicon particle (VEE RP) production. Capped replicon and helper RNAs were in-vitro transcribed using a T7 RiboMax™ kit (Promega; Madison, Wis.) following the manufactures instructions. RNAs were purified using RNeasy™ purification columns (Qiagen; Valencia, Calif.) following the manufacturer's instructions. The procedures used for producing VEE RP vaccines were based on modifications of published methods (Pushko et al., Virology 239(2):389-401 (1997)). Vero cells ($8 \times 10^7$) suspended in 0.6 ml PBS (GIBCO) were electroporated with 30 µg of replicon RNA, 20 µg of capsid helper RNA and 60 µg of GP helper RNA using a Bio-Rad Gene Pulser (Bio-Rad; Hercules, Calif.). When miRNA-targeted helpers or replicons were used to generate VEE RP, miRNA inhibitors were included in the electroporation. The miRNA inhibitors were 2'-O-methyl modified RNA oligonucleotides with the reverse complement (RC) sequence to the target miRNA (Eurogentec; San Diego, Calif.). Cells were pulsed four times with the electroporator set at 580 volts and 25 µF. Electroporated cell suspensions were seeded into roller bottles containing serum-free medium and incubated at 37° C. in 5% $CO_2$ for 16-24 hours. VEE RP were harvested from culture fluids and the infectious titer of the VEE RP preparation was measured by antigen-specific IFA and tested in a cytopathic effect (CPE) assay to assure the absence of detectable replication-competent virus. VEE RP generated with a replicon vector containing miRNA-targets were titrated on Vero cells electroporated with miRNA inhibitors to allow the replicon vector to replicate unhindered by the cellular miRNAs. VEE RP were formulated with human serum albumin (1%) and stored at −80° C. until used.

IFA and CAT ELISA. CAT expression was quantified by ELISA using miRNA-targeted, CAT replicon VEE RP infected cell lysates and a commercially available CAT ELISA kit (Boehringer Mannheim; Indianapolis, Ind.) following the manufacturer's instructions. All cell types analyzed were infected with VEE RP at a multiplicity of infection (MOI)=1 based on genome copies rather than infectious units (IU). The cell lysates were produced 18 hours post infection and total protein concentration was determined for each sample using a BCA protein kit (Pierce; Rockford, Ill.). CAT expression was also detected by immunofluorescence assay (IFA) using a rabbit anti-CAT antibody (Cortex Biochem Inc.; San Leandro, Calif.). Cells transfected with replicon RNA and helper RNAs were also analyzed by IFA using goat anti-nsP2 antibody (for replicon), goat anti-capsid antibody and goat anti-GP antibody. All cells for IFA analysis were fixed with methanol and inspected using a Nikon Eclipse TE300 ultraviolet fluorescence microscope.

Northern analysis. Northern analysis was carried out on total cellular RNA collected from VEE RP infected cells. Total cellular RNA was collected from the cells 16 hours post infection using SV Total RNA Isolation columns (Promega) following the manufacturers instructions. The RNA was quantified by UV absorption and 3 µg of each were run on 1% glyoxal agarose gels before being transferred to a BrightStar-Plus membrane (Ambion; Austin, Tex.) by passive transfer. The RNA was UV crosslinked to the membrane, blocked with UltraHyb (Ambion) solution for 1 hour at 45° C., and probed overnight with UltraHyb solution containing biotinylated RNA probes specific for nsP2, capsid or GP genes at 65° C. After overnight hybridization the blot was processed for chemiluminescent RNA detection using a BrightStar BioDetect kit (Ambion) following the manufacturer's instructions and visualization after exposure to autoradiograph film (Kodak; Rochester, N.Y.).

Quantitative reverse transcription PCR (RTqPCR) analysis of VEE RP. To determine the number of genome equivalents present in each miRNA-targeted CAT replicon VEE RP preparation, a standard one-step RT-qPCR protocol was performed on an Applied Biosystems 7500 Fast Real Time PCR System sequence detection system (Applied Biosystems; Foster City, Calif.). Amplification was detected by means of a fluorogenic probe designed to anneal to a region of the nsP2 gene on the replicon between the two primers. A 5' reporter dye (6-FAM) and a 3' quencher dye (BHQ-1) were attached to the probe. Proximity of the reporter and quencher dyes resulted in the suppression of reporter fluorescence prior to amplification. Upon successful amplification of the target region, the 5' exonuclease activity of DNA polymerase released the reporter dye from the hybridized probe, resulting in a fluorescent signal. Purified VEE replicon RNA was used to generate a standard curve in the assay, and the fluorescent signal of each VEE RP sample was measured up to forty PCR cycles and compared to the fluorescent signal of the standards to determine genome equivalents.

Vaccination of mice and sample collection. Mouse study 1: Female, 6-8 week old, BALB/c, mice (Charles River Laboratory; Kingston, N.Y.) were immunized with $1 \times 10^6$ IU of VEE RP expressing the influenza A/Wisconsin HA gene that were produced using combinations of miRNA-targeted helpers and replicon vectors (Table 5). Mice were immunized at 0 and 3 weeks by subcutaneous (SC) injection into the rear footpad. Influenza HA-specific antibody and T cell responses were monitored 1 week after each immunization. Blood was collected by retro-orbital bleeds for all groups. Eight (8) mice from each group were sacrificed 1 week after each immunization and splenocytes collected from individual animals for T-cell analysis.

Figure 4:
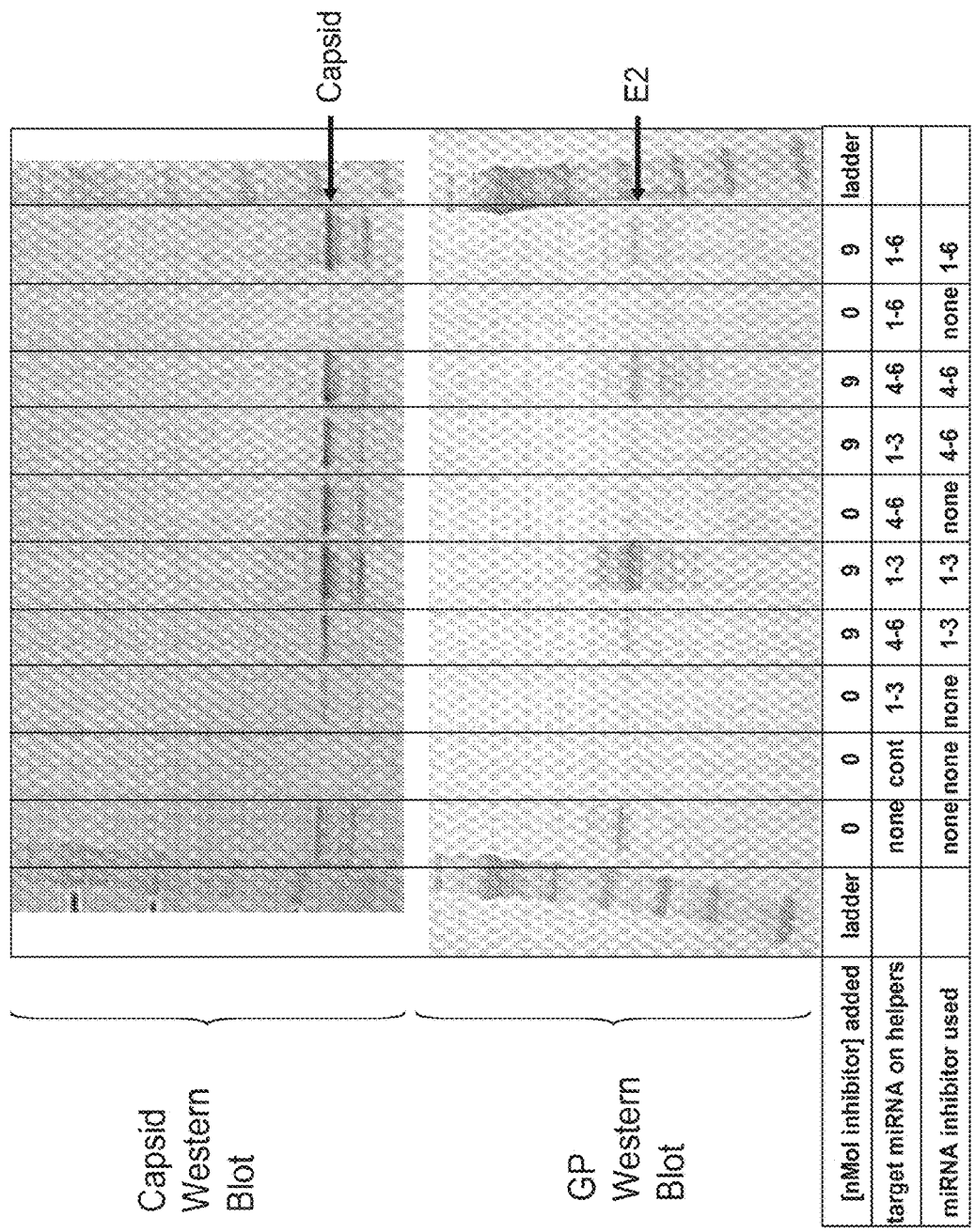
FIG. 4 is a Western blot of capsid and glycoprotein (gp) protein expression using capsid and gp helpers with matched microRNA target sequences. Vero cells were electroporated with sets of three RNAs as follows: (i) a replicon vector, with capsid helper comprising miRNA targets RC1-6 and gp helper comprising miRNA targets RC1-6, or (ii) a replicon vector, with capsid and gp helpers comprising either the miRNA RC1-3 targets or the miRNA RC4-6 targets. Each of the helpers and replicon combinations were electroporated in the presence and absence of miRNA inhibitors (2'-O-methylated RNA oligonucleotides) specific for the complete complement of miRNA targets present on the helpers. The helper RNA combinations with miRNA targets RC1-3 or RC4-6 were also electroporated in the presence of the non-matched miRNA inhibitors to demonstrate the specificity of the inhibitors used. The electroporated cells were seeded into media and incubated overnight. After incubation (~18 hours), Venezuelan equine encephalitis virus replicon particles (VEE RPs) were collected.
Figure 5:
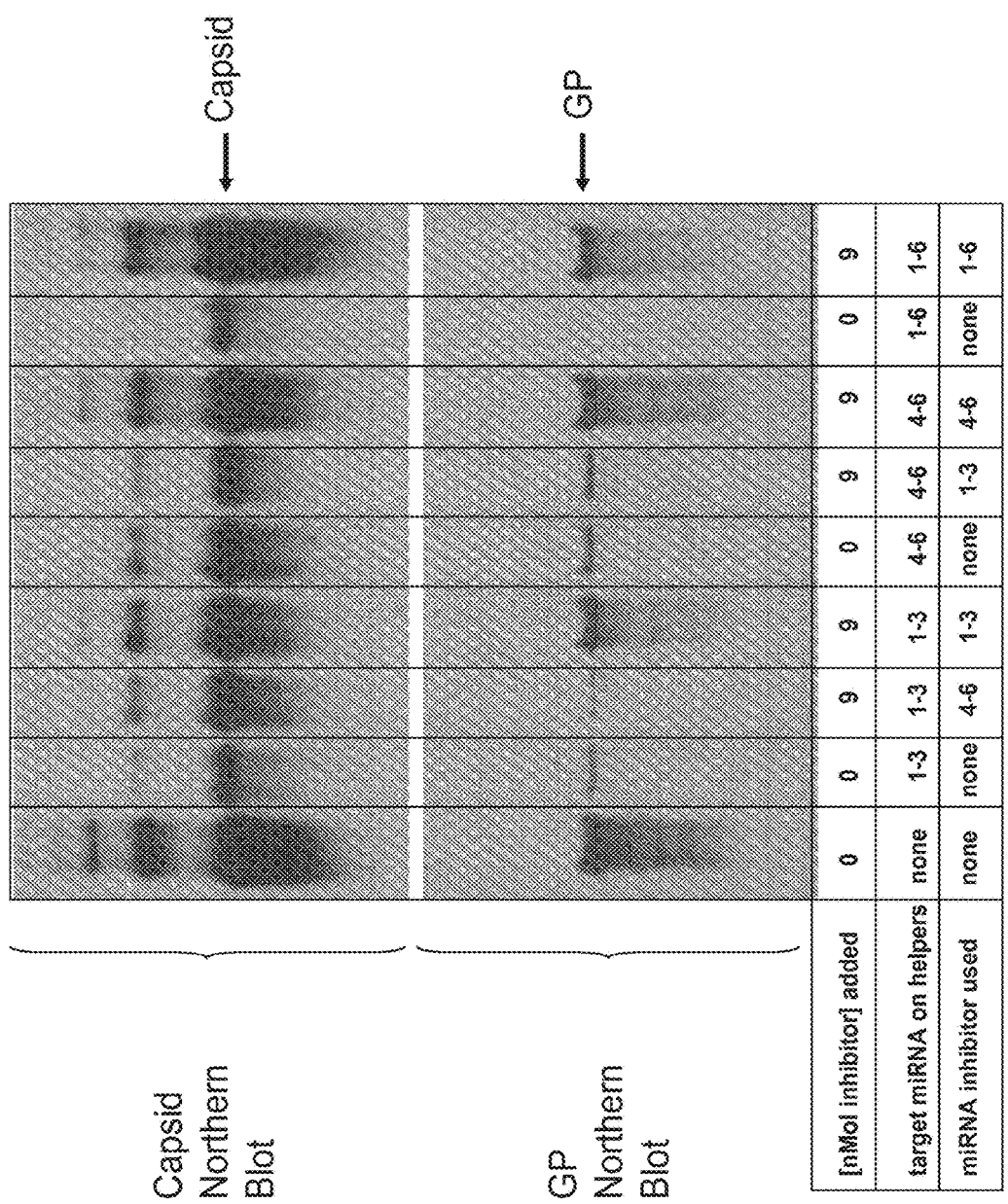
FIG. 5 is a Northern blot of capsid and gp RNA replication using capsid and gp helpers with matched microRNA target sequences and inhibitors. Samples were prepared as described for FIG. 4.
Figure 6:
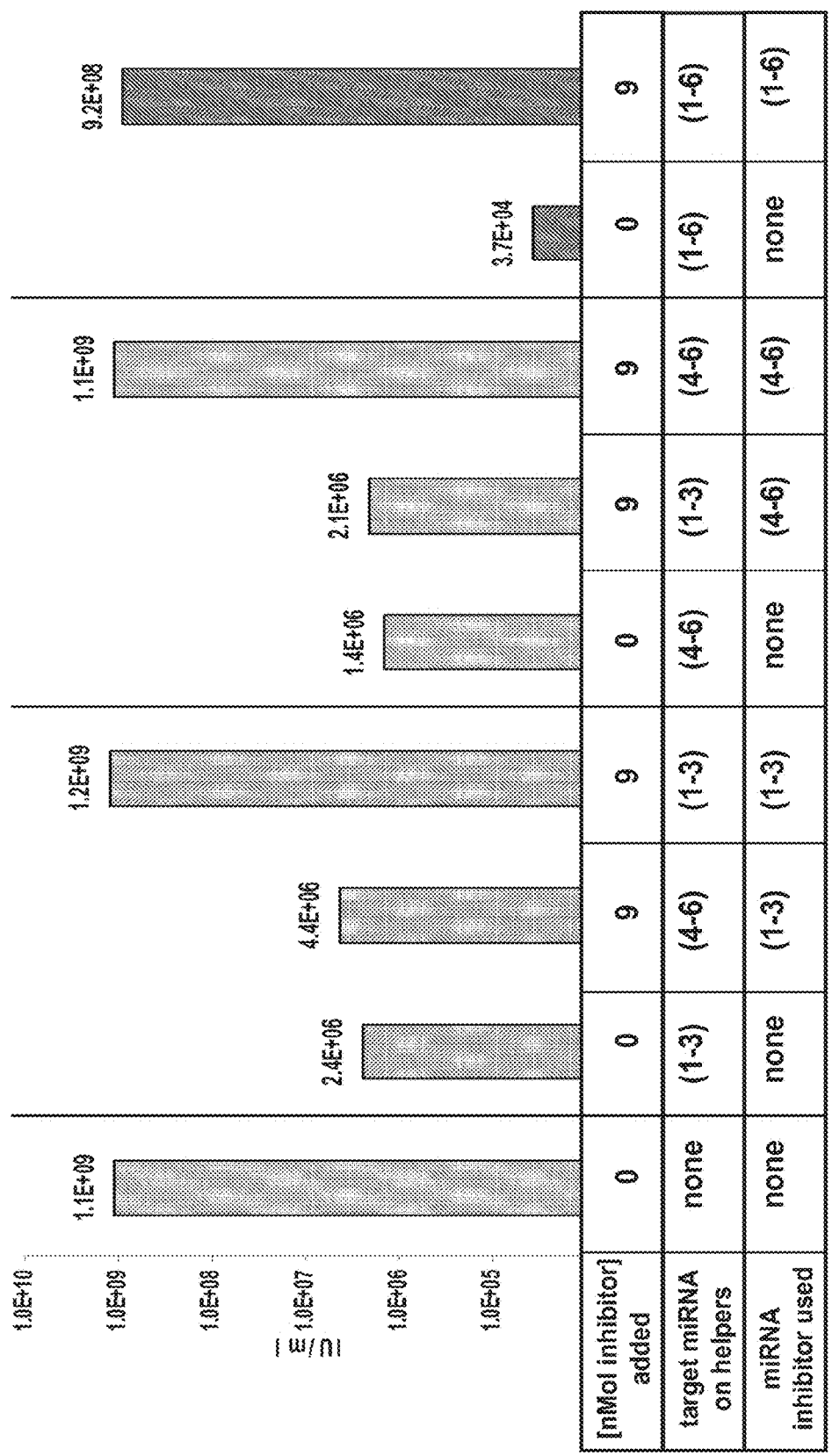
FIG. 6 is a graph showing VEE RP yields using capsid and gp helpers with matched microRNA target sequences and inhibitors. Samples were prepared as described for FIG. 4.
Figure 7:
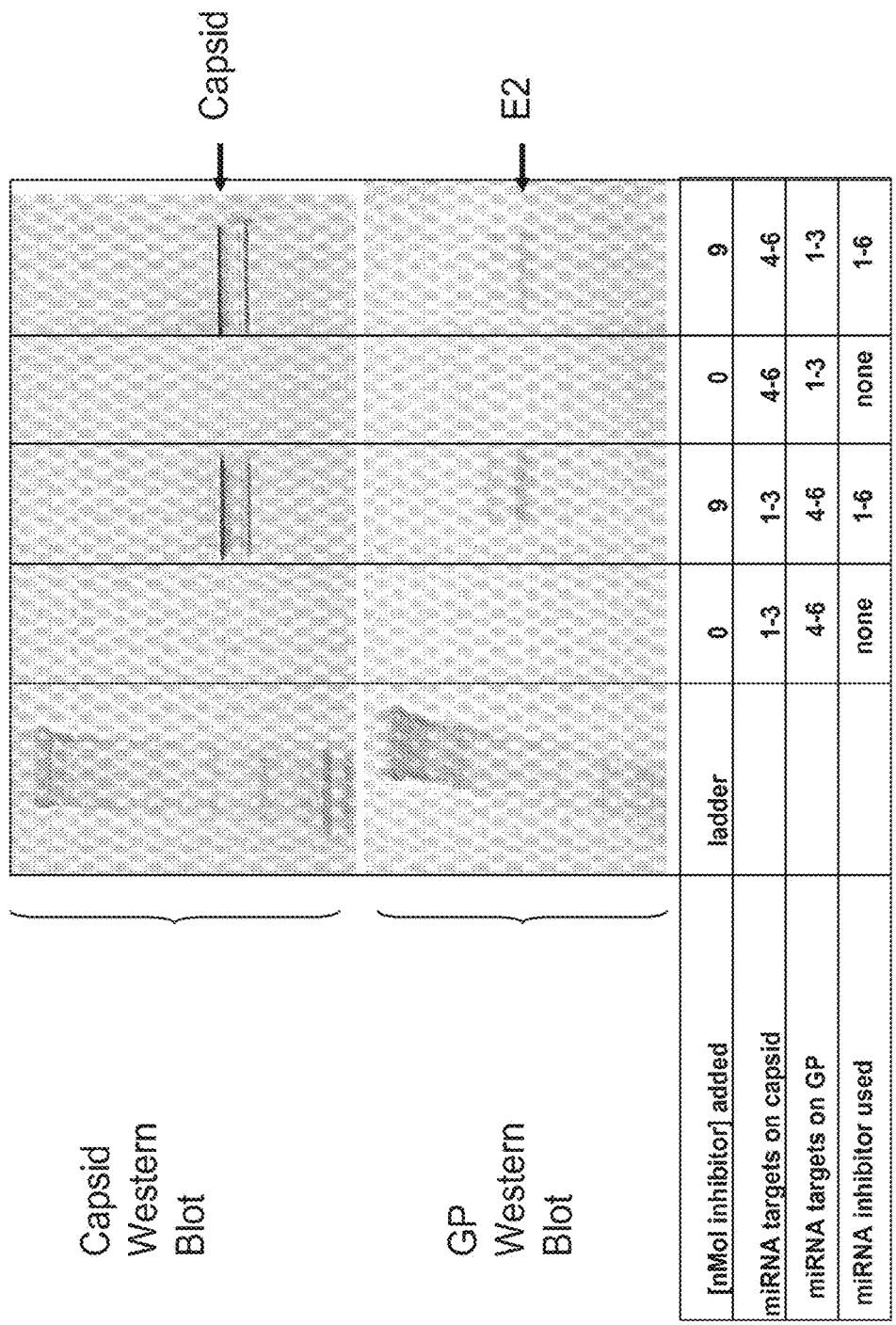
FIG. 7 is a Western blot of capsid and glycoprotein (gp) protein expression using capsid and gp helpers with non-matched microRNA target sequences and inhibitors. Combinations of a capsid helper with miRNA RC1-3 target sequences and a gp helper with miRNA RC4-6 target sequences (and vice-versa) were electroporated in the presence and absence of all 6 miRNA inhibitors (2'-O-methylated RNA oligonucleotides) specific for the complete complement of miRNA targets present on both helpers. The electroporated cells were seeded into media and incubated overnight. After incubation (~18 hours), VEE RPs were collected.
Figure 8:
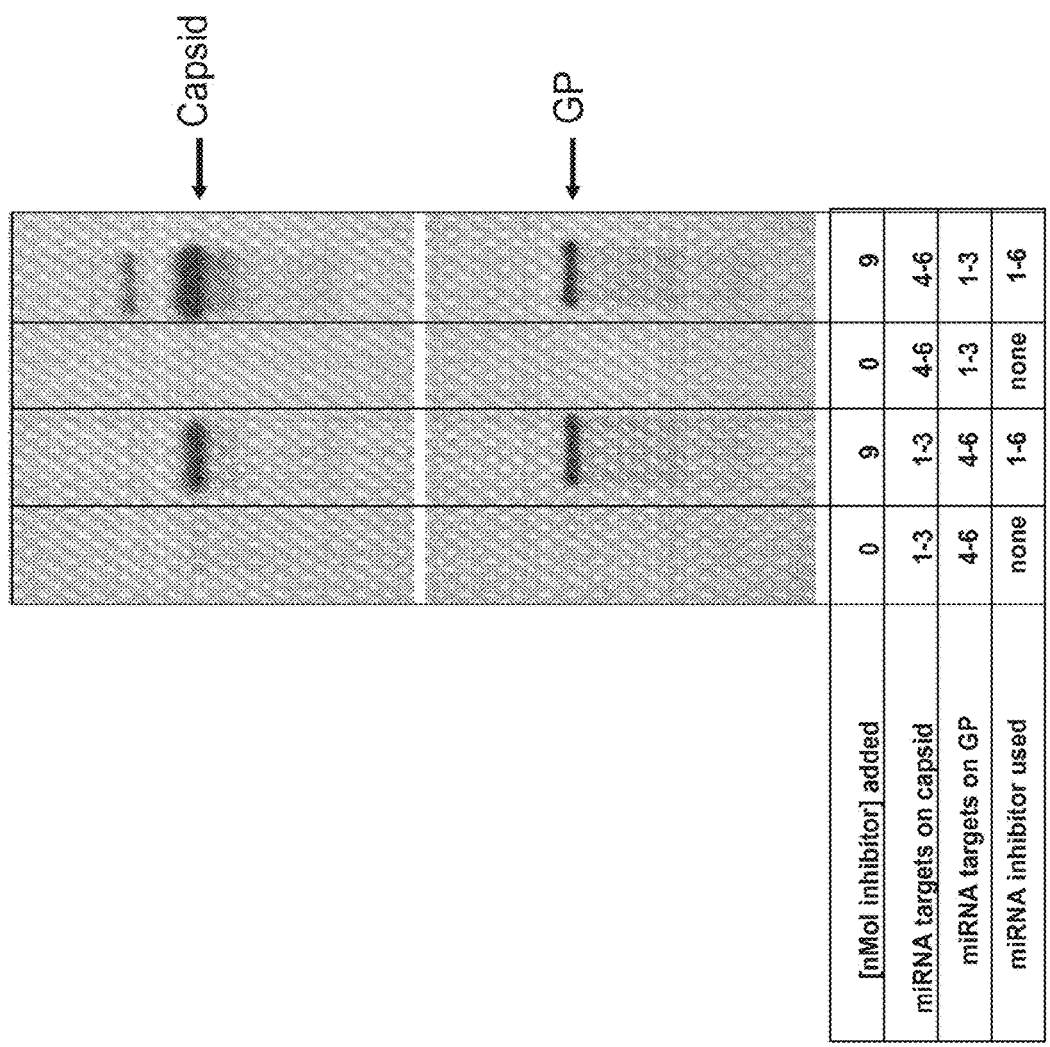
FIG. 8 is a North represents the mean of the last dilution at which the serum was able to neutralize 80% of a preparation of green fluorescent protein expressing VEE RP.
Figure 9:
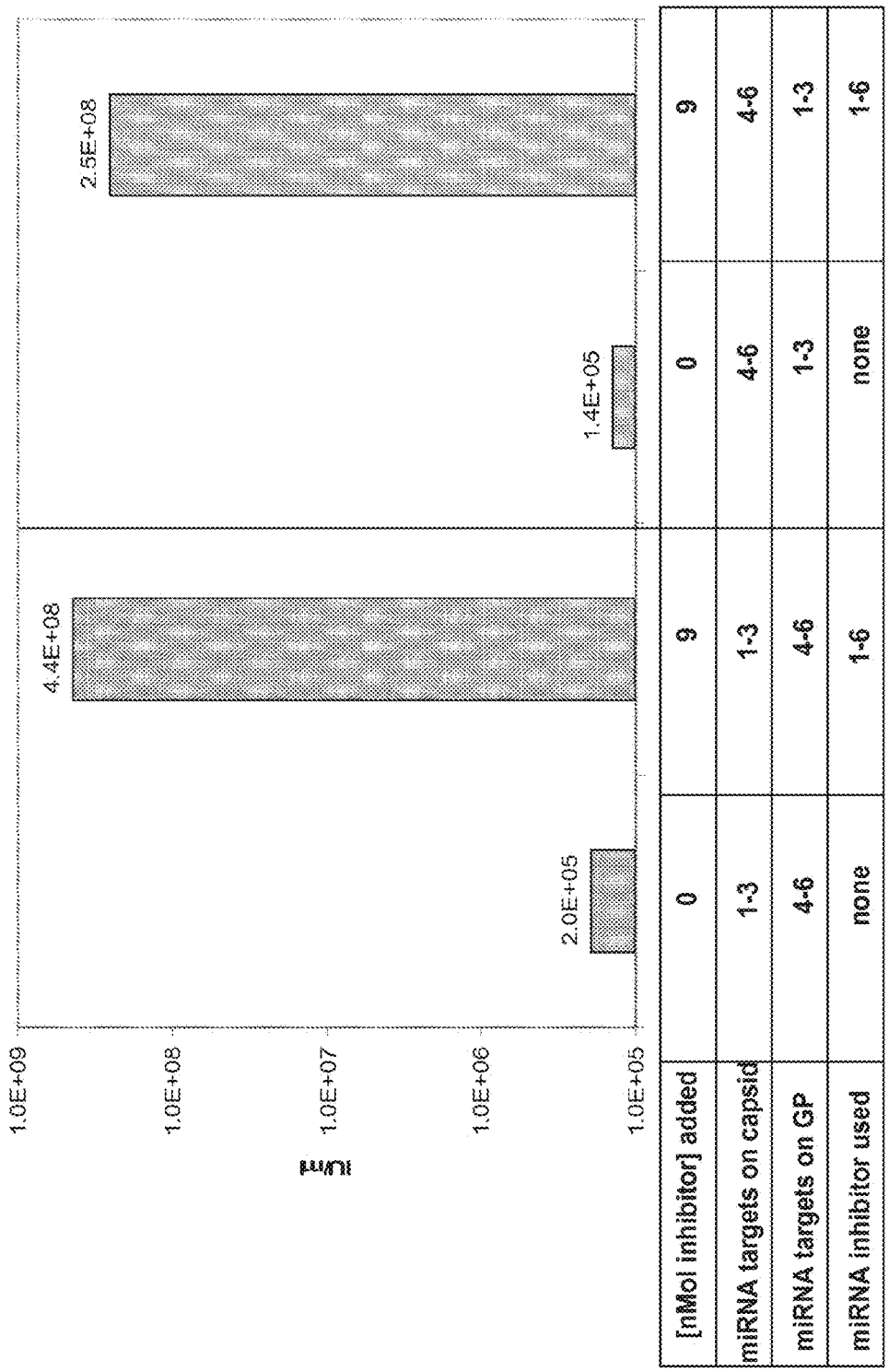
Figure 10:
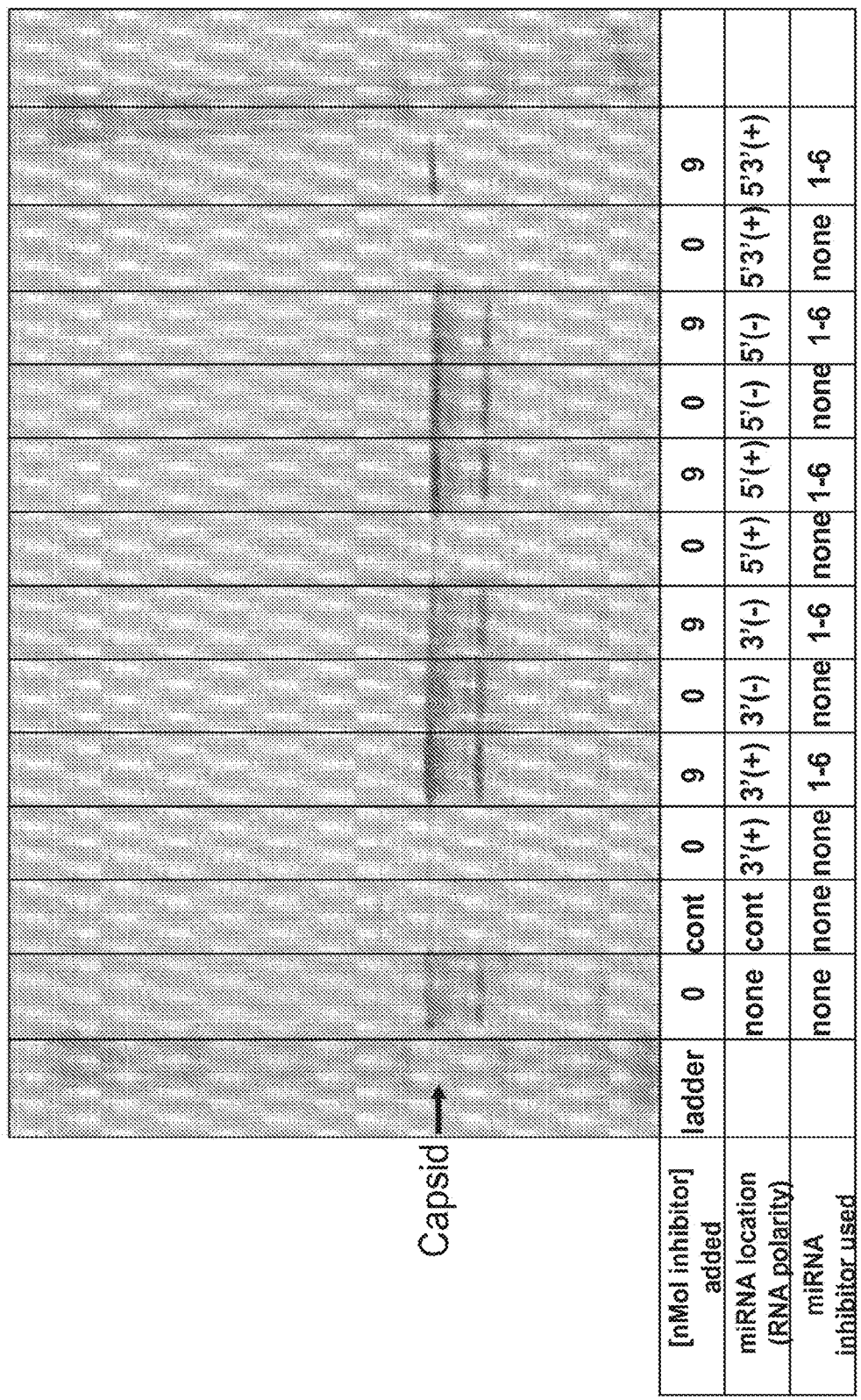
Figure 11:
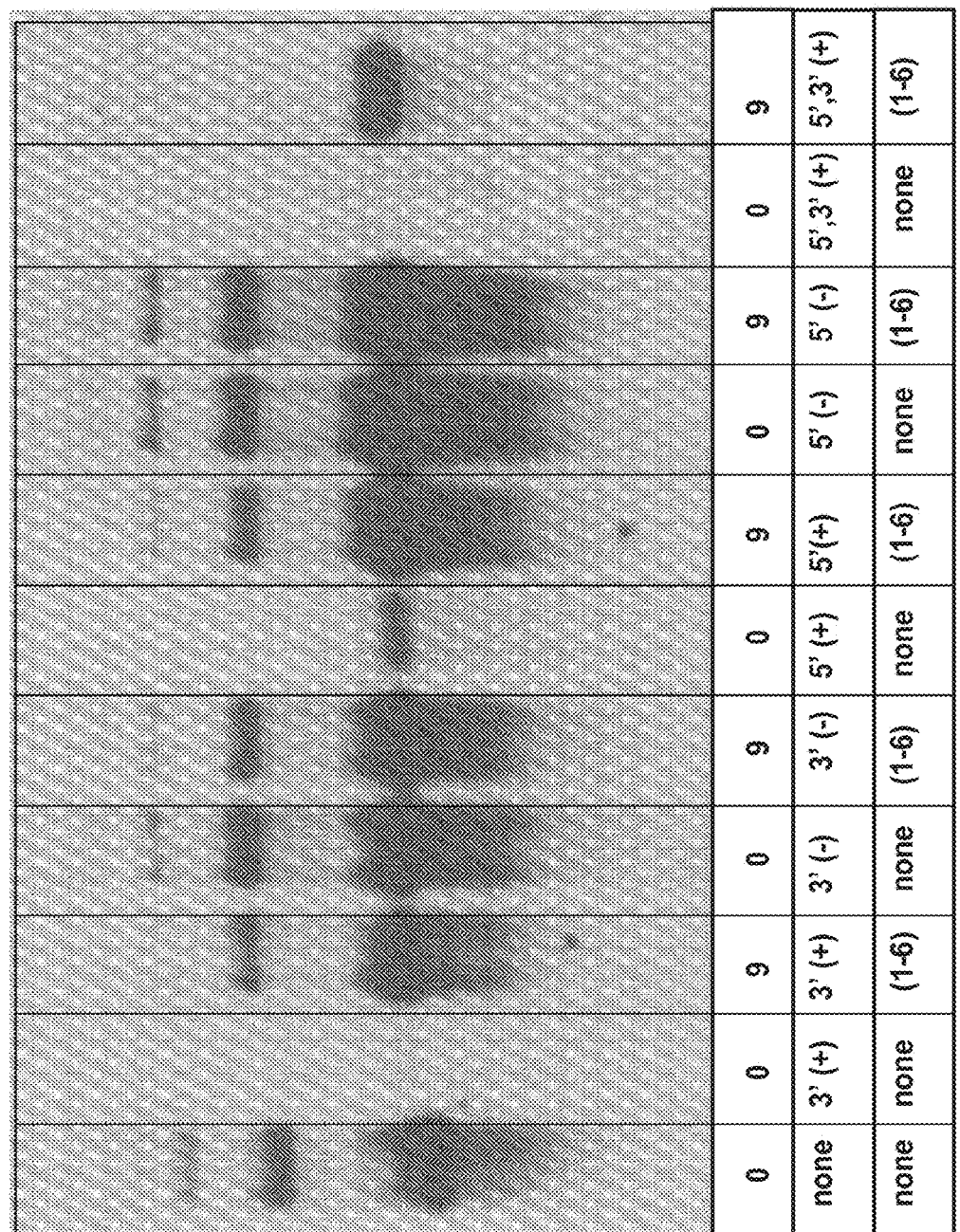
Figure 12:
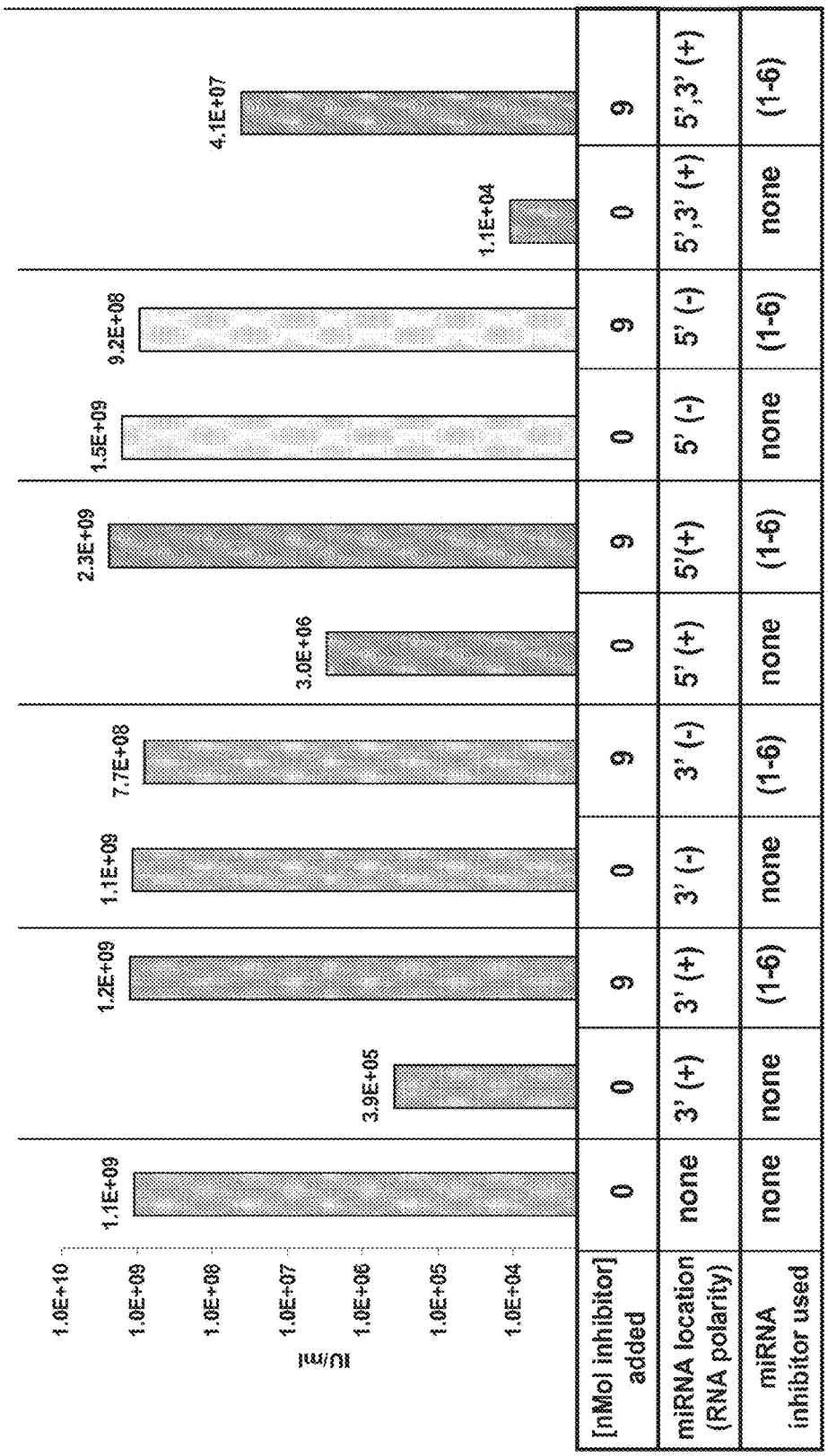
Figure 13:
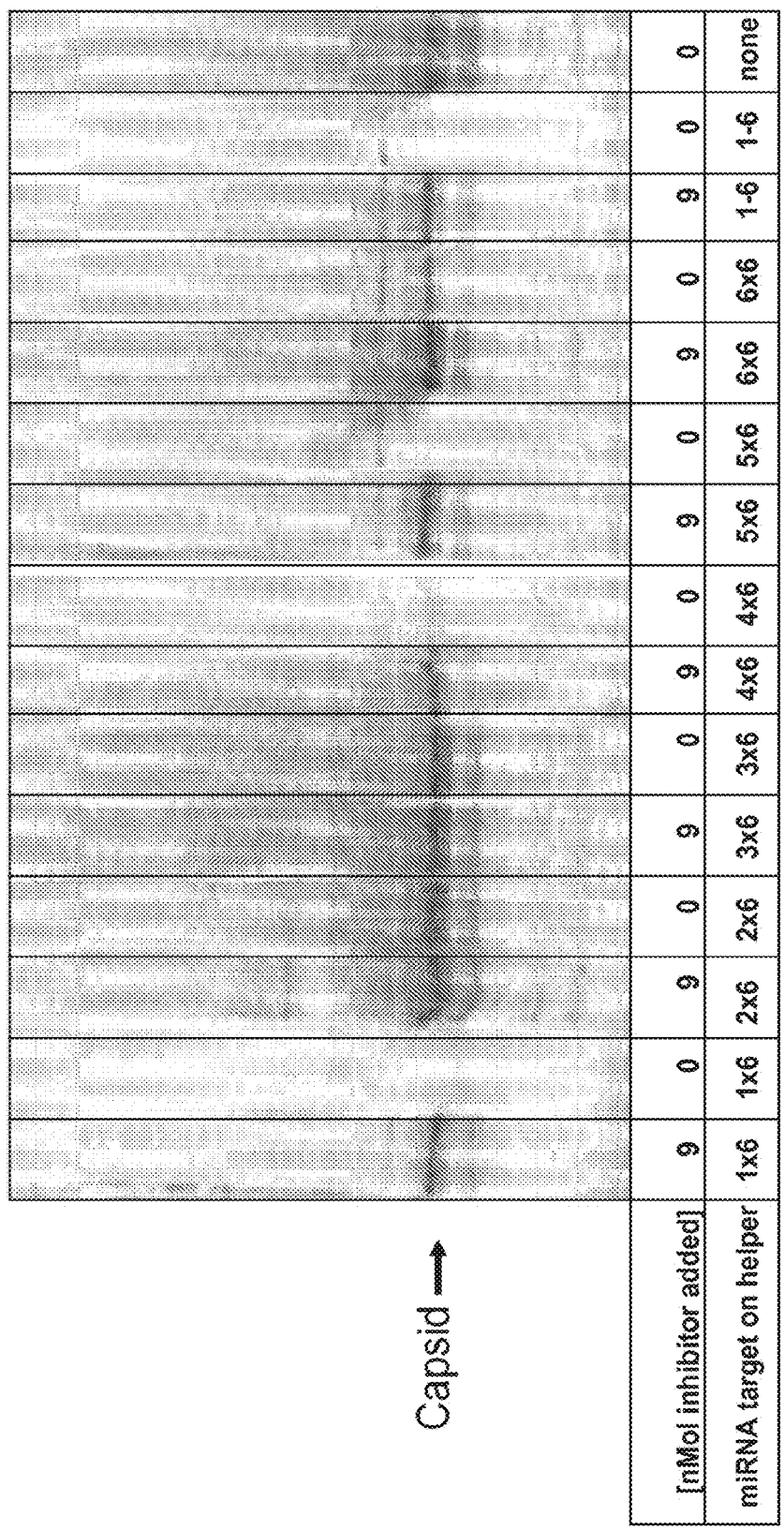
Figure 14:
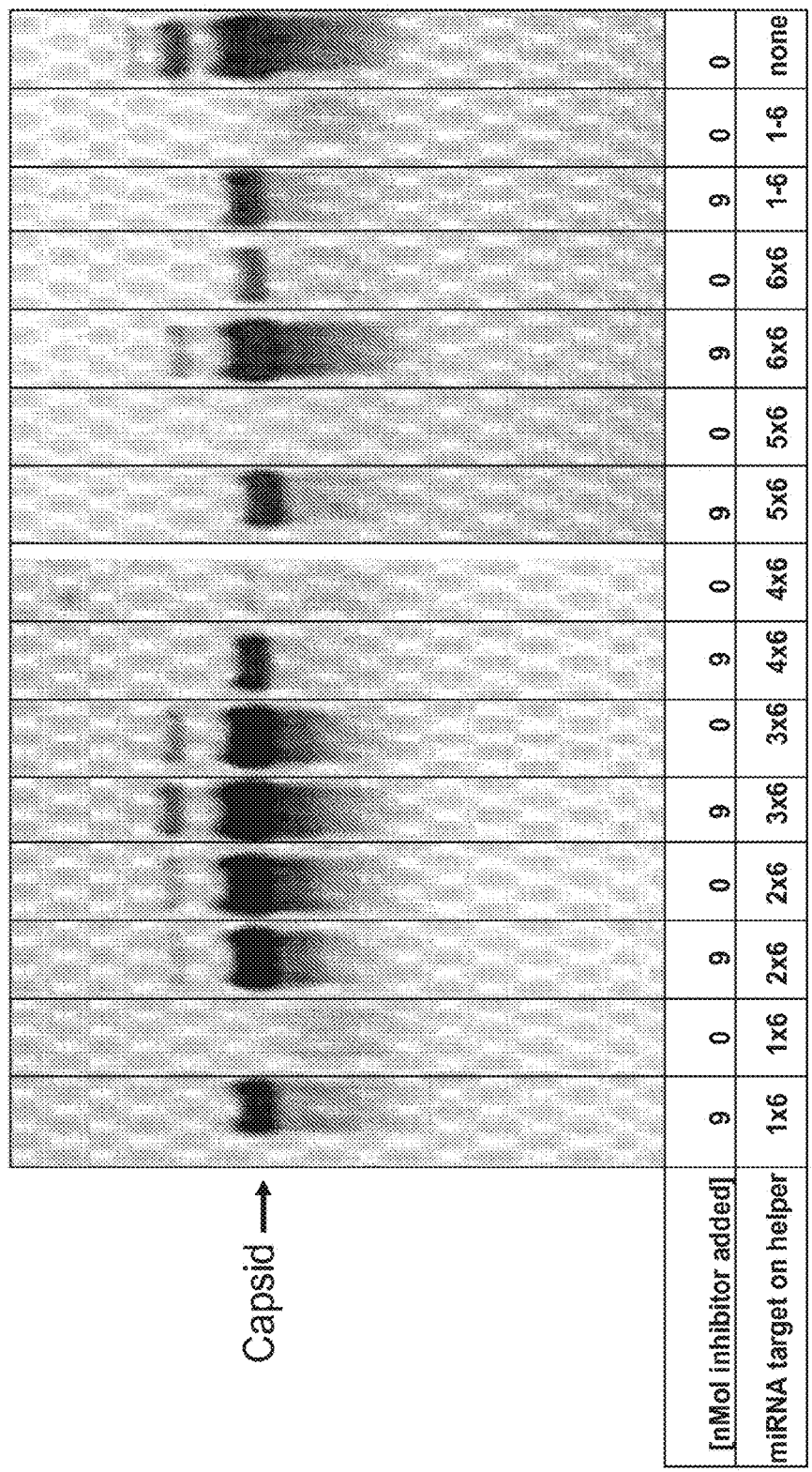
Figure 15:
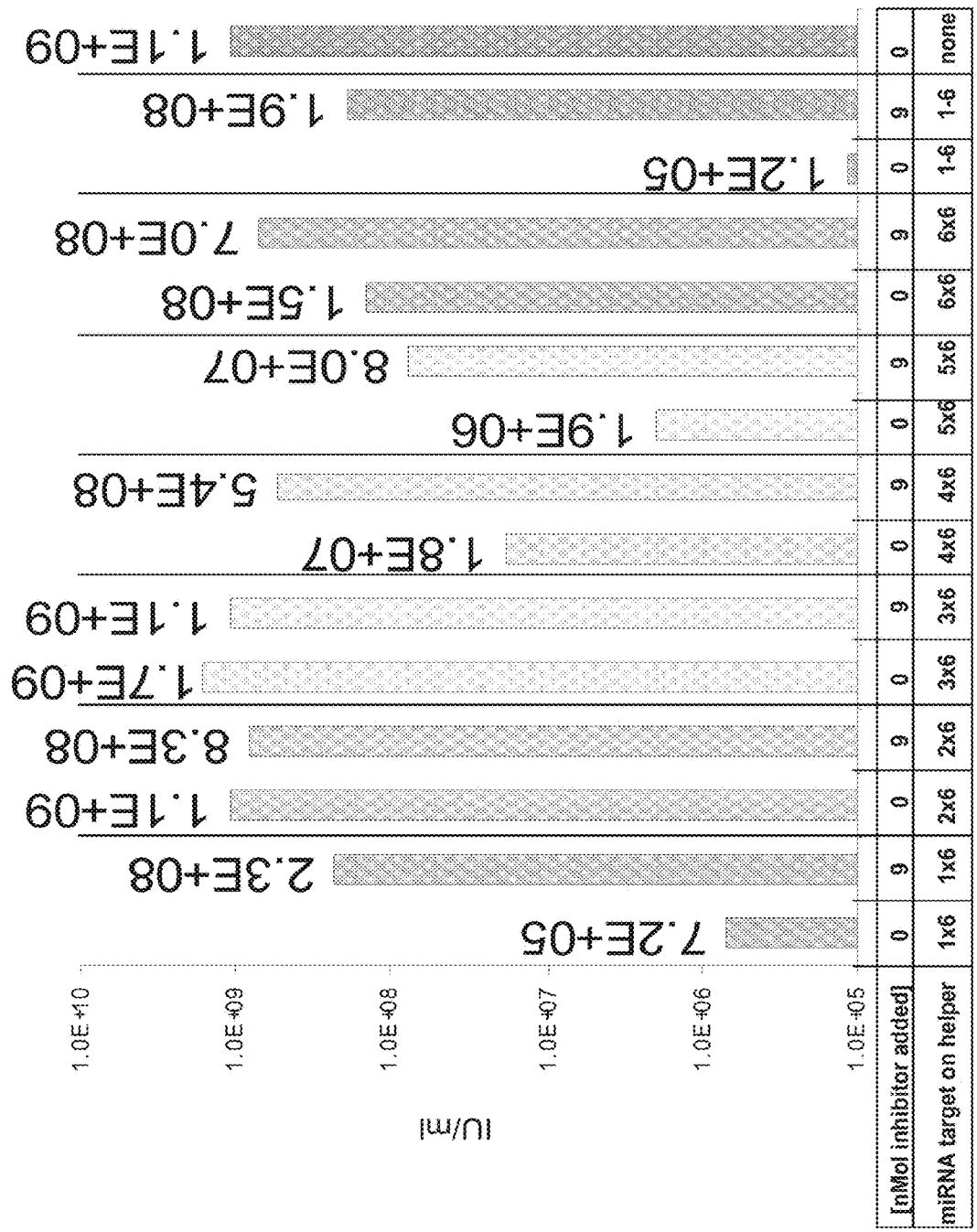

Mouse study 2: Groups of six (6), female, 6-8 week old, BALB/c, mice (Charles River Laboratory) were immunized with $5\times10^6$ TU of VEE RP expressing the herpes simplex virus II gD gene that were produced using combinations of miRNA-targeted helpers and replicon vectors (Table 6). Mice were immunized at 0 and 3 weeks by subcutaneous (SC) injection into the rear footpad. Blood was collected by retro-orbital bleeds for all groups one week after the second vaccination.

VEE RP Neutralization Assay. Serum used to supplement media and all mouse serum samples tested were heat inactivated at 56° C. for 30 minutes. Vero cells were seeded into 96-well cell culture plates and incubate at 37° C., 5% $CO_2$ overnight. Serum samples were diluted 1:10 in 96-well Titertek tubes with EMEM containing 1×NEAA, 1×Pen-Strep Fungizone, and 5% heat inactivated FBS. Samples were further diluted serially 1:2 in EMEM to reach neutralization endpoints. An equal volume of diluted GFP VEE RP was added to each of the serum dilution wells and incubated at 4° C. overnight. After overnight incubation, 100 μL of each sera/GFP VEE RP mixture was transferred to wells of Vero cells in 96-well plates. The plates were incubated at 37° C., 5% $CO_2$ for 1 hour and then the sera/VEE RP mixture was removed from each well and replaced with 100 μL fresh EMEM media. The plates were then incubate at 37° C., 5% $CO_2$ overnight. After overnight incubation the media was removed from the plates and each plate was rinsed with PBS 1 time. The number of GFP positive cells was counted for control wells to determine an 80% cut-off value. The last dilution for each serum sample where the GFP positive cell count was less than 80% of the cut-off value was considered the 80% VEE RP neutralization titer.

HA ELISA. For HA ELISA analysis, dilutions of sera from VEE RP vaccinated mice were made into PBS containing 1% BSA and 0.05% Tween-20 beginning with 1:40 followed by two fold dilutions out to 1:2560. Pre-bleed samples were diluted to only 1:40. ELISA plates (Nunc; Rochester, N.Y.), which had been coated with recombinant A/Wisconsin HA antigen (50 ng/well) (Protein Sciences Inc, Meriden, Conn.) in carbonate/bicarbonate buffer (Sigma-Aldrich; St. Louis, Mo.) overnight at 4° C., were incubated with 200 μl/well of blocking buffer (PBS, 3% BSA) at 30° C. for 1 hour. Blocked plates were washed three times with 200 μl of PBS. Fifty μl of diluted sera was added to the plates in duplicate and incubated at 30° C. for one hour. Plates were washed three times with 200 μl PBS. 100 μl of alkaline phosphatase-conjugated anti-mouse polyvalent immunoglobulins (IgG, IgA, IgM) (Sigma) diluted in blocking buffer (1:500) was added to each well. Plates with secondary antibody were incubated for 1 hour at room temperature and then washed three times with 200 μl PBS. Plates were developed using Fast™ p-Nitrophenyl phosphate tablet sets (Sigma) and reading at a wavelength of 405. An $OD_{405}$ of 0.2 or greater was considered positive.

HA ELISPOT. Splenocytes were isolated from individual animals and HA specific gamma interferon enzyme-linked immunospot (ELISPOT) assays were performed to determine the number of antigen-specific cytokine-secreting T cells. This procedure has been described previously (Reap et al., Vaccine 25(42):7441-9 (2007)).

Results

Experiments to demonstrate functional miRNA activity on helper RNAs. Experiments were conducted to determine whether eukaryotic miRNAs could be used to control/reduce alphavirus helper replication/expression, within cells, by placing miRNA target sequences in the 3' UTR of these RNAs. The target sequences selected are representative of evolutionarily conserved or ubiquitous eukaryotic miRNAs (Sempere et al., Genome Biol. 5(3):R13 (2004); Baskerville and Bartel, RNA 11(3):241-7 (2005); Farh et al., Science 310(5755):1817-21 (2005)).

The initial experiment was designed to determine whether the RC1-6 miRNA targets (let-7, lin-4, miR101, miR-155, miR-17, miR-19=targets RC1-6) or subsets of these targets (let-7, lin-4, miR101=targets RC1-3 or miR-155, miR17, miR-19=targets RC4-6) would be able to control helper replication when located in the 3' UTR of the plus-strand RNA. Vero cells were electroporated with a replicon vector combined with capsid and gp helpers with matching complements of miRNA targets on them. Specifically, replicon RNA was combined with capsid and gp helpers with miRNA targets RC1-6 on them or with both helpers carrying the miRNA targets RC1-3 on them or with both helpers carrying the miRNA targets RC4-6 on them. Each of the helper and replicon combinations were electroporated in the presence and absence of miRNA inhibitors (2'-O-methylated RNA oligonucleotides) specific for the complete complement of miRNA targets present on the helpers. In addition, the helper RNA combinations with miRNA targets RC1-3 and RC4-6 were also combined with unmatched miRNA inhibitor combinations to demonstrate the specificity of the inhibitors used. For example, miRNA RC1-3 targeted helper RNAs were treated with miRNA inhibitors specific for miRNA targets RC4-6. The electroporated cells were seeded into media and incubated overnight. After incubation (~18 hours), samples were collected to examine helper-specific protein expression (Western blot and IFA), helper-specific RNA replication (Northern blot) and VEE RP yield. The results of capsid and gp Western blot analysis are shown in FIG. 4. The results of capsid and gp-specific Northern blot analysis are shown in FIG. 5. The VEE RP yields produced by the different miRNA targeted helper RNA combinations is shown in FIG. 6. Western blot analysis indicated that expression of capsid and GP was reduced in the absence of miRNA inhibitors specific for the miRNA targets present on the helpers (FIG. 4). The difference in protein expression was particularly evident for GP. Northern blot analysis indicated that capsid and GP helper replication levels mirrored the respective helper protein expression in the presence or absence of the matched miRNA inhibitors (FIG. 5). The relative capsid and GP expression and helper RNA replication levels predicted the VEE RP yields produced. Those cells that did not receive the appropriate miRNA inhibitors (specific for the miRNA targets on the helpers) produced 3 to 4.5 orders of magnitude less VEE RP (FIG. 6).

The experiment described above matched the miRNA targets on each helper. Next, an experiment was conducted to determine whether different combinations of miRNA targets could be present on the helpers and still rescue VEE RP yields when the appropriate combination of miRNA inhibitors was supplied. Combinations of a capsid helper with RC1-3 targets and a GP helper with RC4-6 (and vice-versa) were tested in the presence or absence of a mixture of all 6 miRNA inhibitors. Western blot analysis indicated that expression of capsid and GP was reduced in the absence of miRNA inhibitors specific for the miRNA targets present on the helpers (FIG. 7). The difference in protein expression, in the absence of inhibitor, was more pronounced than that noted when the miRNA targets present on the helpers were matched (FIG. 4). Northern blot analysis indicated that capsid and GP helper replication levels mirrored the respective helper protein expression in the presence or absence of the matched miRNA inhibitors (FIG. 8). As found in the experiment with matched miRNA targeted helpers, the relative capsid and GP expression and helper RNA replication levels predicted the VEE RP yields produced. VEE RP yields were 3 orders of magnitude lower in cells that did not receive the miRNA inhibitors when compared to those that did (FIG. 9).

Figure 16:
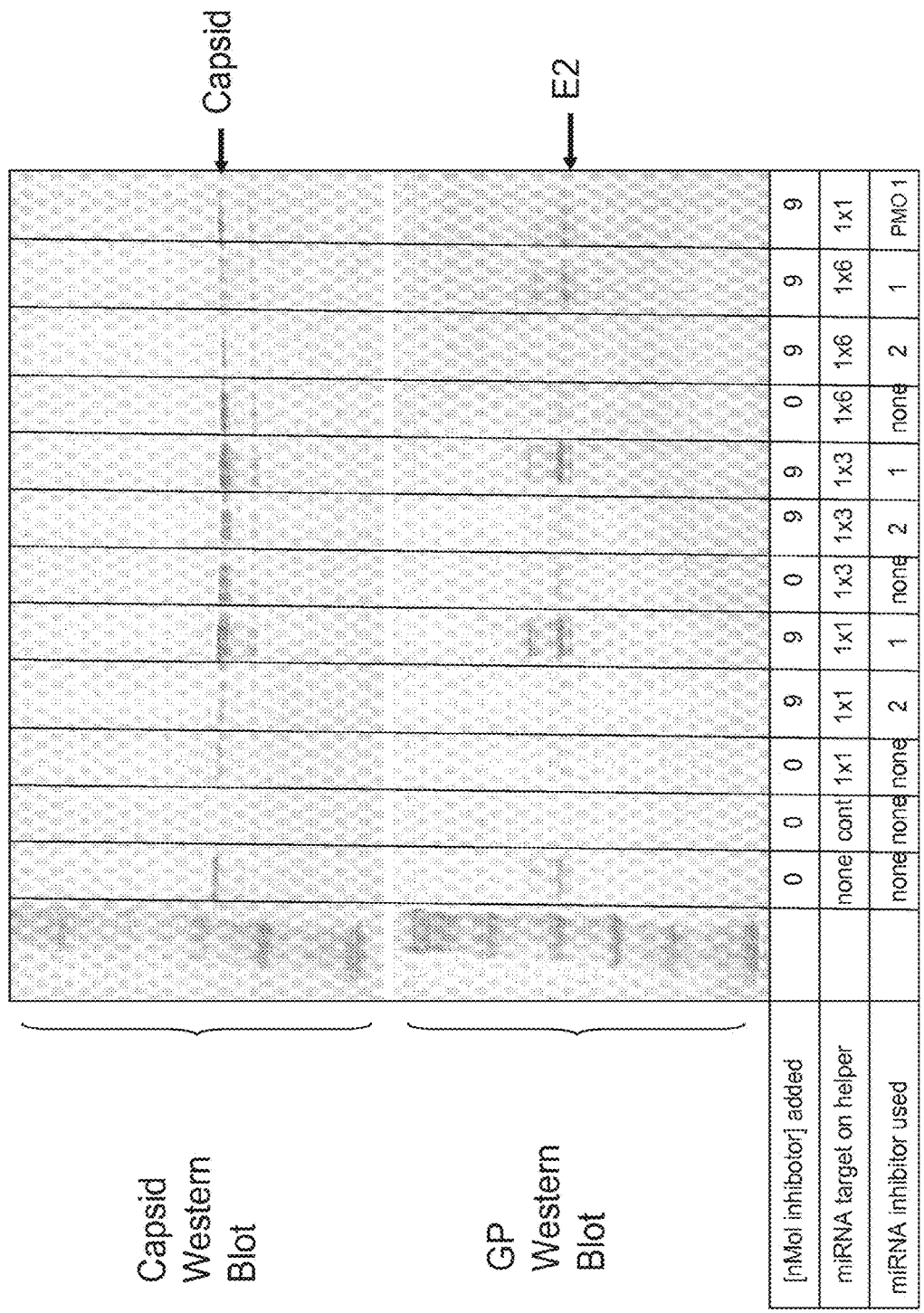
Figure 17:
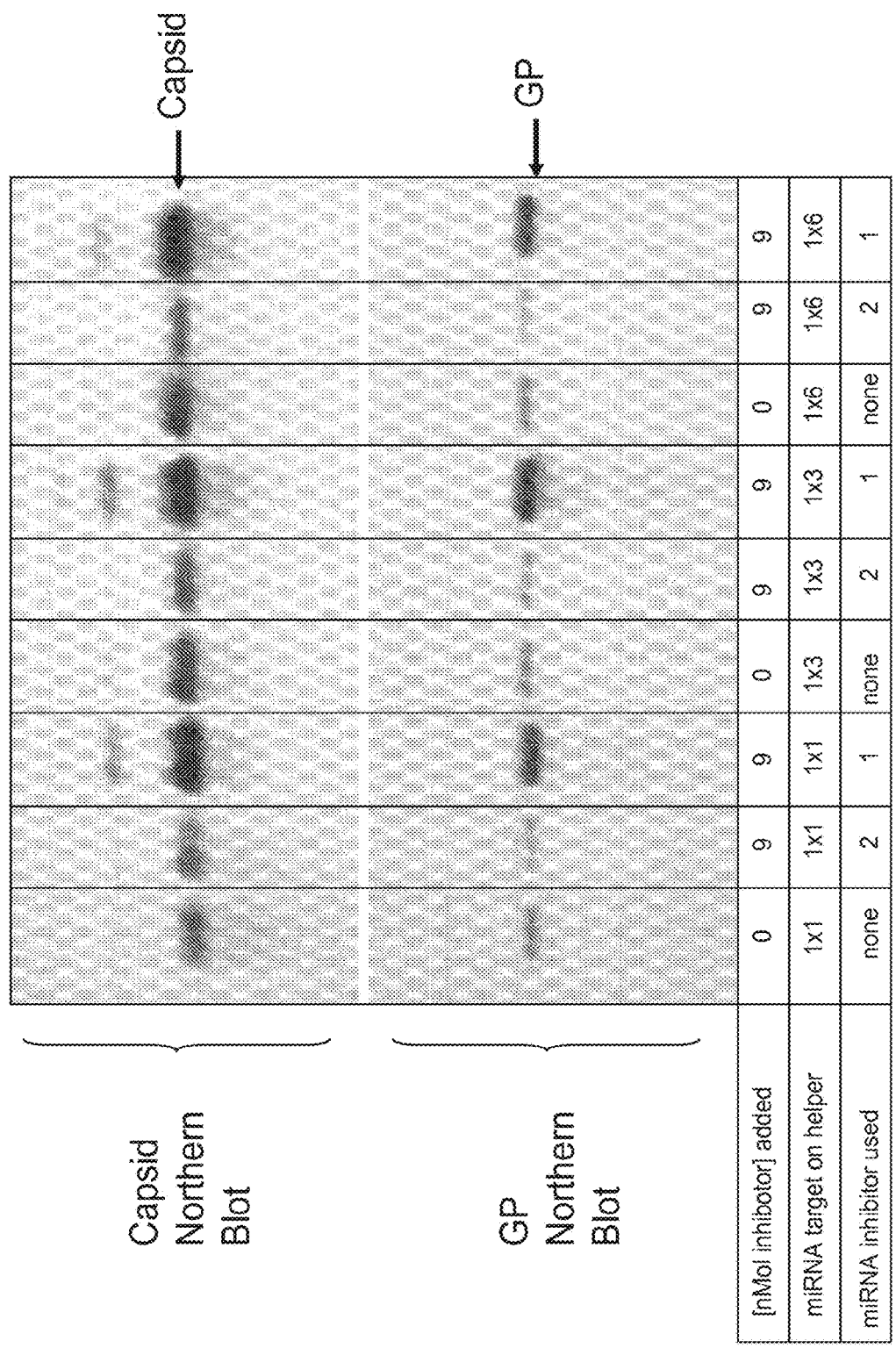
Figure 18:
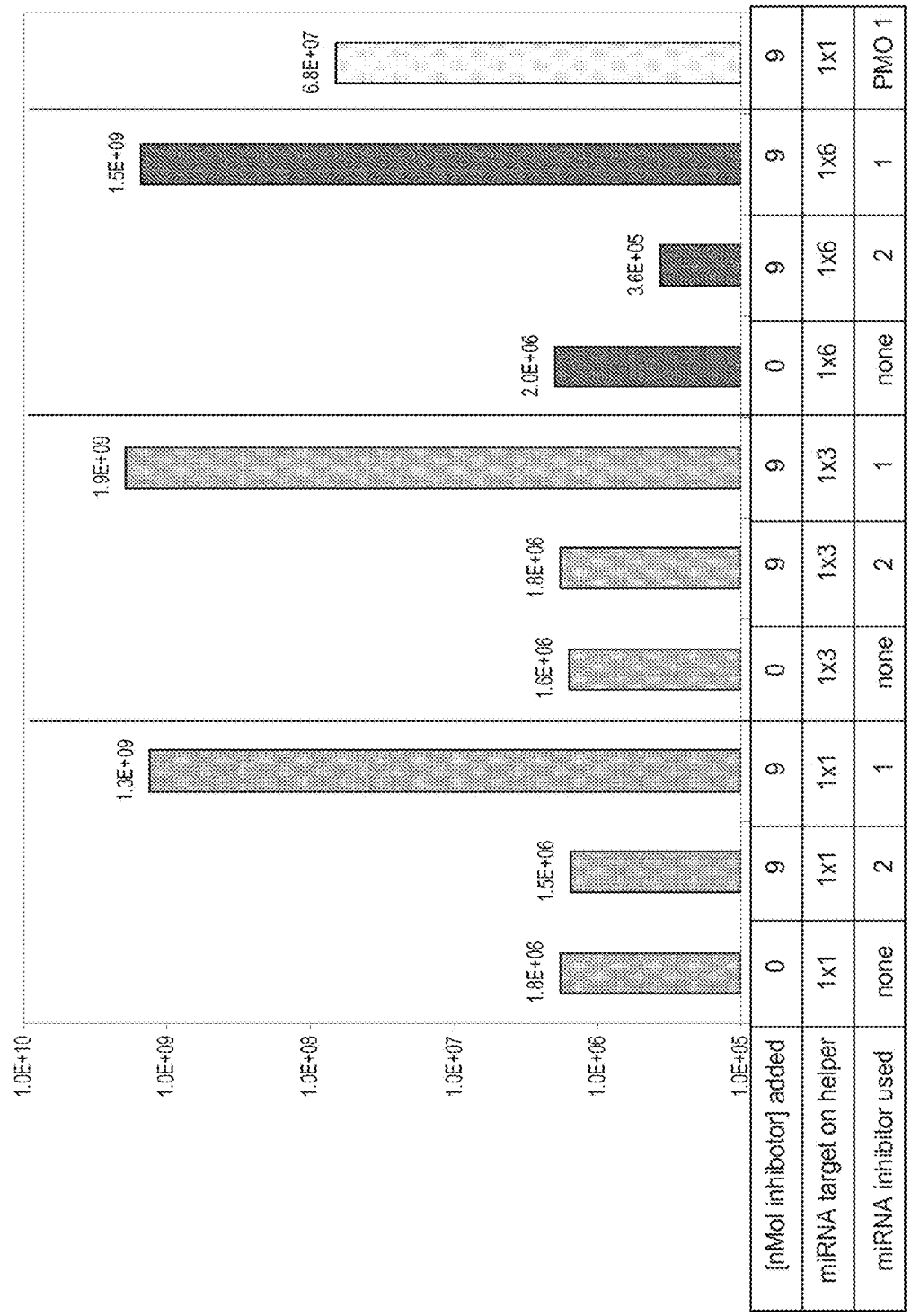
Figure 19:
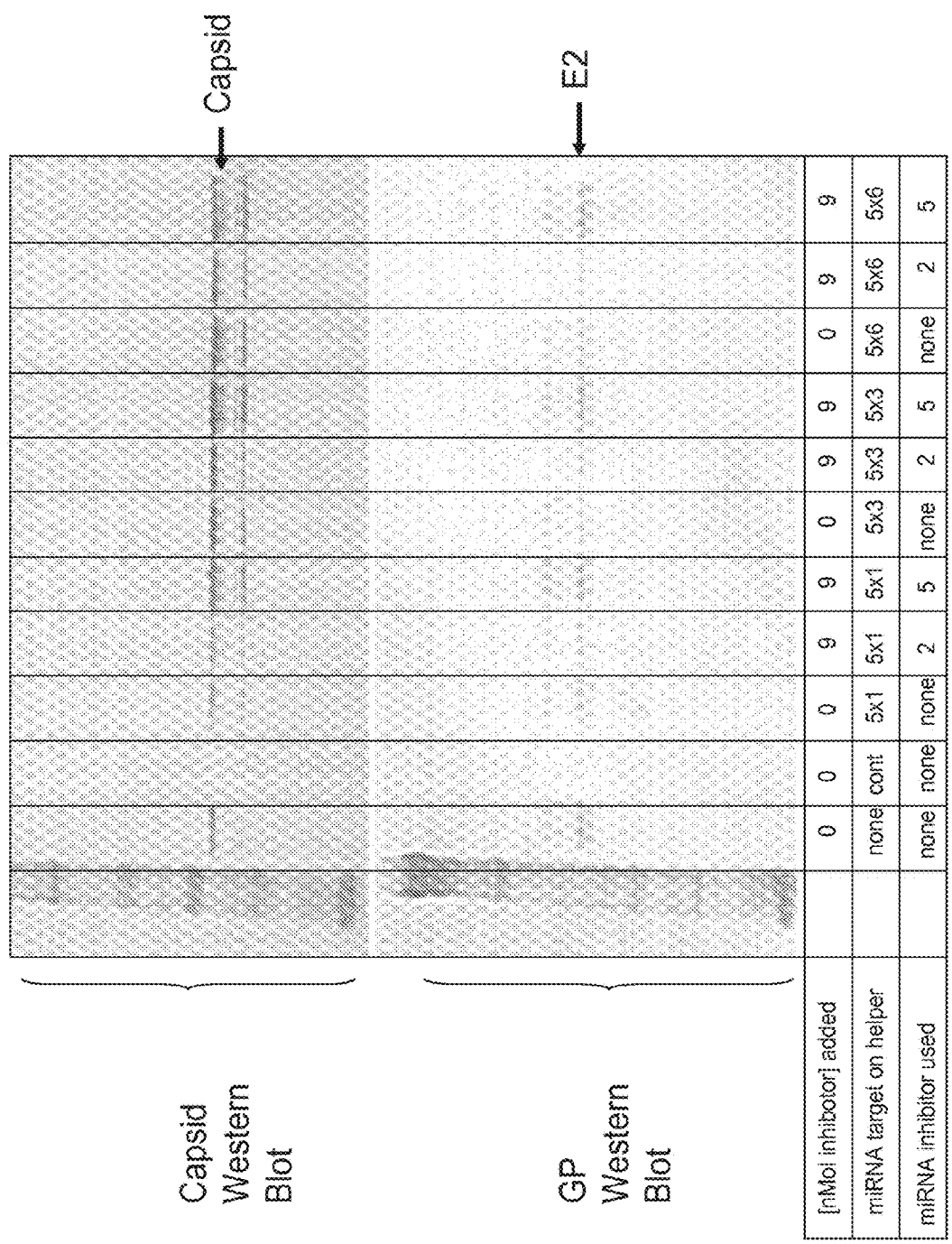
Figure 20:
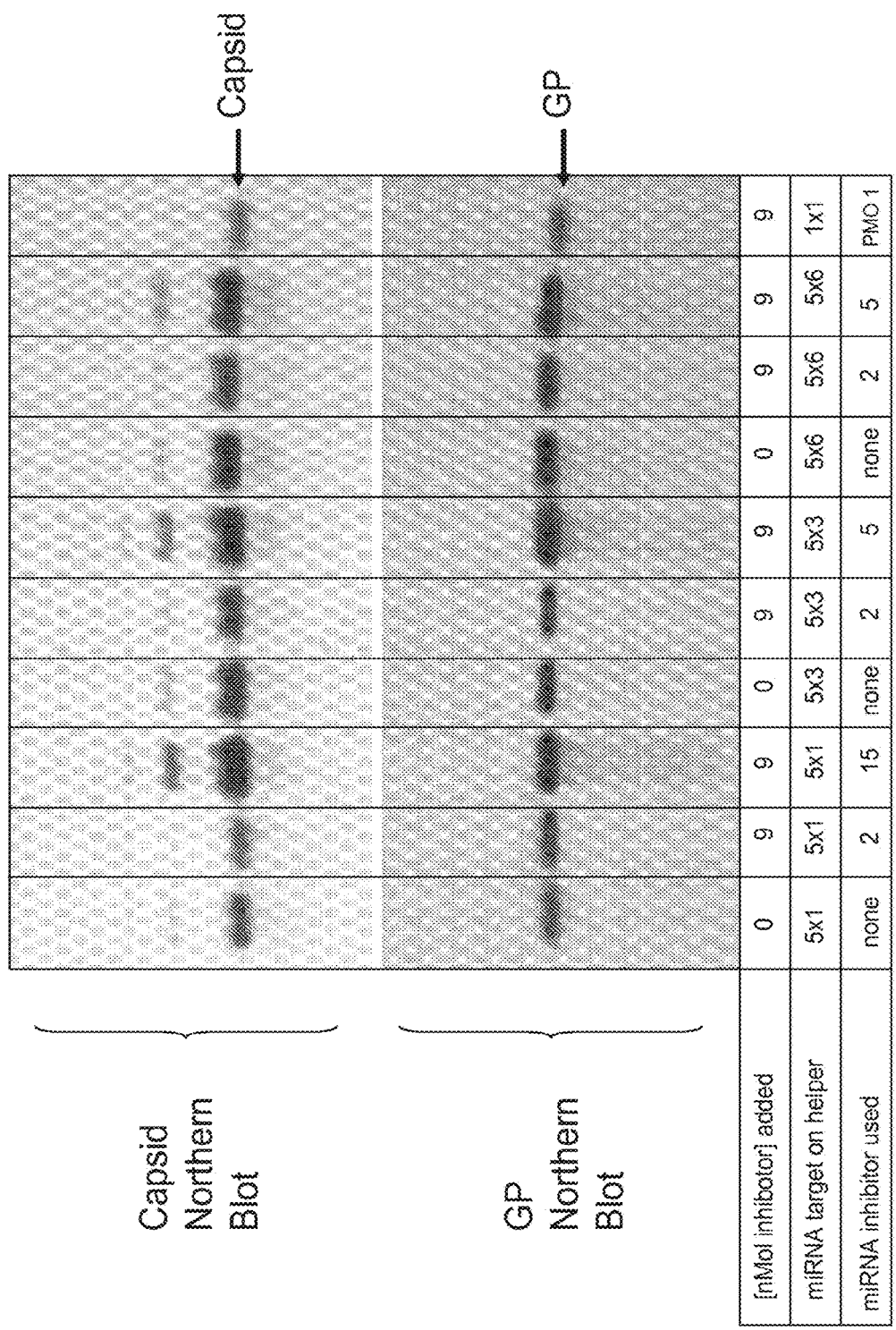
Figure 21:
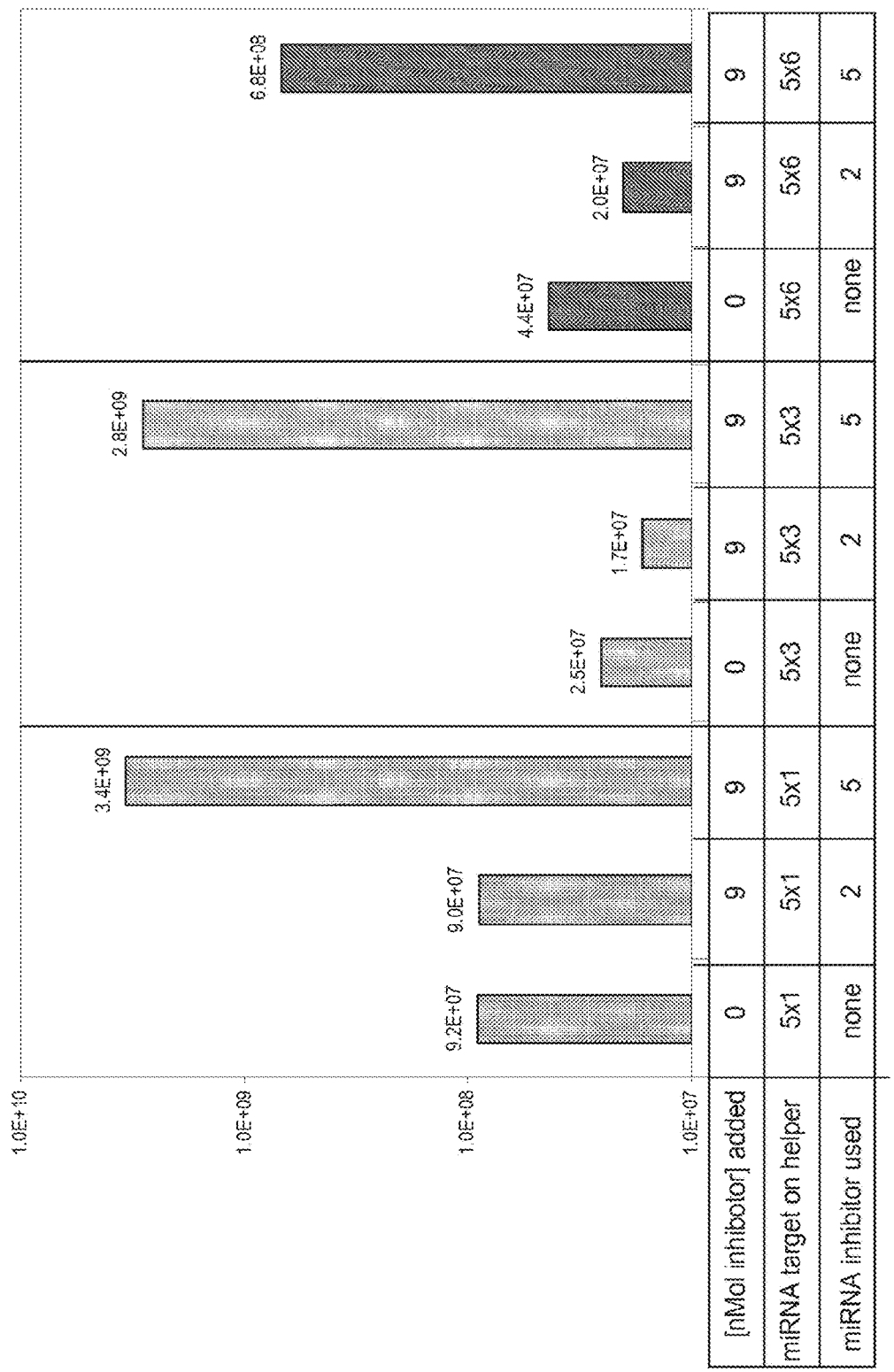

Experiments to determine location requirement of miRNA targets on helper RNAs. To determine whether the miRNA targets RC1-6 could function in locations other than the 3' UTR of the plus-strand capsid helper RNA, additional capsid helpers were constructed that moved the miRNA RC1-6 targets to the 5' UTR of the capsid helper RNA on both the plus-strand and minus-strand RNA templates for replication. In addition, the miRNA RC1-6 targets were engineered in the 3' UTR on the minus-strand RNA template. These experiments were conducted with a combination of replicon RNA, unmodified GP helper RNA and one of the miRNA RC1-6 targeted capsid helper RNAs in the presence and absence of miRNA inhibitors specific for the miRNA targets present on the helpers. The electroporated cells were seeded into media and incubated overnight. After incubation (~18 hours), samples were collected to examine capsid helper-specific protein expression (Western blot and IFA), RNA replication (Northern blot) and VEE RP yield. The results of capsid-specific Western and Northern blot analysis are shown in FIG. 10 and FIG. 11, respectively. The VEE RP yields produced using the different miRNA targeted capsid helper is shown in FIG. 12. Both Western and Northern blot analysis indicated that the miRNA targets function most effectively when on the plus-strand helper RNA. Helper expression and replication were significantly reduced when the plus-strand RNA was targeted and miRNA inhibitors were not supplied at the time of RNA electroporation of cells. In addition, miRNA targets in either a 5' or 3' location relative to the capsid gene or in both the 5' and 3' locations simultaneously were effective at reducing expression and replication of the helper RNA in the absence of miRNA inhibitor addition. As noted in previous experiments, VEE RP yields were 3 orders of magnitude lower in cells that did not receive the miRNA inhibitors when compared to those that did (FIG. 12).

Experiments to determine contribution of individual miRNA targets on helper RNA replication. To determine what effect each miRNA target was contributing to the overall control of replication, six copies of each individual target miRNA sequence were cloned into the 3' UTR of the capsid helper plus-strand RNA. Capsid helper RNA and unmodified GP helper RNA were combined with replicon RNA and electroporated into Vero cells in the presence or absence of miRNA inhibitors specific for the miRNA targets present on the capsid helper. The electroporated cells were seeded into media and incubated overnight. After incubation (~18 hours), samples were collected to examine capsid-specific protein expression (Western blot and IFA), RNA replication (Northern blot) and VEE RP yield. The results of capsid-specific Western and Northern blot analysis are shown in FIG. 13 and FIG. 14, respectively. These results show that cellular miRNA specific for let-7, miR-155, miR-17 and miR-19 (RC1, RC4, RC5 and RC6, respectively) are capable of down-regulating helper expression and replication (in the absence of specific miRNA inhibitor) and that miRNA specific for lin-4 (RC2) and miR-101 (RC3) are less effective at controlling helper expression/replication in this Vero cell packaging system (FIG. 13 and FIG. 14). The VEE RP yields produced using the different miRNA targeted capsid helpers are shown in FIG. 15. The capsid helper containing all six miRNA targets (RC1-6) demonstrated the largest difference in VEE RP yields in the presence and absence of miRNA inhibitor (3 orders of magnitude) indicating an additive effect of the miRNA targets on helper replication in this experiment. The timer of miRNA let-7 (RC1x6) target demonstrated the next largest effect on VEE RP yield (~2.5 orders of magnitude) with miR-155 (RC4x6) and miR-17 (RC5x6) both demonstrating ~1.5 orders of magnitude differences in VEE RP yield. The helper with six copies of the miR-19 target (RC6x6) produced about one-half log less VEE RP yield while lin-4 (RC2x6) and miR-101 (RC3x6) targets demonstrated little difference in VEE RP yield (FIG. 15). In combination, the Western, Northern and VEE RP yield data indicate that these selected individual miRNA targets play a larger or smaller role in the overall miRNA effect on helper replication in Vero cell packaging, but all can contribute to the overall effect.

Experiments to determine copy number requirement of miRNA targets on helper RNAs. The experiments described above suggested that each miRNA had a different effect on miRNA-targeted helper replication (and VEE RP yield) and that some miRNA targets were more efficient at controlling helper replication in Vero cells than others. Additional helper constructs were produced using miRNA targets that imparted control of RNA replication in Vero cells. Two miRNA targets, RC1 (let-7) and RC5 (miR-155) were selected for these studies because they represent miRNA targets with a strong and a medium effect on helper replication, in Vero cells, respectively. The new capsid and GP helpers were constructed with either a single copy or three copies of each individual miRNA target (RC1x1, RC1x3, RC5x1 and RC5x3) engineered into the 3' UTR of the plus-strand RNA. These helpers were designed to determine what number of miRNA target copies, for these particular miRNAs, was required to impart RNA replication control in Vero cells.

Capsid and GP helper RNAs, with the same complement of miRNA targets, were combined with replicon RNA and electroporated into Vero cells in the presence or absence of miRNA inhibitors specific for the miRNA targets present on the helpers. In one set of electroporations the 2'-O-methylated oligonucleotide miRNA inhibitor specific for let-7 was replaced with a phosphorodiamidate morpholino oligomer (PMO) specific for let-7 miRNA to determine whether this type of molecule would function to block the action of the let-7 miRNA on the targeted helpers. The electroporated cells were seeded into media and incubated overnight. After incubation (~18 hours), samples were collected to examine helper-specific protein expression, RNA replication and VEE RP yield. As few as one copy of the let-7 or miR-155 miRNA target (RC1x1 or RC5x1, respectively) resulted in reduction of both protein expression (FIG. 16 and FIG. 19) and RNA replication (FIG. 17 and FIG. 20) of both helpers. The reduction noted in protein expression and helper replication was mirrored in the VEE RP yields produced from cells in the absence of specific inhibitor (FIG. 18 and FIG. 21). Helpers containing the let-7 miRNA target (RC1) were more completely controlled (even with a single copy) than were helpers containing the miR-155 miRNA target(s). VEE RP yields in the absence of miRNA-specific inhibitor were reduced ~3 orders of magnitude using helpers with the RC1 target no matter what the copy number was (FIG. 18). In contrast, there was a larger reduction in VEE RP yields in the absence of miRNA-specific inhibitor using helpers with either 3 or 6 copies of the miR-155 miRNA targets (5x3 and 5x6, respectively) than with a single miR-155 target (5x1) (FIG. 21). These data indicate that more than one copy of the miR-155 target (RC5) was required to have an effect similar to one copy of the let-7 target (RC1) for optimal RNA replication control in this Vero cell. In addition, the PMO-based let-7 miRNA inhibitor restored protein expression (FIG. 16) and RNA replication (FIG. 20) to levels similar to the rescue noted for 2'-O-methylated oligonucleotide miRNA inhibitor. VEE RP yields produced in the presence of PMO-based inhibitor were nearly 2 orders of magnitude higher than in the absence of inhibitor but not as great as those using 2'-O-methylated oligonucleotide miRNA inhibitors (FIG. 18).

Experiments to demonstrate the functionality of miRNA targeted, cleavage deficient, capsid helper RNAs. Experiments were conducted to demonstrate that the m152 capsid mutation 1) blocked production of VEE RP when the mutation was introduced into the capsid gene in the context of a DNA helper and 2) when introduced into an miRNA targeted capsid RNA helper, caused no or little reduction in VEE RP yield, when miRNA inhibitors were included in the packaging cell system for producing VEE RP. Vero cells were electroporated with replicon RNA and the following helper combinations 1) pHCMV-Vsp, 2) pHCM-Vsp (m152), 3) dHcap6-mut1(W-stop)m152 and dHgp6-mut1, 4) dHcap6-mut1(W-Stop)m152 RC4-6 and dHgp6-mut1, and 5) dHcap6-mut1(W-Stop)m152 RC4-6 and dHgp6-mut1 plus miRNA inhibitors specific for RC4-6. The VEE RP yields produced from each of these combinations are shown in the Table 2.

TABLE 2

VRP production with cleavage deficient helper constructs.

| RNA combination | Capsid helper | GP helper | inhibitor added | VRP/ml |
|---|---|---|---|---|
| 1 | pHCMV-Vsp | NA | no | 7.2E+07 |
| 2 | pHCM-Vsp(m152) | NA | no | 0 |
| 3 | dHcap6-mut1(W-stop)m152 | dHgp6-mut1 | no | 7.9E+08 |

TABLE 2-continued

VRP production with cleavage deficient helper constructs.

| RNA combination | Capsid helper | GP helper | inhibitor added | VRP/ml |
|---|---|---|---|---|
| 4 | dHcap6-mut1(W-Stop)m152 RC4-6 | dHgp6-mut1 | no | 1.4E+06 |
| 5 | dHcap6-mut1(W-Stop)m152 RC4-6 | dHgp6-mut1 | yes | 8.6E+08 |

The data indicate that the H→G change at amino acid 152 of the capsid protein blocks the production of VEE RP when the mutation is in the context of a DNA helper; in this context the capsid would rely on the autoprotease function to cleave itself from the co-translated VEE glycoproteins (compare RNA combination 1 and 2). In contrast, if the m152 mutation is introduced into a capsid helper RNA (where the autoprotease activity is not required) VEE RP are produced (RNA combination 3). Furthermore, introduction of m152 into miRNA targeted capsid helper also has no negative affect on VEE RP yield as long as miRNA inhibitor is added to the electroporation mix (compare RNA combination 4 and 5).

Experiments to determine cell type specificity of miRNA activity on alphavirus RNA replication. All of the previous experiments were conducted in Vero cells. To determine whether the miRNA targets we have tested in Vero cells have the same function in other cell types, replicon vectors that express the CAT reporter gene were constructed that code for three or six copies of each individual miRNA target (e.g., pERK/342/EMCV/CAT-RC1x6, pERK/342/EMCV/CAT-RC2x6, pERK/342/EMCV/CAT-RC7x3, etc.). VEE RP preparations were prepared by electroporating Vero cells, in the presence of the relevant miRNA inhibitor, with each of the miRNA targeted CAT replicon RNAs combined with unmodified capsid and GP helper RNAs. To eliminate difficulty in determining accurate Vero cell infectious unit (IU) titers of these VEE RP preparations (due to the effect of the miRNAs present in Vero cells reducing the effective IU titer) replicon genome equivalents (GE) were determined by quantitative reverse transcriptase PCR. Genome equivalent titers were used to control the multiplicity of infection (MOI) for each of the cell types analyzed. The MOI used was 3-5 in each of these experiments. A summary of the relative miRNA activity detected in each cell type, based on the percent of CAT expressed from each of the miRNA targeted replicons relative to an unmodified CAT replicon is shown in Table 3 and Table 4.

TABLE 3

MicroRNA Activity in Various Cell Types (RC 1-6).

| | Cell type | | | | | | | | | |
|---|---|---|---|---|---|---|---|---|---|---|
| | Human | | | | | | Hamster | | NHP | Mouse |
| | Muscle | | | Lung | Musc. Cell | Hep. | Kid. | Ovary | Kid. | Bov. | Neuron |
| Replicon (miRNA) | HEL-299 | RD | MO-59K | MRC-5 | SkM | PHH | BHK | CHO | Vero | BT | CN |
| | Relative % CAT Expression vs. CAT replicon control | | | | | | | | | | |
| CAT (none) | 100 | 100 | 100 | 100 | 100 | 100 | 100 | 100 | 100 | 100 | 100 |
| CAT (RC1-6) | 0 | 5 | 0 | 1 | nt | nt | 1 | 0 | 0 | nt | nt |
| CAT (RC1x6) | 0 | 20 | 0 | 0 | 1 | 0 | 0 | 0 | 0 | 0 | 6 |
| CAT (RC2x6) | 3 | 20 | 15 | 4 | 11 | 0 | 31 | 1 | 42 | 8 | 59 |
| CAT (RC3x6) | 26 | 41 | 50 | 49 | 38 | 0 | 86 | 36 | 37 | 50 | 70 |
| CAT (RC4x6) | 13 | 52 | 46 | 57 | 42 | 32 | 81 | 66 | 11 | 55 | 100 |
| CAT (RC5x6) | 7 | 0 | 6 | 35 | 14 | 0 | 13 | 0 | 1 | 18 | 2 |
| CAT (RC6x6) | 11 | 8 | 28 | 45 | 30 | 0 | 60 | 8 | 14 | 32 | 74 |

TABLE 4

MicroRNA Activity in Various Cell Types (RC 7-12)

| | Cell type | | | |
|---|---|---|---|---|
| | Human Muscle | Mouse Neuron | | NHP Kidney |
| | | Cell name | | |
| Replicon (miRNA) | RD | SkM | CN | Vero |
| | Relative % CAT expression vs. CAT replicon control | | | |
| CAT (none) | 100 | 100 | 100 | 100 |
| CAT (RC7 × 3) | 49 | 10 | 80 | 55 |
| CAT (RC8 × 3) | 2 | 6 | 39 | 4 |
| CAT (RC9 × 3) | 3 | 6 | 1 | 32 |
| CAT (RC10 × 3) | 100 | 31 | 46 | 54 |
| CAT (RC11 × 3) | 15 | 100 | 100 | 100 |
| CAT (RC12 × 3) | 11 | 54 | 17 | 100 |

VEE RP generated with a CAT replicon carrying all six of the miRNA targets (CAT 1-6) expressed very little CAT protein in any cell type tested. Similarly, minimal CAT protein could be detected in cells infected with VEE RP containing a replicon RNA carrying the let-7 miRNA target (CAT RC1×6). These results show that the let-7 miRNA is present in all of the cell types tested. CAT protein levels detected in cells infected with the other individual miRNA targeted CAT replicons indicated a range of protein expression. These data show that each different cell type had a different complement of active miRNAs available to control replication of replicon RNA.

Experiments to determine in vivo miRNA activity on alphavirus RNA replication. The data described above indicate that the miRNA-targeted helper and replicon RNAs can be controlled by the action of cellular miRNAs in a wide array of cells in culture (in vitro). To determine whether the same miRNA control demonstrated in vitro could be demonstrated in vivo, a number of VEE RP preparations were produced and tested in BALB/c mice. Combinations of both miRNA-targeted helpers were mixed with unmodified or miRNA-targeted replicon vectors expressing the influenza HA gene (A/Wisconsin). A summary of the helper and replicon RNA combinations is shown in Table 5.

TABLE 5

Summary of Helper and Replicon RNA Combinations.

| Group Identifier | Replicon RNA | Capsid Helper | GP Helper |
|---|---|---|---|
| Wild type ("WT") | pERK/342/EV71/A(Wis)/HA | dHcap6-mut1 (W-stop) | dHgp6-mut1 |
| miCap | pERK/342/EV71/A(Wis)/HA | dHcap6-mut1 (W-stop) RC1-6 | dHgp6-mut1 |
| miGP | pERK/342/EV71/A(Wis)/HA | dHcap6-mut1 (W-stop) | dHgp6-mut1-RC1-6 |
| miCap + miGP | pERK/342/EV71/A(Wis)/HA | dHcap6-mut1 (W-stop) RC1-6 | dHgp6-mut1-RC1-6 |
| miRep + miCap + miGP | pERK/342/EV71/A(Wis)/HA-RC1-6 | dHcap6-mut1 (W-stop) RC1-6 | dHgp6-mut1-RC1-6 |

Figure 22:
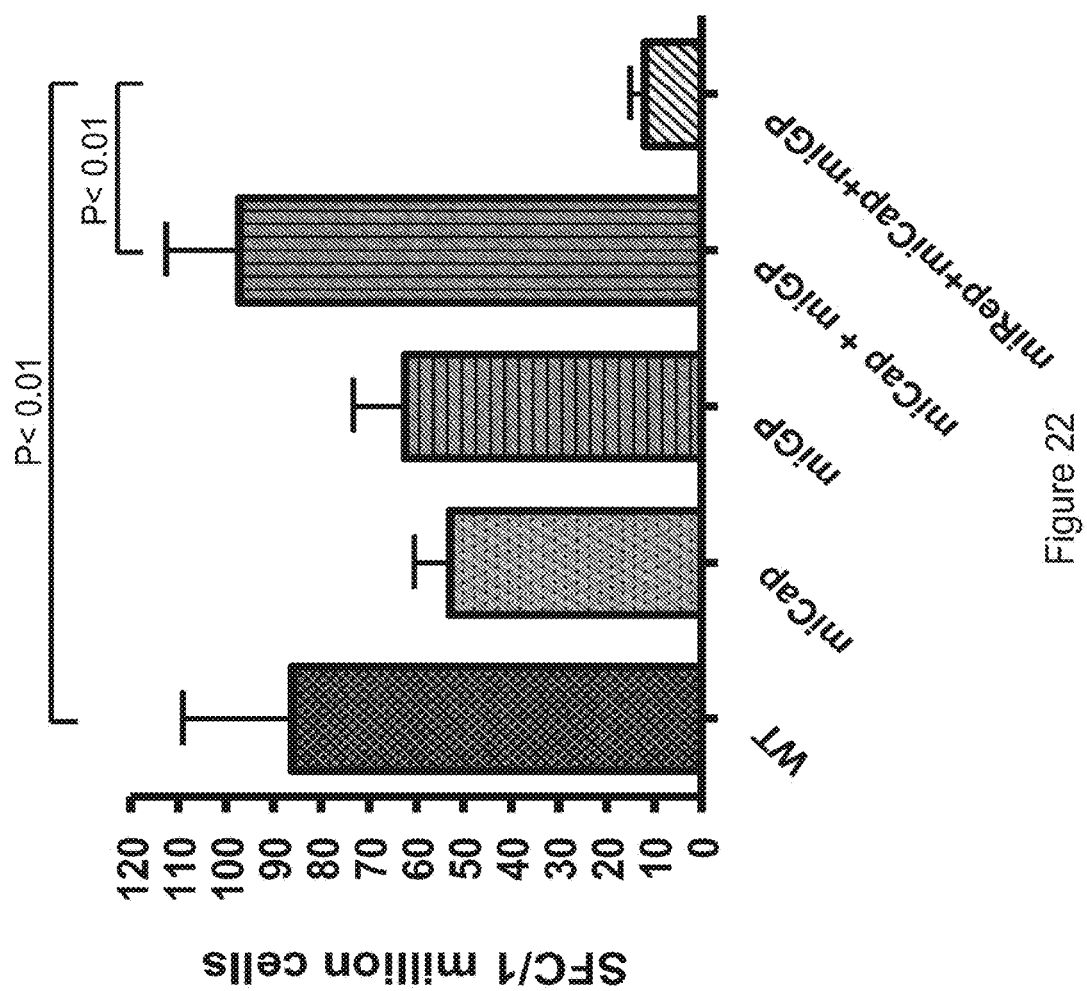
Figure 23:
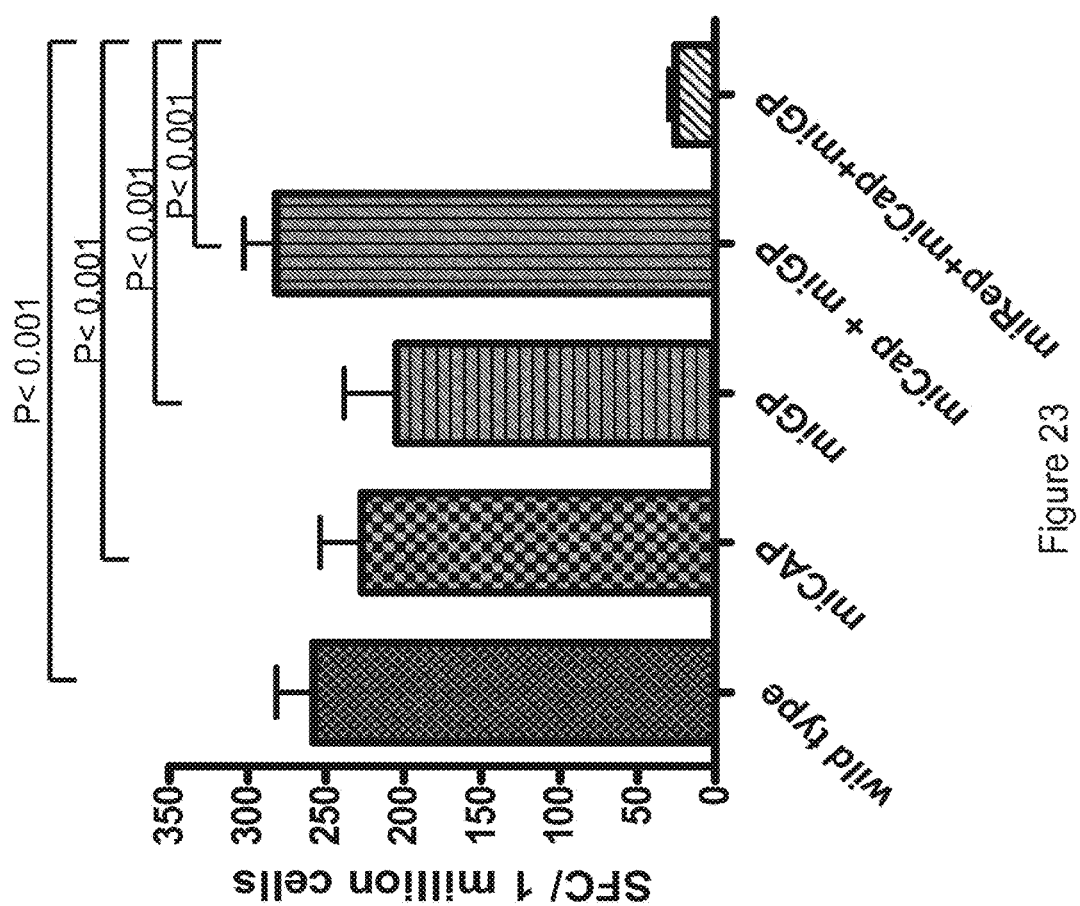
Figure 24:
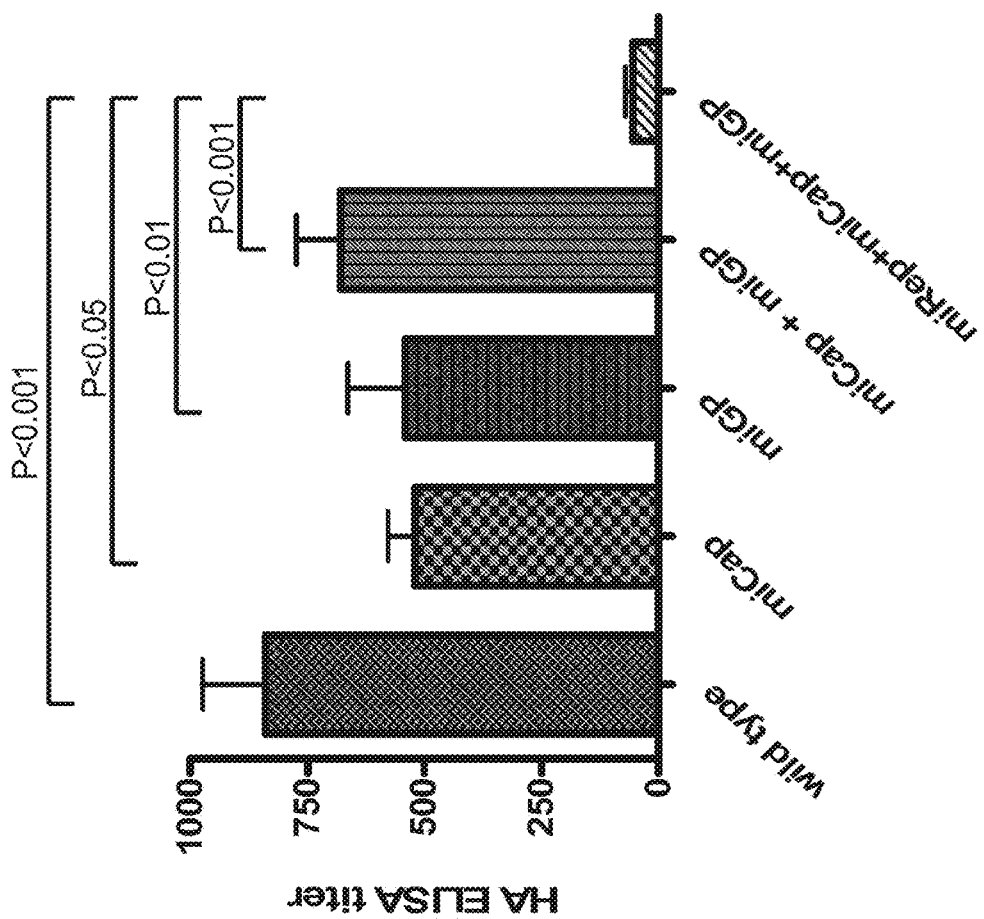
Figure 25:
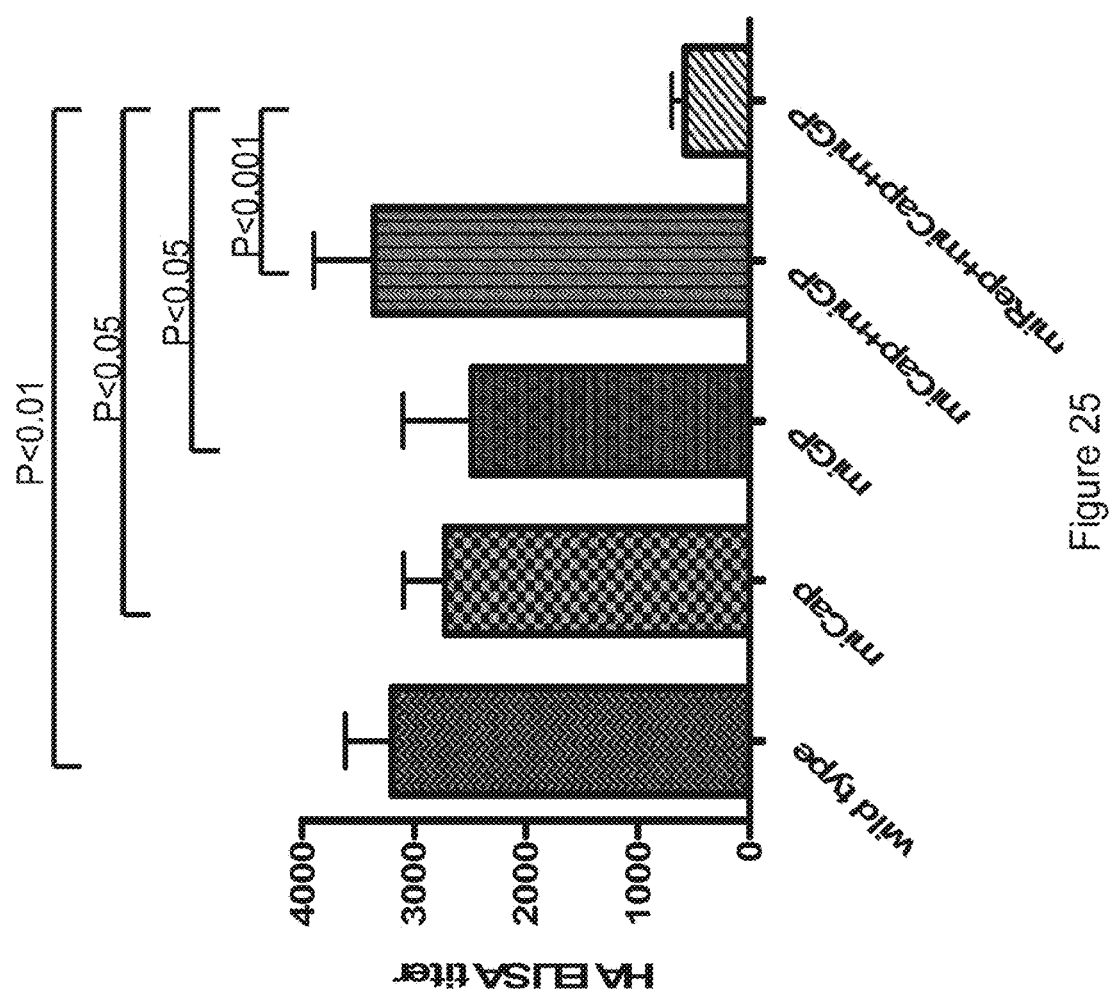

Groups of 16 mice were immunized with equivalent doses of each of the VEE RP. Seven days after the priming dose, half (8) of the mice were sacrificed, the splenocytes were collected and HA-specific gamma interferon ELISPOT analysis was conducted. The results of the 7 day post-prime HA-specific ELISPOT analysis are shown in FIG. 22. There were significantly less spot forming cells (SFCs) in the group immunized with VEE RP generated with miRNA-targeted replicon and helper RNAs ("miRep+miCap+miGP") than in the groups immunized with VEE RP generated with unmodified replicon and helper RNAs ("WT") or with VEE RP generated with unmodified replicon RNA and miRNA-targeted capsid and GP helpers ("miCap+miGP"). Three weeks after the priming dose, the remaining mice in each group were boosted with their respective HA VEE RP. Seven days after the boost the remaining animals were sacrificed and the splenocytes were collected for HA-specific gamma interferon ELISPOT analysis. The post boost HA-specific ELISPOT analysis are shown in FIG. 23. After the boost, the SFCs detected in the group immunized with VEE RP generated using miRNA-targeted replicon RNA were significantly lower than those detected in all of the other VEE RP immunized groups. Furthermore, HA-specific ELISA analysis of both post prime (FIG. 24) and post boost (FIG. 25) serum samples demonstrated that animals immunized with VEE RP generated with an miRNA-targeted replicon were significantly lower than all other VEE RP immunized groups. These data show that the miRNA-targeted replicon VEE RP were significantly inhibited from inducing an HA specific cellular or humoral immune response.

A second mouse study was conducted using VEE RP generated with miRNA-targeted helper RNAs. A different complement of miRNA targets was engineered into the 3' UTR of RNA helpers used in this study. The capsid and gp helper RNAs contained the following miRNA targets: RC1, RC4, RC5, RC9, RC2, RC3, RC10, RC7 and RC12 (5'-gcatgcaactatacaacctactacctcacccctatcacgattagcattaaactacct-gcactgtaagcactttgactcaccgac agcgttgaatgttacacagtcgaag-gtctcagggacttcagnatcacagtactgtaggcattcaccgcgtgccttagagcta cagtgcttcatctcacagctggttgaaggggaccaaagtttaaac-3' (SEQ ID NO:39)). A replicon vector expressing the herpes simplex virus II gD (HSV gD) gene was packaged into VEE RP with 4 different complements of helper RNAs as shown in Table 6.

TABLE 6

Replicon and helper RNA combinations used to generate HSV VRP.

| Group indentifier | Replicon RNA | Capsid helper | GP helper |
|---|---|---|---|
| Wild type | pAVP1 HSV | dHcap6-mut1(W-stop) | dHgp6-mut1 |
| 152 | pAVP1 HSV | dHcap6-mut1(W-stop)152 | dHgp6-mut1 |
| mi | pAVP1 HSV | dHcap6-mut1(W-stop)mi | dHgp6-mut1 mi |
| mi152 | pAVP1 HSV | dHcap6-mut1(W-stop)mi152 | dHgp6-mut1 mi |

Figure 26:
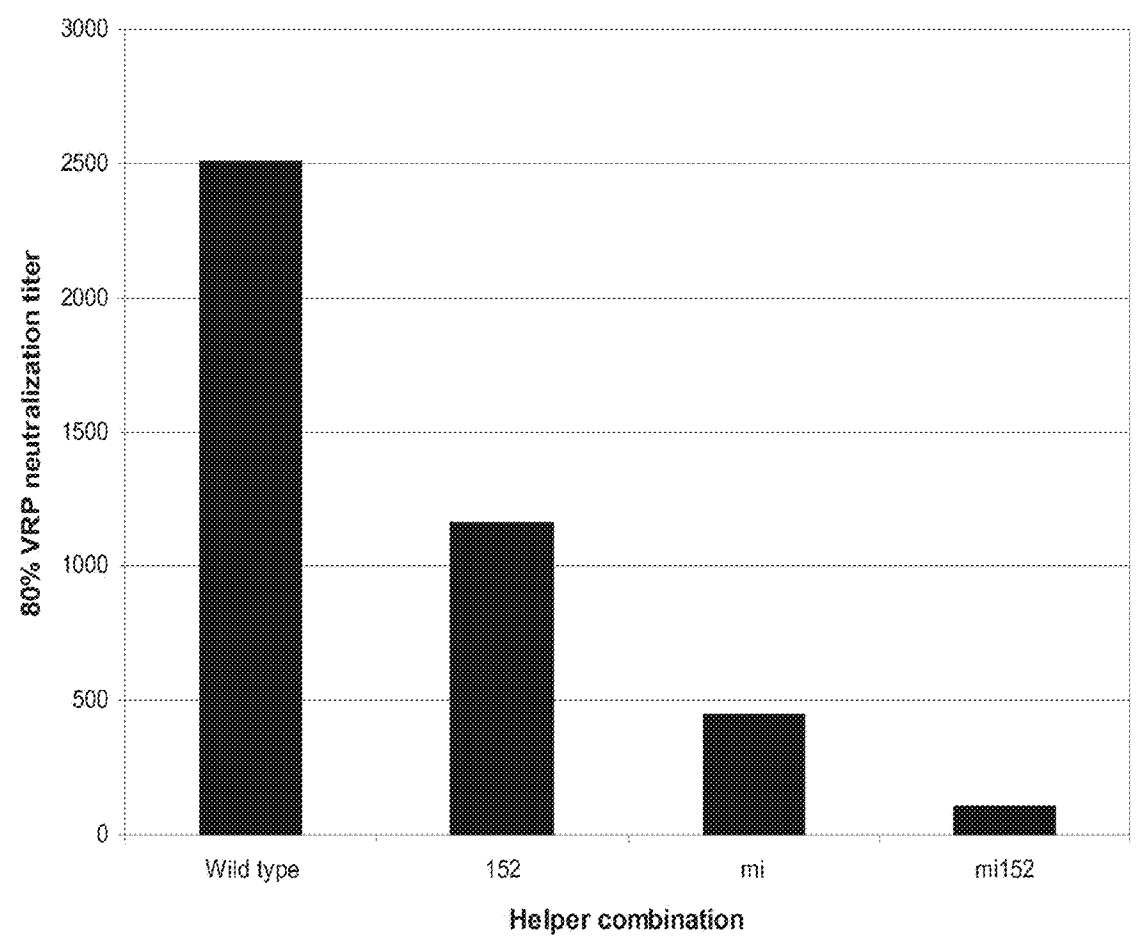

Groups of 6 mice were immunized with 5×10⁶ IU of each VEE RP at 0 and 3 weeks. No difference was noted in the HSV gD-specific humoral or cellular responses detected in animals immunized with HSV VEE RP packaged with the different helper RNA combinations. The anti-VEE RP immune response, also referred to as an "anti-vector response", elicited in the vaccinated animals was also determined. The results of VEE RP neutralization assays carried out with serum collected from vaccinated animals is shown in FIG. 26. Animals vaccinated with VEE RP generated with miRNA-targeted helper RNAs demonstrated lower anti-VEE RP neutralization titers than animals vaccinated with VEE RP generated with helper RNAs that did not code for miRNA targets. These data indicate that it is possible to reduce anti-vector immune responses by packaging VEE RP with miRNA-targeted helper RNAs.

Taken together, the two mouse studies presented above indicate that miRNA target-specific inhibition of both replicon and helper RNA replication is occurring in vivo. These results arc in complete agreement with the miRNA target-specific inhibition that was demonstrated in vitro in the absence of miRNA inhibitors. The in vitro and in vivo data presented above show that engineering miRNA targets into alphavirus helper RNAs controls replication/expression of these RNAs in cells where helper function is not required or wanted.

Efficacy of VRP made with miRNA-Targeted Helpers in Non-Human Primates

Replicon vectors were constructed using the L1R gene from vaccinia virus (VACV) which is a homolog to a similar gene in smallpox. Two different alphavirus vector systems were used: "pVEK" which is derived from TC83, and "pERK" which is derived from attenuated VEE strain V3014. The L1R gene was modified to include a TPA signal sequence which enhances the immunogenicity of the construct. L1R-expressing VEE RP were generated using miRNA targeted helpers (described hereinabove as dHcap6-mut1(W-stop)mi152 and dHgp6-mut1mi).

Groups of five Cynomolgus macaques were vaccinated by the intramuscular route on week 0 and 28 as follows: Group 1, $5 \times 10^7$ IU of pVEK L1R-VRP; Group 2, a combination of $2.5 \times 10^7$ IU of pVEK L1R-VRP and $2.5 \times 10^7$ IU of pERK L1R VRP; and group 3, $5 \times 10^7$ IU of pVEK L1R-VRP. Serum and PBMC samples were collected from animals on day 0, 21 (prime), 35 (1 wk PB) and 56 (4 wk PB). The results are summarized in Table 7.

TABLE 7

Summary of results for vaccinated Cynomolgus macaques.

| Group | VRP Vaccine | Log ELISA GMT | | | $PRNT_{50}$ | Mean L1R Specific $SFC^c$ | | |
|---|---|---|---|---|---|---|---|---|
| | | prime | 1 wk $PB^a$ | 4 wk PB | $GMT^b$ | prime | 1 wk $PB^a$ | 4 wk PB |
| 1 | pVEK L1R | 3.4 | 5.6 | 5.0 | 183.8 | 12 | 109 | 155 |
| 2 | pVEK L1R + pERK L1R | 3.8 | 5.1 | 4.2 | 211.1 | 9 | 34 | 18 |
| 3 | pERK L1R | 3.5 | 5.1 | 4.6 | 139.3 | 15 | 24 | 59 |

[a]post-boost
[b]VacV neutralizing antibody geometric mean titer
[c]per $10^6$ PBMC (background subtracted)

The immune responses detected in these macaques were consistent with the responses previously detected in animals receiving a mixture of L1R-expressing VEE RP and 3 other VACV gene-expressing VEE RP in a challenge study in which vaccinated macaques were significantly protected from lethal disease. These data indicate that VRP generated with miRNA targeted helpers arc immunogenic in non-human primates.

What is claimed is:

1. A population of alphavirus-like replicon particles (ARPs) comprising:
   (1) a first subset of particles comprising an alphavirus replicon and
   (2) a second subset of particles comprising a helper nucleic acid or fragment thereof, wherein the helper nucleic acid comprises:
      (i) a 5' alphavirus replication recognition sequence;
      (ii) a nucleic acid sequence encoding an alphavirus structural protein;
      (iii) a 3' alphavirus replication recognition sequence; and
      (iv) at least one microRNA target sequence of a cellular microRNA, wherein the helper nucleic acid is propagation defective and the fragment of the helper nucleic acid comprises the at least one microRNA target sequence, and an alphavirus replicon.

2. The population of claim 1, wherein the ARPs are ARPs of South African Arbovirus No. 86, Sindbis virus, Semliki Forest virus, and Ross River virus.

3. The population of claim 1, wherein the ARPs are Venezuelan equine encephalitis (VEE) virus ARPS.

4. A method of inducing an immune response in a subject comprising administering to the subject the population of alphavirus-like replicon particles of claim 1.

5. A method of making alphavirus-like replicon particles (ARPs) comprising:
   (1) transfecting a cell with (i) an alphavirus replicon, and
      (ii) one or more helper nucleic acids comprising:

(i) a 5' alphavirus replication recognition sequence;
(ii) a nucleic acid sequence encoding an alphavirus structural protein;
(iii) a 3' alphavirus replication recognition sequence; and
(iv) at least one microRNA target sequence of a cellular microRNA, and wherein the helper nucleic acid is propagation defective; and wherein the structural proteins necessary to make the virus-like replicon particle are encoded by one or more of the cell, the alphavirus replicon or the helper nucleic acid;

(2) culturing the cell under conditions that allow for production of assembled virus-like replicon particles comprising the alphavirus replicon; and (3) collecting the ARPs.

6. The method of claim 5, wherein the cell is transfected with a first helper nucleic acid and a second helper nucleic acid, wherein the first and second helper nucleic acids encode the alphavirus structural proteins necessary to make ARPs and wherein the second helper nucleic acid encodes at least one or more alphavirus structural proteins not encoded by the first helper nucleic acid.

7. The method of claim 5, wherein the cell is cultured in the presence of an inhibitor of at least one cellular microRNA.

8. The method of claim 5, wherein the ARPs are ARPs of South African Arbovirus No. 86, Sindbis virus, Semliki Forest virus, and Ross River virus.

9. The method of claim 5, wherein the ARPs are Venezuelan equine encephalitis (VEE) virus ARPS.

10. A helper nucleic acid comprising:
(a) a 5' alphavirus replication recognition sequence;
(b) a nucleic acid sequence encoding at least one, but not all alphavirus structural proteins;
(c) a 3' alphavirus replication recognition sequence; and
(d) at least one microRNA target sequence of a cellular microRNA, wherein the helper nucleic acid is propagation defective.

11. The helper nucleic acid of claim 10, wherein
(a) at least one microRNA target sequence is located in a 3' UTR of the nucleic acid sequence encoding the alphavirus structural protein;
(b) at least one microRNA target sequence is located in a 5' UTR of the nucleic acid sequence encoding the alphavirus structural protein; (c) at least one microRNA target sequence is located in the translated region of the nucleic acid sequence encoding the alphavirus structural protein, or
(a) and (b).

12. The helper nucleic acid of claim 10, wherein the alphavirus structural protein is selected from the group consisting of Venezuelan equine encephalitis (VEE) virus, South African Arbovirus No. 86, Sindbis virus, Semliki Forest Virus, and Ross River Virus structural proteins.

13. The helper nucleic acid of claim 10, wherein the alphavirus structural protein is an alphavirus capsid protein or is an alphavirus glycoprotein.

14. The helper nucleic acid of claim 10, wherein the alphavirus structural protein is a VEE capsid protein comprising an amino acid substitution at amino acid 152 and wherein the amino acid substitution is H152G.

15. A composition comprising:
(a) a helper nucleic acid of claim 10, and
(b) an alphavirus replicon.

16. A population of alphavirus-like replicon particles (ARPs) comprising:
(1) a first subset of particles comprising a replicon and
(2) a second subset of particles comprising a helper nucleic acid of claim 10 or fragment thereof, wherein the fragment of the helper nucleic acid comprises the at least one microRNA target sequence, and a replicon.

17. A method of inducing an immune response in a subject comprising administering to the subject the population of alphavirus-like replicon particles of claim 16.

18. The population of claim 1, wherein at least one microRNA target sequence is a microRNA target sequence of a eukaryote.

19. The helper nucleic acid of claim 10, wherein at least one microRNA target sequence is a microRNA target sequence of a eukaryote.

20. The composition of claim 15, wherein at least one microRNA target sequence is a microRNA target sequence of a eukaryote.

* * * * *

SEQUENCE LISTING

<160> NUMBER OF SEQ ID NOS: 39

<210> SEQ ID NO 1
<211> LENGTH: 19
<212> TYPE: DNA
<213> ORGANISM: Artificial Sequence
<220> FEATURE:
<223> OTHER INFORMATION: Synthetic Construct

<400> SEQUENCE: 1
ttaatacgac tcactatag                                              19

<210> SEQ ID NO 2
<211> LENGTH: 31
<212> TYPE: DNA
<213> ORGANISM: Artificial Sequence
<220> FEATURE:
<223> OTHER INFORMATION: Synthetic Construct

<400> SEQUENCE: 2
tttgcatgcc ttcagttatc acagtactgt a                                31

<210> SEQ ID NO 3
<211> LENGTH: 31
<212> TYPE: DNA

```
<213> ORGANISM: Artificial Sequence
<220> FEATURE:
<223> OTHER INFORMATION: Synthetic Construct

<400> SEQUENCE: 3
tttgcatgca cacagtcgaa ggtctcaggg a                                    31

<210> SEQ ID NO 4
<211> LENGTH: 33
<212> TYPE: DNA
<213> ORGANISM: Artificial Sequence
<220> FEATURE:
<223> OTHER INFORMATION: Synthetic Construct

<400> SEQUENCE: 4
catgcatgca ctacctgcac tgtaagcact ttg                                  33

<210> SEQ ID NO 5
<211> LENGTH: 32
<212> TYPE: DNA
<213> ORGANISM: Artificial Sequence
<220> FEATURE:
<223> OTHER INFORMATION: Synthetic Construct

<400> SEQUENCE: 5
catgcatgct cagttttgca tagatttgca ca                                   32

<210> SEQ ID NO 6
<211> LENGTH: 33
<212> TYPE: DNA
<213> ORGANISM: Artificial Sequence
<220> FEATURE:
<223> OTHER INFORMATION: Synthetic Construct

<400> SEQUENCE: 6
ggggtttaaa ctgaggtagt aggttgtata gtt                                  33

<210> SEQ ID NO 7
<211> LENGTH: 33
<212> TYPE: DNA
<213> ORGANISM: Artificial Sequence
<220> FEATURE:
<223> OTHER INFORMATION: Synthetic Construct

<400> SEQUENCE: 7
ggggtttaaa ctccctgaga ccttcgactg tgt                                  33

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct

<400> SEQUENCE: 8
taagagccgc gagcgatcct                                                 20

<210> SEQ ID NO 9
<211> LENGTH: 32
<212> TYPE: DNA
<213> ORGANISM: Artificial Sequence
<220> FEATURE:
<223> OTHER INFORMATION: Synthetic Construct

<400> SEQUENCE: 9
gggtttaaac ttaatgctaa tcgtgatagg gg                                   32
```

<210> SEQ ID NO 10
<211> LENGTH: 34
<212> TYPE: DNA
<213> ORGANISM: Artificial Sequence
<220> FEATURE:
<223> OTHER INFORMATION: Synthetic Construct

<400> SEQUENCE: 10
gggtttaaac caaagtgctt acagtgcagg tagt                          34

<210> SEQ ID NO 11
<211> LENGTH: 22
<212> TYPE: DNA
<213> ORGANISM: Homo Sapiens

<400> SEQUENCE: 11
aactatacaa cctactacct ca                                       22

<210> SEQ ID NO 12
<211> LENGTH: 22
<212> TYPE: DNA
<213> ORGANISM: Homo Sapiens

<400> SEQUENCE: 12
acacagtcga aggtctcagg ga                                       22

<210> SEQ ID NO 13
<211> LENGTH: 22
<212> TYPE: DNA
<213> ORGANISM: Homo Sapiens

<400> SEQUENCE: 13
cttcagttat cacagtactg ta                                       22

<210> SEQ ID NO 14
<211> LENGTH: 22
<212> TYPE: DNA
<213> ORGANISM: Homo Sapiens

<400> SEQUENCE: 14
cccctatcac gattagcatt aa                                       22

<210> SEQ ID NO 15
<211> LENGTH: 24
<212> TYPE: DNA
<213> ORGANISM: Homo Sapiens

<400> SEQUENCE: 15
actacctgca ctgtaagcac tttg                                     24

<210> SEQ ID NO 16
<211> LENGTH: 23
<212> TYPE: DNA
<213> ORGANISM: Homo Sapiens

<400> SEQUENCE: 16
tcagttttgc atagatttgc aca                                      23

<210> SEQ ID NO 17
<211> LENGTH: 155
<212> TYPE: DNA
<213> ORGANISM: Artificial Sequence
<220> FEATURE:

<223> OTHER INFORMATION: Synthetic Construct

<400> SEQUENCE: 17
gcatgcaact atacaaccta ctacctcaac acagtcgaag gtctcaggga cttcagttat    60
cacagtactg tagatatccc cctatcacga ttagcattaa actacctgca ctgtaagcac   120
tttgtcagtt ttgcatagat ttgcacagtt taaac                              155

<210> SEQ ID NO 18
<211> LENGTH: 72
<212> TYPE: DNA
<213> ORGANISM: Artificial Sequence
<220> FEATURE:
<223> OTHER INFORMATION: Synthetic Construct

<400> SEQUENCE: 18
gcatgcaact atacaaccta ctacctcaac acagtcgaag gtctcaggga cttcagttat    60
cacagtactg ta                                                        72

<210> SEQ ID NO 19
<211> LENGTH: 77
<212> TYPE: DNA
<213> ORGANISM: Artificial Sequence
<220> FEATURE:
<223> OTHER INFORMATION: Synthetic Construct

<400> SEQUENCE: 19
cccctatcac gattagcatt aaactacctg cactgtaagc actttgtcag ttttgcatag    60
atttgcacag tttaaac                                                   77

<210> SEQ ID NO 20
<211> LENGTH: 21
<212> TYPE: DNA
<213> ORGANISM: Homo Sapiens

<400> SEQUENCE: 20
gagctacagt gcttcatctc a                                              21

<210> SEQ ID NO 21
<211> LENGTH: 22
<212> TYPE: DNA
<213> ORGANISM: Homo Sapiens

<400> SEQUENCE: 21
agctgagtgt aggatgttta ca                                             22

<210> SEQ ID NO 22
<211> LENGTH: 23
<212> TYPE: DNA
<213> ORGANISM: Homo Sapiens

<400> SEQUENCE: 22
actcaccgac agcgttgaat gtt                                            23

<210> SEQ ID NO 23
<211> LENGTH: 20
<212> TYPE: DNA
<213> ORGANISM: Homo Sapiens

<400> SEQUENCE: 23
ggcattcacc gcgtgcctta                                                20

```
<210> SEQ ID NO 24
<211> LENGTH: 22
<212> TYPE: DNA
<213> ORGANISM: Homo Sapiens

<400> SEQUENCE: 24
atacatactt ctttacattc ca                                              22

<210> SEQ ID NO 25
<211> LENGTH: 22
<212> TYPE: DNA
<213> ORGANISM: Homo Sapiens

<400> SEQUENCE: 25
cagctggttg aagggaccaa aa                                              22

<210> SEQ ID NO 26
<211> LENGTH: 125
<212> TYPE: DNA
<213> ORGANISM: Artificial Sequence
<220> FEATURE:
<223> OTHER INFORMATION: Synthetic Construct

<400> SEQUENCE: 26
gcgtttaaac tgagatgaag cactgtagct ctgagatgaa gcactgtagc tctgagatga     60
agcactgtag ctcgcatgct taccattgct cgcagttctc ggagtatac ttcacggtaa    120 ctccc                                                                125

<210> SEQ ID NO 27
<211> LENGTH: 128
<212> TYPE: DNA
<213> ORGANISM: Artificial Sequence
<220> FEATURE:
<223> OTHER INFORMATION: Synthetic Construct

<400> SEQUENCE: 27
gcgtttaaac tgtaaacatc ctacactcag cttgtaaaca tcctacactc agcttgtaaa    60
catcctacac tcagctgcat gcttaccatt gctcgcagtt ctccggagta tacttcacgg    120
taactccc                                                             128

<210> SEQ ID NO 28
<211> LENGTH: 131
<212> TYPE: DNA
<213> ORGANISM: Artificial Sequence
<220> FEATURE:
<223> OTHER INFORMATION: Synthetic Construct

<400> SEQUENCE: 28
gcgtttaaac aacattcaac gctgtcggtg agtaacattc aacgctgtcg gtgagtaaca    60
ttcaacgctg tcggtgagtg catgcttacc attgctcgca gttctccgga gtatacttca    120
cggtaactcc c                                                         131

<210> SEQ ID NO 29
<211> LENGTH: 122
<212> TYPE: DNA
<213> ORGANISM: Artificial Sequence
<220> FEATURE:
<223> OTHER INFORMATION: Synthetic Construct

<400> SEQUENCE: 29
gcgtttaaac taaggcacgc ggtgaatgcc taaggcacgc ggtgaatgcc taaggcacgc    60
```

```
ggtgaatgcc gcatgcttac cattgctcgc agttctccgg agtatacttc acggtaactc    120
cc                                                                   122

<210> SEQ ID NO 30
<211> LENGTH: 128
<212> TYPE: DNA
<213> ORGANISM: Artificial Sequence
<220> FEATURE:
<223> OTHER INFORMATION: Synthetic Construct

<400> SEQUENCE: 30
gcgtttaaac tggaatgtaa agaagtatgt attggaatgt aaagaagtat gtattggaat    60
gtaaagaagt atgtatgcat gcttaccatt gctcgcagtt ctccggagta tacttcacgg    120
taactccc                                                             128

<210> SEQ ID NO 31
<211> LENGTH: 128
<212> TYPE: DNA
<213> ORGANISM: Artificial Sequence
<220> FEATURE:
<223> OTHER INFORMATION: Synthetic Construct

<400> SEQUENCE: 31
gcgtttaaac tttggtcccc ttcaaccagc tgtttggtcc ccttcaacca gctgtttggt    60 cccctttcaac cagctggcat gcttaccatt gctcgcagtt ctccggagta tacttcacgg    120
taactccc                                                             128

<210> SEQ ID NO 32
<211> LENGTH: 34
<212> TYPE: DNA
<213> ORGANISM: Artificial Sequence
<220> FEATURE:
<223> OTHER INFORMATION: Synthetic Construct

<400> SEQUENCE: 32
cctcggaccg accatgttcc cgttccagcc aatg                                34

<210> SEQ ID NO 33
<211> LENGTH: 25
<212> TYPE: DNA
<213> ORGANISM: Artificial Sequence
<220> FEATURE:
<223> OTHER INFORMATION: Synthetic Construct

<400> SEQUENCE: 33
tttcggaccg tgtgcaaatc tatgc                                          25

<210> SEQ ID NO 34
<211> LENGTH: 25
<212> TYPE: DNA
<213> ORGANISM: Artificial Sequence
<220> FEATURE:
<223> OTHER INFORMATION: Synthetic Construct

<400> SEQUENCE: 34
tttcggtccg aactatacaa cctac                                          25

<210> SEQ ID NO 35
<211> LENGTH: 29
<212> TYPE: DNA
<213> ORGANISM: Artificial Sequence
<220> FEATURE:
<223> OTHER INFORMATION: Synthetic Construct
```

```
<400> SEQUENCE: 35
gacattggaa gatcttgtgc aaatctatg                                            29

<210> SEQ ID NO 36
<211> LENGTH: 25
<212> TYPE: DNA
<213> ORGANISM: Artificial Sequence
<220> FEATURE:
<223> OTHER INFORMATION: Synthetic Construct

<400> SEQUENCE: 36
ggagatctcg aactatacaa cctac                                                25

<210> SEQ ID NO 37
<211> LENGTH: 35
<212> TYPE: DNA
<213> ORGANISM: Artificial Sequence
<220> FEATURE:
<223> OTHER INFORMATION: Synthetic Construct

<400> SEQUENCE: 37
gttattcagg ccgatgggtg tggaaggcaa gatcg                                     35

<210> SEQ ID NO 38
<211> LENGTH: 35
<212> TYPE: DNA
<213> ORGANISM: Artificial Sequence
<220> FEATURE:
<223> OTHER INFORMATION: Synthetic Construct

<400> SEQUENCE: 38
cgatcttgcc ttccacaccc atcggcctga ataac                                     35

<210> SEQ ID NO 39
<211> LENGTH: 212
<212> TYPE: DNA
<213> ORGANISM: Artificial Sequence
<220> FEATURE:
<223> OTHER INFORMATION: Synthetic Construct

<400> SEQUENCE: 39
gcatgcaact atacaaccta ctacctcacc cctatcacga ttagcattaa actacctgca          60
ctgtaagcac tttgactcac cgacagcgtt gaatgttaca cagtcgaagg tctcagggac         120
ttcagttatc acagtactgt aggcattcac cgcgtgcctt agagctacag tgcttcatct         180
cacagctggt tgaaggggac caaagtttaa ac                                       212
```